US011973894B2

(12) United States Patent
Abdollahian et al.

(10) Patent No.: US 11,973,894 B2
(45) Date of Patent: Apr. 30, 2024

(54) UTILIZING CONTEXT INFORMATION WITH AN ELECTRONIC DEVICE

(71) Applicant: Apple Inc., Cupertino, CA (US)

(72) Inventors: Golnaz Abdollahian, San Francisco, CA (US); Krishna Dayanidhi, Sunnyvale, CA (US); Patrick T. Dillon, Fremont, CA (US); Aaron R. Zinman, San Francisco, CA (US)

(73) Assignee: Apple Inc., Cupertino, CA (US)

( * ) Notice: Subject to any disclaimer, the term of this patent is extended or adjusted under 35 U.S.C. 154(b) by 357 days.

(21) Appl. No.: 17/607,830

(22) PCT Filed: Apr. 8, 2020

(86) PCT No.: PCT/US2020/027300
§ 371 (c)(1),
(2) Date: Oct. 29, 2021

(87) PCT Pub. No.: WO2020/222988
PCT Pub. Date: Nov. 5, 2020

(65) Prior Publication Data
US 2022/0224789 A1 Jul. 14, 2022

Related U.S. Application Data

(60) Provisional application No. 62/841,109, filed on Apr. 30, 2019.

(51) Int. Cl.
*H04W 4/02* (2018.01)
*G06F 3/0482* (2013.01)
(Continued)

(52) U.S. Cl.
CPC ...... *H04M 1/72454* (2021.01); *G06F 3/0482* (2013.01); *H04M 1/72463* (2021.01); *H04M 1/72469* (2021.01)

(58) Field of Classification Search
CPC ......... H04M 1/72454; H04M 1/72469; H04M 1/72463; G06F 3/0482
See application file for complete search history.

(56) References Cited

U.S. PATENT DOCUMENTS 7,251,696 B1 7/2007 Horvitz
7,831,270 B2 11/2010 Kalley et al.
(Continued)

FOREIGN PATENT DOCUMENTS

EP 2915021 A2 9/2015
EP 3270658 A1 1/2018
(Continued)

OTHER PUBLICATIONS

Notice of Allowance received for U.S. Appl. No. 17/306,489, dated Sep. 26, 2023, 8 pages.
(Continued)

Primary Examiner — Moustapha Diaby
(74) Attorney, Agent, or Firm — DLA Piper LLP (US)

(57) ABSTRACT

The present disclosure generally relates to the utilization of context information by an electronic device. In one example, a context affordance associated with a contextual category is displayed. In response to detecting an input, a plurality of options associated with the contextual category are displayed, including a first option corresponding to a first status that is a current status for the contextual category and a second option corresponding to a second status that is not the current status for the contextual category. When an input is detected that corresponds to the second option of the first plurality of options, the current status for the contextual category is set to the second status.

33 Claims, 25 Drawing Sheets

(51) Int. Cl.
  *H04M 1/72454* (2021.01)
  *H04M 1/72463* (2021.01)
  *H04M 1/72469* (2021.01)
  *H04W 8/18* (2009.01)

(56) References Cited

U.S. PATENT DOCUMENTS

| | | |
|---|---|---|
| 8,010,131 B2 | 8/2011 | Rothschild |
| 8,180,583 B1 | 5/2012 | Gossweiler et al. |
| 8,296,383 B2 | 10/2012 | Lindahl |
| 8,386,620 B2 | 2/2013 | Chatterjee |
| 9,246,984 B2 | 1/2016 | Zises |
| 9,531,803 B2 | 12/2016 | Chen et al. |
| 9,692,611 B1 | 6/2017 | Tom et al. |
| 9,826,375 B2 | 11/2017 | Grifoni |
| 9,832,625 B2 | 11/2017 | Nebel |
| 10,170,135 B1 | 1/2019 | Pearce et al. |
| 10,403,283 B1 | 9/2019 | Schramm et al. |
| 10,757,499 B1 | 8/2020 | Vautrin et al. |
| 10,878,809 B2 * | 12/2020 | Gruber ............... G10L 15/28 |
| 11,038,934 B1 | 6/2021 | Hansen et al. |
| 11,043,220 B1 | 6/2021 | Hansen et al. |
| 11,438,452 B1 | 9/2022 | Abdollahian et al. |
| 2004/0254998 A1 | 12/2004 | Horvitz |
| 2006/0291580 A1 | 12/2006 | Horvitz |
| 2008/0134069 A1 | 6/2008 | Horvitz |
| 2009/0224867 A1 | 9/2009 | O'Shaughnessy et al. |
| 2009/0287750 A1 | 11/2009 | Banavar et al. |
| 2010/0100848 A1 * | 4/2010 | Ananian ............... G06F 3/0482 715/810 |
| 2010/0195865 A1 | 8/2010 | Luff |
| 2010/0229082 A1 | 9/2010 | Karmarkar et al. |
| 2010/0250727 A1 | 9/2010 | King et al. |
| 2011/0028083 A1 | 2/2011 | Soitis |
| 2012/0109753 A1 | 5/2012 | Kennewick et al. |
| 2012/0124138 A1 | 5/2012 | Smith et al. |
| 2012/0232906 A1 | 9/2012 | Lindahl |
| 2012/0265528 A1 | 10/2012 | Gruber et al. |
| 2013/0155948 A1 | 6/2013 | Pinheiro et al. |
| 2013/0184007 A1 | 7/2013 | Hategan et al. |
| 2013/0185081 A1 | 7/2013 | Cheyer et al. |
| 2014/0024956 A1 | 1/2014 | Purdy et al. |
| 2014/0120954 A1 | 5/2014 | Horvitz et al. |
| 2014/0122589 A1 | 5/2014 | Fyke et al. |
| 2014/0128021 A1 | 5/2014 | Walker et al. |
| 2014/0149060 A1 | 5/2014 | Meduna et al. |
| 2014/0223372 A1 * | 8/2014 | Dostie ............... G06F 3/0482 715/813 |
| 2014/0269658 A1 | 9/2014 | Sadasivam et al. |
| 2014/0303839 A1 * | 10/2014 | Filev ............... G06F 3/0481 701/36 |
| 2014/0365885 A1 | 12/2014 | Carson et al. |
| 2015/0004958 A1 | 1/2015 | Wang et al. |
| 2015/0178362 A1 | 6/2015 | Wheeler |
| 2015/0186154 A1 | 7/2015 | Brown et al. |
| 2016/0021153 A1 | 1/2016 | Hull et al. |
| 2016/0028802 A1 | 1/2016 | Balasingh et al. |
| 2016/0094936 A1 | 3/2016 | Yang et al. |
| 2016/0099984 A1 | 4/2016 | Karagiannis et al. |
| 2016/0179075 A1 | 6/2016 | Shin et al. |
| 2016/0198322 A1 | 7/2016 | Pitis |
| 2016/0203193 A1 | 7/2016 | Haverlock et al. |
| 2016/0283463 A1 | 9/2016 | M R et al. |
| 2016/0284172 A1 | 9/2016 | Weast et al. |
| 2016/0336011 A1 | 11/2016 | Koll et al. |
| 2016/0337453 A1 | 11/2016 | Lee |
| 2016/0352924 A1 | 12/2016 | Senarath et al. |
| 2016/0353245 A1 | 12/2016 | Kulikov |
| 2017/0025124 A1 | 1/2017 | Mixter et al. |
| 2017/0038847 A1 | 2/2017 | Schorsch et al. |
| 2017/0046025 A1 * | 2/2017 | Dascola ............... G06F 3/0233 |
| 2017/0090864 A1 | 3/2017 | Jorgovanovic |
| 2017/0093356 A1 | 3/2017 | Cudak et al. |
| 2017/0185375 A1 | 6/2017 | Martel et al. |
| 2017/0289305 A1 | 10/2017 | Liensberger et al. |
| 2017/0289738 A1 | 10/2017 | Jepson et al. |
| 2017/0347222 A1 | 11/2017 | Kanter |
| 2017/0357478 A1 | 12/2017 | Piersol et al. |
| 2017/0357529 A1 | 12/2017 | Venkatraman et al. |
| 2017/0358305 A1 | 12/2017 | Kudurshian et al. |
| 2018/0005442 A1 | 1/2018 | Mullins |
| 2018/0007099 A1 | 1/2018 | Ein-Gil et al. |
| 2018/0018331 A1 | 1/2018 | Kesamreddy |
| 2018/0040020 A1 | 2/2018 | Kurian et al. |
| 2018/0088902 A1 | 3/2018 | Mese et al. |
| 2018/0096690 A1 | 4/2018 | Mixter et al. |
| 2018/0108351 A1 | 4/2018 | Beckhardt et al. |
| 2018/0329957 A1 | 11/2018 | Frazzingaro et al. |
| 2018/0332118 A1 | 11/2018 | Phipps et al. |
| 2018/0336275 A1 | 11/2018 | Graham et al. |
| 2018/0336892 A1 | 11/2018 | Kim et al. |
| 2018/0336904 A1 | 11/2018 | Piercy et al. |
| 2018/0338191 A1 | 11/2018 | Van Scheltinga et al. |
| 2018/0342243 A1 | 11/2018 | VanBlon et al. |
| 2019/0019077 A1 | 1/2019 | Griffin et al. |
| 2019/0049250 A1 | 2/2019 | Takaoka et al. |
| 2019/0082044 A1 | 3/2019 | Melendez et al. |
| 2019/0102145 A1 | 4/2019 | Wilberding et al. |
| 2019/0139541 A1 | 5/2019 | Andersen et al. |
| 2019/0180749 A1 | 6/2019 | Carey et al. |
| 2019/0180750 A1 | 6/2019 | Renard et al. |
| 2019/0180770 A1 | 6/2019 | Kothari et al. |
| 2019/0188328 A1 | 6/2019 | Oyenan et al. |
| 2019/0197053 A1 | 6/2019 | Graham et al. |
| 2019/0278354 A1 | 9/2019 | Alameh et al. |
| 2019/0295544 A1 | 9/2019 | Garcia et al. |
| 2019/0324925 A1 | 10/2019 | Toyoda et al. |
| 2019/0371315 A1 | 12/2019 | Newendorp et al. |
| 2019/0371317 A1 * | 12/2019 | Irani ............... G10L 21/10 |
| 2020/0043489 A1 | 2/2020 | Bradley et al. |
| 2020/0044485 A1 | 2/2020 | Smith et al. |
| 2020/0053218 A1 | 2/2020 | Gray |
| 2020/0075018 A1 | 3/2020 | Chen |
| 2020/0091958 A1 | 3/2020 | Curtis et al. |
| 2020/0092625 A1 | 3/2020 | Raffle |
| 2020/0127988 A1 | 4/2020 | Bradley et al. |
| 2020/0137230 A1 | 4/2020 | Spohrer |
| 2020/0175566 A1 | 6/2020 | Bender et al. |
| 2020/0184964 A1 | 6/2020 | Myers et al. |
| 2020/0187869 A1 | 6/2020 | Thiemjarus et al. |
| 2020/0227034 A1 | 7/2020 | Summa et al. |
| 2020/0252508 A1 | 8/2020 | Gray |
| 2020/0258512 A1 | 8/2020 | Smith et al. |
| 2020/0258513 A1 | 8/2020 | Smith et al. |
| 2020/0302925 A1 | 9/2020 | Shah et al. |
| 2020/0310513 A1 | 10/2020 | Nicholson et al. |
| 2020/0312317 A1 | 10/2020 | Kothari et al. |
| 2020/0334068 A1 | 10/2020 | Krishnamurthy et al. |
| 2020/0380973 A1 | 12/2020 | Novitchenko et al. |
| 2020/0380984 A1 | 12/2020 | Venkatraman et al. |
| 2021/0312917 A1 | 10/2021 | Weksler et al. |
| 2021/0329073 A1 | 10/2021 | Sharma et al. |
| 2021/0350799 A1 | 11/2021 | Hansen et al. |
| 2021/0350803 A1 | 11/2021 | Hansen et al. |
| 2021/0352115 A1 | 11/2021 | Hansen et al. |
| 2021/0366475 A1 | 11/2021 | Wilkosz et al. |
| 2022/0021762 A1 | 1/2022 | Joshi et al. |
| 2022/0197491 A1 | 6/2022 | Meyer et al. |
| 2022/0329685 A1 | 10/2022 | Abdollahian et al. |

FOREIGN PATENT DOCUMENTS

| | | |
|---|---|---|
| EP | 3588912 A1 | 1/2020 |
| IN | 201917007360 A | 5/2019 |
| KR | 10-2016-0004351 A | 1/2016 |
| KR | 10-2017-0096774 A | 8/2017 |
| KR | 10-2018-0133525 A | 12/2018 |
| KR | 10-2020-0007926 A | 1/2020 |
| WO | 2014/200728 A1 | 12/2014 |
| WO | 2017/142116 A1 | 8/2017 |
| WO | 2018/208506 A1 | 11/2018 |

(56) References Cited

FOREIGN PATENT DOCUMENTS

| WO | 2018/213415 A1 | 11/2018 |
|---|---|---|
| WO | 2019/231541 A1 | 12/2019 |

OTHER PUBLICATIONS

Office Action received for Chinese Patent Application No. 202011004874.6, dated Oct. 28, 2023, 13 pages (7 pages of English Translation and 6 pages of Official Copy).
Applicant-Initiated Interview Summary received for U.S. Appl. No. 16/937,408, dated Apr. 7, 2022, 4 pages.
Applicant-Initiated Interview Summary received for U.S. Appl. No. 16/990,868, dated Jan. 29, 2021, 2 pages.
Applicant-Initiated Interview Summary received for U.S. Appl. No. 16/990,876, dated Feb. 3, 2021, 2 pages.
Applicant-Initiated Interview Summary received for U.S. Appl. No. 16/990,894, dated Feb. 1, 2021, 5 pages.
Applicant-Initiated Interview Summary received for U.S. Appl. No. 16/990,894, dated May 3, 2021, 2 pages.
Baby Connect, "Demo Daily Connect", Online Available at : <https://www.youtube.com/watch?v=iqHbq5ru28s>, Mar. 6, 2014, 1 page.
"Better Mood Tracker—Lucid Dreaming App", Online Available at: <https://web.archive.org/web/20190308102914/http://luciddreamingapp.com/better-moad-tracker/, Mar. 8, 2019, 11 pages.
Corrected Notice of Allowance received for U.S. Appl. No. 16/990,868, dated Feb. 25, 2021, 2 pages.
Decision to Grant received for Danish Patent Application No. PA202070546, dated Jun. 10, 2021, 2 pages.
Extended European Search Report received for European Patent Application No. 21171760.8, dated Oct. 8, 2021, 18 pages.
Final Office Action received for U.S. Appl. No. 16/990,894, dated Mar. 25, 2021, 21 pages.
Hello Daylio,"Daylio: Diary and Mood Tracker", Online Available at <https://www.youtube.com/watch?v=5gQUG3gMWik>, Aug. 23, 2015, 1 page.
Intention to Grant received for Danish Patent Application No. PA202070546, dated Feb. 10, 2021, 2 pages.
International Preliminary Report on Patentability received for PCT Patent Application No. PCT/US2020/027300, dated Nov. 11, 2021, 22 pages.
International Preliminary Report on Patentability received for PCT Patent Application No. PCT/US2021/029650, dated Nov. 24, 2022, 43 pages.
International Search Report and Written Opinion received for PCT Patent Application No. PCT/US2020/027300, dated Aug. 4, 2020, 28 pages.
International Search Report and Written Opinion received for PCT Patent Application No. PCT/US2021/029650, dated Dec. 8, 2021, 49 pages.
Invitation to Pay Additional Fees received for PCT Patent Application No. PCT/US2020/027300, dated Jun. 30, 2020, 16 pages.
Invitation to Pay Additional fees received for PCT Patent Application No. PCT/US2021/029650, dated Sep. 6, 2021, 18 pages.
Non-Final Office Action received for U.S. Appl. No. 16/937,408, dated Feb. 3, 2022, 16 pages.
Non-Final Office Action received for U.S. Appl. No. 16/990,868, dated Nov. 19, 2020, 19 pages.
Non-Final Office Action received for U.S. Appl. No. 16/990,876, dated Nov. 18, 2020, 12 pages.
Office Action received for U.S. Appl. No. 16/990,894, dated Dec. 4, 2020, 14 pages.
Office Action received for U.S. Appl. No. 17/306,489, dated Dec. 20, 2022, 17 pages.
Office Action received for U.S. Appl. No. 17/308,452, dated Dec. 22, 2022, 29 pages.
Office Action received for U.S. Appl. No. 17/847,009, dated Dec. 6, 2022, 16 pages.
Notice of Allowance received for U.S. Appl. No. 16/937,408, dated Apr. 27, 2022, 11 pages.
Notice of Allowance received for U.S. Appl. No. 16/990,868, dated Feb. 9, 2021, 9 pages.
Notice of Allowance received for U.S. Appl. No. 16/990,876, dated Feb. 18, 2021, 8 pages.
Notice of Allowance received for U.S. Appl. No. 16/990,894, dated Jul. 21, 2021, 12 pages.
Office Action received for Danish Patent Application No. PA202070546, dated Nov. 30, 2020, 8 pages.
Office Action received for Indian Patent Application No. 202114020735, dated May 25, 2022, 5 pages.
Supplemental Notice of Allowance received for U.S. Appl. No. 16/990,894, dated Oct. 26, 2021, 2 pages.
Applicant-Initiated Interview Summary received for U.S. Appl. No. 17/306,489 dated May 11, 2023, 2 pages.
Corrected Notice of Allowance received for U.S. Appl. No. 17/308,452, dated May 17, 2023, 2 pages.
Non-Final Office Action received for U.S. Appl. No. 17/847,009, dated May 15, 2023, 23 pages.
Office Action received for Korean Patent Application No. 10-2023-7012981, dated Apr. 24, 2023, 7 pages (3 pages of English Translation and 4 pages of Official Copy).
Notice of Allowance received for Korean Patent Application No. 10-2023-7012981, dated Jun. 29, 2023, 7 pages (2 pages of English Translation and 5 pages of Official Copy).
Notice of Allowance received for U.S. Appl. No. 17/847,009, dated Jul. 11, 2023, 10 pages.
Applicant-Initiated Interview Summary received for U.S. Appl. No. 17/308,452, dated Jan. 31, 2023, 2 pages.
Applicant-Initiated Interview Summary received for U.S. Appl. No. 17/847,009, dated Jan. 24, 2023, 4 pages.
Notice of Allowance received for Korean Patent Application No. 10-2022-7042877, dated Jan. 18, 2023, 9 pages (2 pages of English Translation and 7 pages of Official Copy).
Notice of Allowance received for Korean Patent Application No. 10-2022-7042984, dated Jan. 18, 2023, 9 pages (2 pages of English Translation and 7 pages of Official Copy).
Notice of Allowance received for U.S. Appl. No. 17/306,489, dated Jun. 12, 2023, 8 pages.
Final Office Action received for U.S. Appl. No. 17/308,452, dated Feb. 28, 2023, 19 pages.
Final Office Action received for U.S. Appl. No. 17/847,009, dated Feb. 23, 2023, 23 pages.
Applicant-Initiated Interview Summary received for U.S. Appl. No. 17/847,009, dated Apr. 18, 2023, 3 pages.
Final Office Action received for U.S. Appl. No. 17/306,489, dated Apr. 10, 2023, 12 pages.
Notice of Allowance received for U.S. Appl. No. 17/308,452, dated Apr. 5, 2023, 10 pages.
Office Action received for European Patent Application No. 21171760.8, dated Apr. 12, 2023, 12 pages.
Notice of Allowance received for U.S. Appl. No. 17/308,452, dated Aug. 1, 2023, 10 pages.
Corrected Notice of Allowance received for U.S. Appl. No. 17/308,452, dated May 24, 2023, 2 pages.

* cited by examiner

UTILIZING CONTEXT INFORMATION WITH AN ELECTRONIC DEVICE

CROSS-REFERENCE TO RELATED APPLICATIONS

This application is a U.S. National Stage Patent Application of PCT/US2020/027300, entitled "UTILIZING CONTEXT INFORMATION WITH AN ELECTRONIC DEVICE", filed Apr. 8, 2020, which claims the benefit of U.S. Provisional Application No. 62/841,109, entitled "UTILIZING CONTEXT INFORMATION WITH AN ELECTRONIC DEVICE," filed Apr. 30, 2019, the entire contents of which are hereby incorporated by reference.

FIELD

The present disclosure relates generally to context-aware electronic devices, and more specifically to techniques for utilizing context information with an electronic device.

BACKGROUND

Users are increasingly using electronic devices in a variety of locations and while performing a variety of activities. For example, electronic devices can be used during work meetings, while at the gym, or while at home watching a movie.

BRIEF SUMMARY

Some techniques for utilizing an electronic device, however, are generally unaware of the location, activity, or other contexts associated with a user of the electronic device. Without context information, some existing techniques require more time than necessary, wasting user time and device energy. This latter consideration is particularly important in battery-operated devices.

Accordingly, the present techniques provide electronic devices with context information, resulting in faster, more efficient methods and interfaces for utilizing the electronic devices. Such methods and interfaces optionally complement or replace other methods for utilizing electronic devices. Such methods and interfaces reduce the cognitive burden on a user and produce a more efficient human-machine interface. For battery-operated computing devices, such methods and interfaces conserve power and increase the time between battery charges.

In some embodiments, a method is performed at an electronic device with a display. The method includes: displaying one or more context affordances, including a first context affordance associated with a first contextual category; detecting a first input corresponding to the first context affordance; in response to detecting the first input, displaying a first plurality of options associated with the first contextual category, the first plurality of options including a first option corresponding to a first status that is a current status for the first contextual category and a second option corresponding to a second status that is not the current status for the contextual category; while displaying the first plurality of options associated with the first contextual category, detecting a second input; in accordance with a determination that the second input corresponds to the first option of the first plurality of options: disabling the first contextual category associated with the first context affordance; in accordance with a determination that the second input corresponds to the second option of the first plurality of options: setting the current status for the first contextual category to the second status.

In some embodiments, a non-transitory computer-readable storage medium stores one or more programs configured to be executed by one or more processors of an electronic device with a display. The one or more programs include instructions for: displaying one or more context affordances, including a first context affordance associated with a first contextual category; detecting a first input corresponding to the first context affordance; in response to detecting the first input, displaying a first plurality of options associated with the first contextual category, the first plurality of options including a first option corresponding to a first status that is a current status for the first contextual category and a second option corresponding to a second status that is not the current status for the contextual category; while displaying the first plurality of options associated with the first contextual category, detecting a second input; in accordance with a determination that the second input corresponds to the first option of the first plurality of options: disabling the first contextual category associated with the first context affordance; in accordance with a determination that the second input corresponds to the second option of the first plurality of options: setting the current status for the first contextual category to the second status.

In some embodiments, a transitory computer-readable storage medium stores one or more programs configured to be executed by one or more processors of an electronic device with a display. The one or more programs include instructions for: displaying one or more context affordances, including a first context affordance associated with a first contextual category; detecting a first input corresponding to the first context affordance; in response to detecting the first input, displaying a first plurality of options associated with the first contextual category, the first plurality of options including a first option corresponding to a first status that is a current status for the first contextual category and a second option corresponding to a second status that is not the current status for the contextual category; while displaying the first plurality of options associated with the first contextual category, detecting a second input; in accordance with a determination that the second input corresponds to the first option of the first plurality of options: disabling the first contextual category associated with the first context affordance; in accordance with a determination that the second input corresponds to the second option of the first plurality of options: setting the current status for the first contextual category to the second status.

In some embodiments, an electronic device includes a display, one or more processors, and memory. The memory stores one or more programs configured to be executed by the one or more processors. The one or more programs including instructions for: displaying one or more context affordances, including a first context affordance associated with a first contextual category; detecting a first input corresponding to the first context affordance; in response to detecting the first input, displaying a first plurality of options associated with the first contextual category, the first plurality of options including a first option corresponding to a first status that is a current status for the first contextual category and a second option corresponding to a second status that is not the current status for the contextual category; while displaying the first plurality of options associated with the first contextual category, detecting a second input; in accordance with a determination that the second input corresponds to the first option of the first plurality of options: disabling the first contextual category associated with the first context affordance; in accordance with a determination that the second input corresponds to the second option of the first plurality of options: setting the current status for the first contextual category to the second status.

In some embodiments, an electronic device includes: a display; means for displaying one or more context affordances, including a first context affordance associated with a first contextual category; means for detecting a first input corresponding to the first context affordance; means for, in response to detecting the first input, displaying a first plurality of options associated with the first contextual category, the first plurality of options including a first option corresponding to a first status that is a current status for the first contextual category and a second option corresponding to a second status that is not the current status for the contextual category; means for, while displaying the first plurality of options associated with the first contextual category, detecting a second input; means for, in accordance with a determination that the second input corresponds to the first option of the first plurality of options: disabling the first contextual category associated with the first context affordance; means for, in accordance with a determination that the second input corresponds to the second option of the first plurality of options: setting the current status for the first contextual category to the second status.

In some embodiments, a method is performed at an electronic device. The method includes: receiving a first notification of a first type; determining a current status for one or more contextual categories; in accordance with a determination that the current status for the one or more contextual categories satisfies a set of one or more delivery criteria for notifications of the first type: providing the first notification of the first type; in accordance with a determination that the current status for the one or more contextual categories does not satisfy the set of one or more delivery criteria for notifications of the first type: modifying the first notification of the first type to a second notification of a second type; and providing the second notification of the second type.

In some embodiments, a non-transitory computer-readable storage medium stores one or more programs configured to be executed by one or more processors of an electronic device. The one or more programs include instructions for: receiving a first notification of a first type; determining a current status for one or more contextual categories; in accordance with a determination that the current status for the one or more contextual categories satisfies a set of one or more delivery criteria for notifications of the first type: providing the first notification of the first type; in accordance with a determination that the current status for the one or more contextual categories does not satisfy the set of one or more delivery criteria for notifications of the first type: modifying the first notification of the first type to a second notification of a second type; and providing the second notification of the second type.

In some embodiments, a transitory computer-readable storage medium stores one or more programs configured to be executed by one or more processors of an electronic device. The one or more programs include instructions for: receiving a first notification of a first type; determining a current status for one or more contextual categories; in accordance with a determination that the current status for the one or more contextual categories satisfies a set of one or more delivery criteria for notifications of the first type: providing the first notification of the first type; in accordance with a determination that the current status for the one or more contextual categories does not satisfy the set of one or more delivery criteria for notifications of the first type: modifying the first notification of the first type to a second notification of a second type; and providing the second notification of the second type.

In some embodiments, an electronic device includes one or more processors and memory. The memory stores one or more programs configured to be executed by the one or more processors. The one or more programs including instructions for: receiving a first notification of a first type; determining a current status for one or more contextual categories; in accordance with a determination that the current status for the one or more contextual categories satisfies a set of one or more delivery criteria for notifications of the first type: providing the first notification of the first type; in accordance with a determination that the current status for the one or more contextual categories does not satisfy the set of one or more delivery criteria for notifications of the first type: modifying the first notification of the first type to a second notification of a second type; and providing the second notification of the second type.

In some embodiments, an electronic device includes: means for receiving a first notification of a first type; means for determining a current status for one or more contextual categories; means for, in accordance with a determination that the current status for the one or more contextual categories satisfies a set of one or more delivery criteria for notifications of the first type: providing the first notification of the first type; means for, in accordance with a determination that the current status for the one or more contextual categories does not satisfy the set of one or more delivery criteria for notifications of the first type: modifying the first notification of the first type to a second notification of a second type; and providing the second notification of the second type.

In some embodiments, a method is performed at an electronic device. The method includes: determining a predicted status for one or more contextual categories of a potential communication participant; in accordance with a determination that the predicted status for the one or more contextual categories satisfies a set of one or more communication criteria: providing a first recommendation to initiate a first type of communication with the potential communication participant; in accordance with a determination that the predicted status for the one or more contextual categories does not satisfy the set of one or more communication criteria: providing a second recommendation to initiate a second type of communication with the potential communication participant.

In some embodiments, a non-transitory computer-readable storage medium stores one or more programs configured to be executed by one or more processors of an electronic device. The one or more programs include instructions for: determining a predicted status for one or more contextual categories of a potential communication participant; in accordance with a determination that the predicted status for the one or more contextual categories satisfies a set of one or more communication criteria: providing a first recommendation to initiate a first type of communication with the potential communication participant; in accordance with a determination that the predicted status for the one or more contextual categories does not satisfy the set of one or more communication criteria:

providing a second recommendation to initiate a second type of communication with the potential communication participant.

In some embodiments, a transitory computer-readable storage medium stores one or more programs configured to be executed by one or more processors of an electronic device. The one or more programs include instructions for: determining a predicted status for one or more contextual categories of a potential communication participant; in accordance with a determination that the predicted status for the one or more contextual categories satisfies a set of one or more communication criteria: providing a first recommendation to initiate a first type of communication with the potential communication participant; in accordance with a determination that the predicted status for the one or more contextual categories does not satisfy the set of one or more communication criteria: providing a second recommendation to initiate a second type of communication with the potential communication participant.

In some embodiments, an electronic device includes one or more processors and memory. The memory stores one or more programs configured to be executed by the one or more processors. The one or more programs including instructions for: determining a predicted status for one or more contextual categories of a potential communication participant; in accordance with a determination that the predicted status for the one or more contextual categories satisfies a set of one or more communication criteria: providing a first recommendation to initiate a first type of communication with the potential communication participant; in accordance with a determination that the predicted status for the one or more contextual categories does not satisfy the set of one or more communication criteria: providing a second recommendation to initiate a second type of communication with the potential communication participant.

In some embodiments, an electronic device includes: means for determining a predicted status for one or more contextual categories of a potential communication participant; means for, in accordance with a determination that the predicted status for the one or more contextual categories satisfies a set of one or more communication criteria: providing a first recommendation to initiate a first type of communication with the potential communication participant; means for, in accordance with a determination that the predicted status for the one or more contextual categories does not satisfy the set of one or more communication criteria: providing a second recommendation to initiate a second type of communication with the potential communication participant.

Executable instructions for performing these functions are, optionally, included in a non-transitory computer-readable storage medium or other computer program product configured for execution by one or more processors. Executable instructions for performing these functions are, optionally, included in a transitory computer-readable storage medium or other computer program product configured for execution by one or more processors.

Thus, electronic devices are provided with faster, more efficient methods and interfaces when utilized, thereby increasing the effectiveness, efficiency, and user satisfaction with such devices. Such methods and interfaces may complement or replace other methods for utilizing the electronic device.

DESCRIPTION OF THE FIGURES

For a better understanding of the various described embodiments, reference should be made to the Description of Embodiments below, in conjunction with the following drawings in which like reference numerals refer to corresponding parts throughout the figures.

DESCRIPTION OF EMBODIMENTS

The following description sets forth exemplary methods, parameters, and the like. It should be recognized, however, that such description is not intended as a limitation on the scope of the present disclosure but is instead provided as a description of exemplary embodiments.

There is a need for electronic devices to utilize context information in order for a user to more efficiently operate the device. For example, without context information, the electronic device may provide notifications to a user while the user is in a meeting, thus interrupting the meeting and taking time away from the user. However, when context information is considered by the device, notifications can be provided to the user at optimal times. Utilizing context information can reduce the cognitive burden on a user who operates the electronic device, thereby enhancing productivity.

Figure 7A:
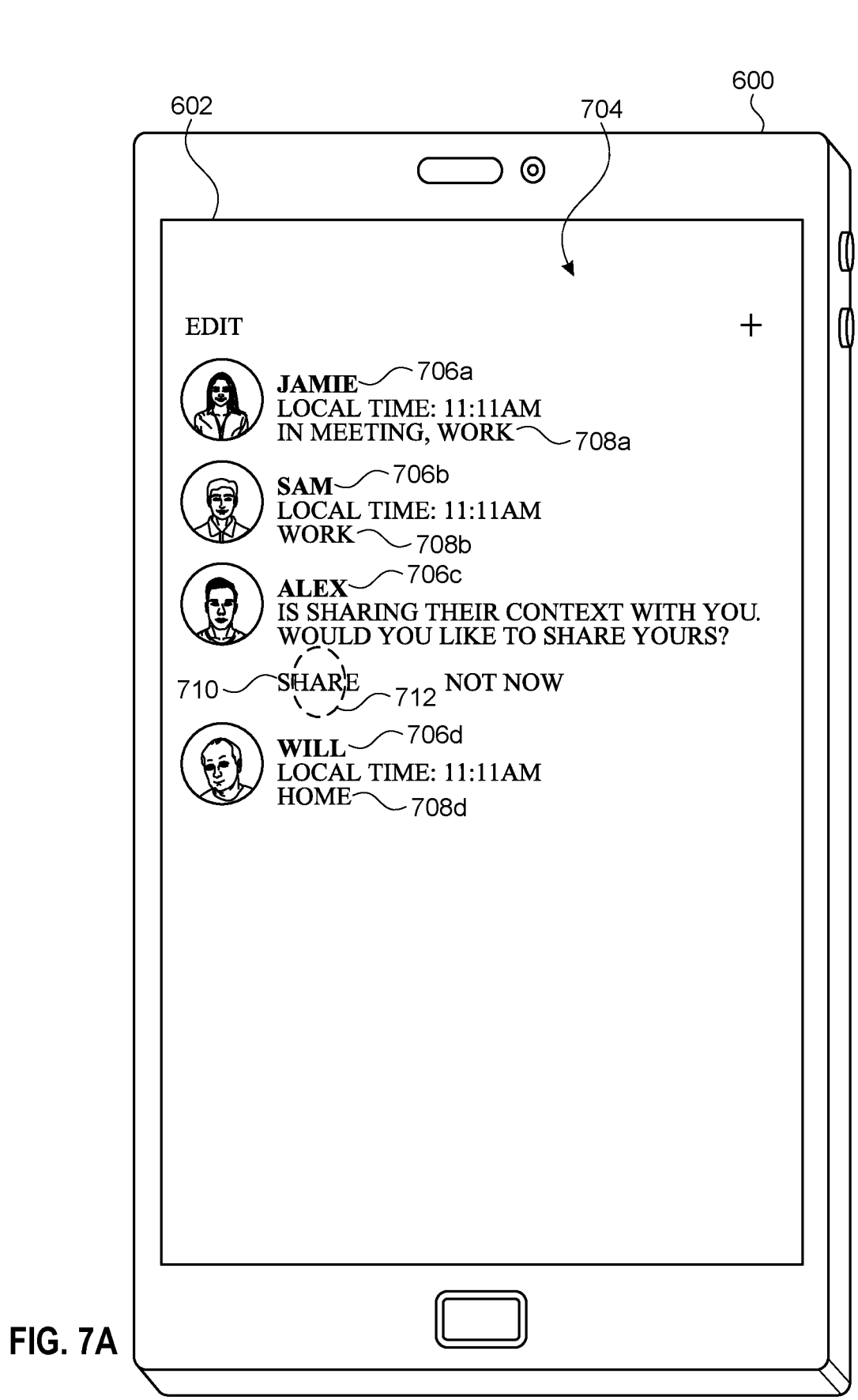
FIGS. 7A-7B illustrate exemplary user interfaces for sharing context information with an electronic device in accordance with some embodiments.
Figure 7B:
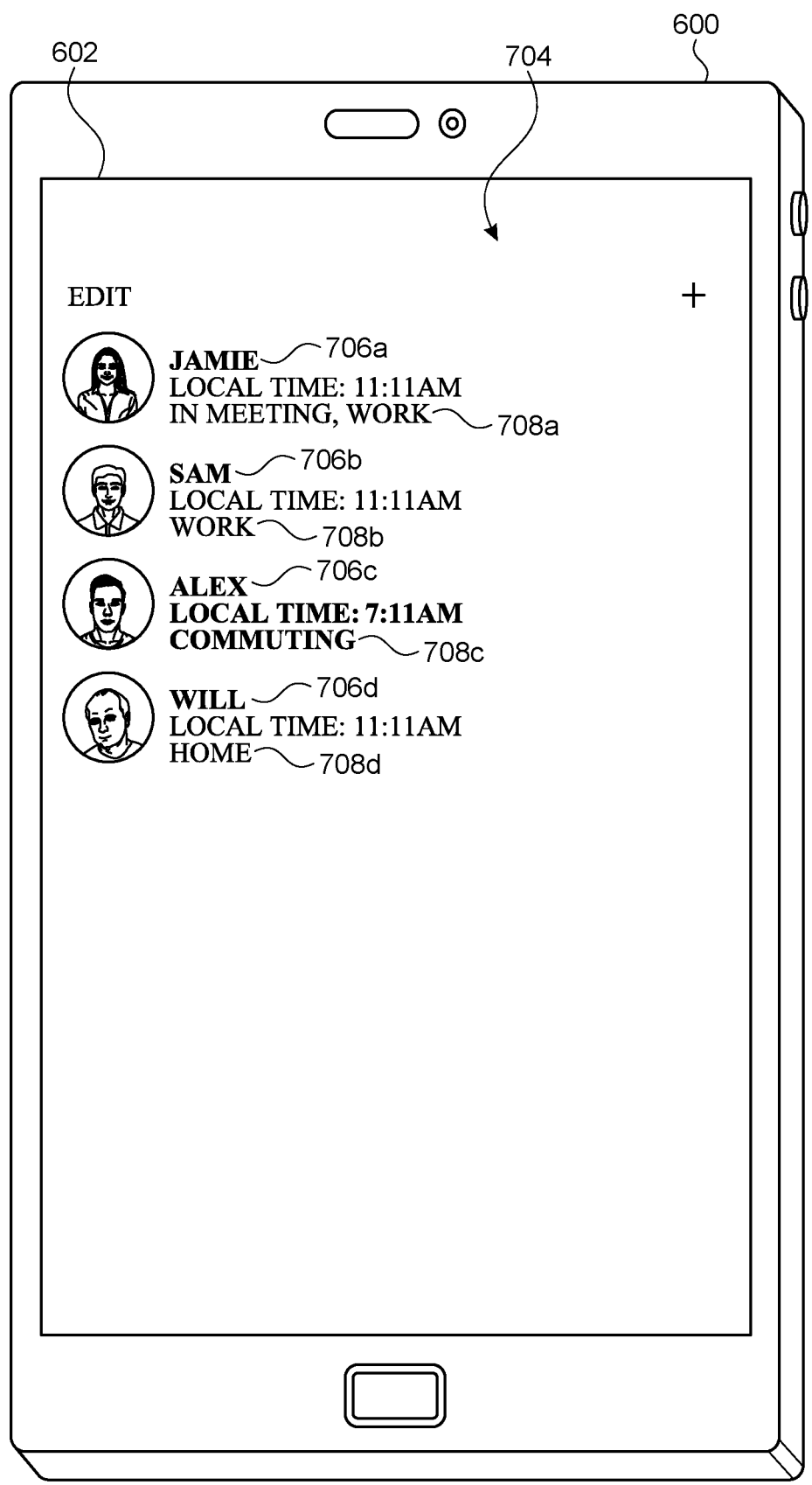
Figure 8A:
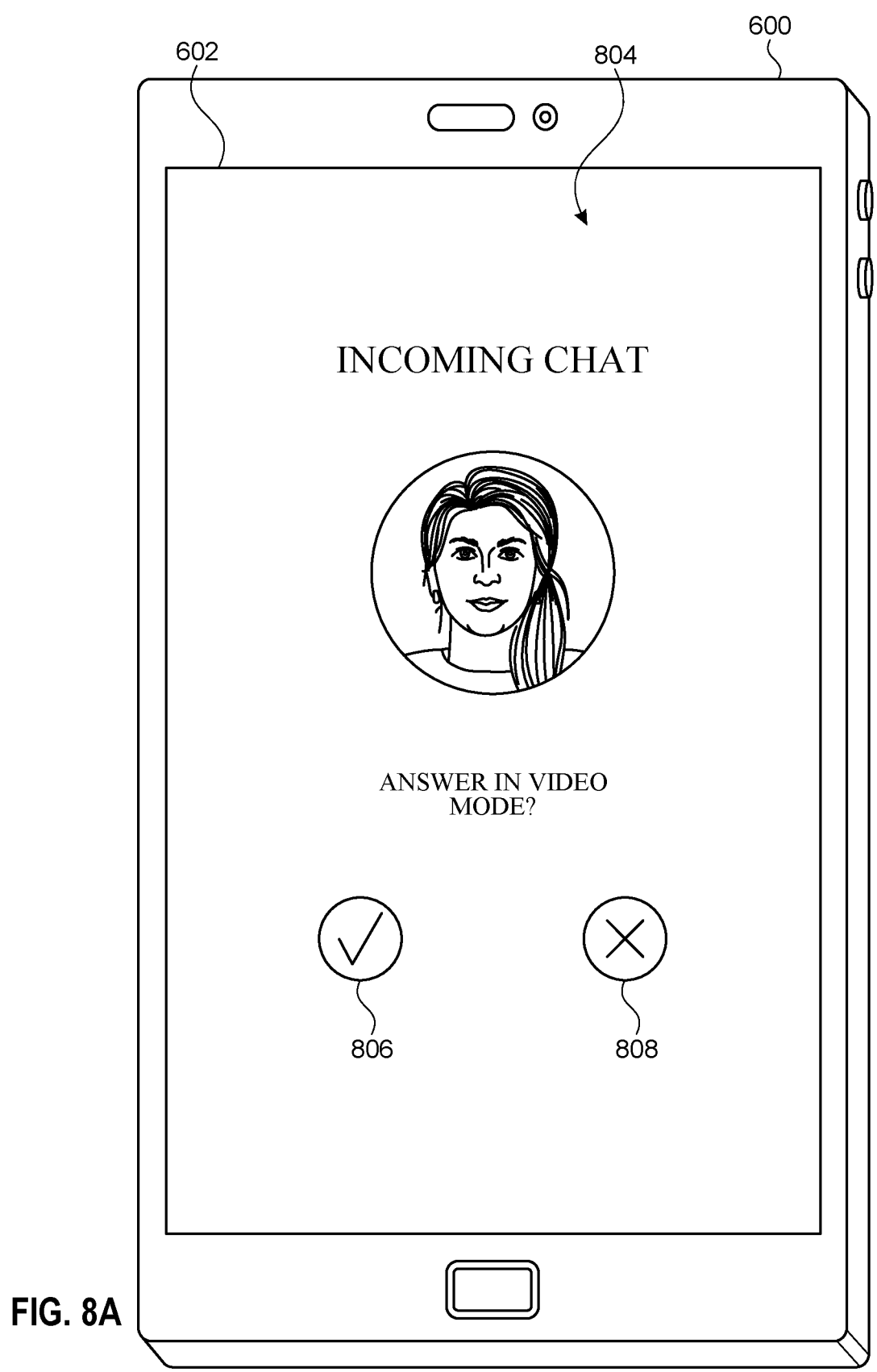
FIGS. 8A-8B illustrate exemplary user interfaces for providing notifications with an electronic device in accordance with some embodiments.
Figure 8B:
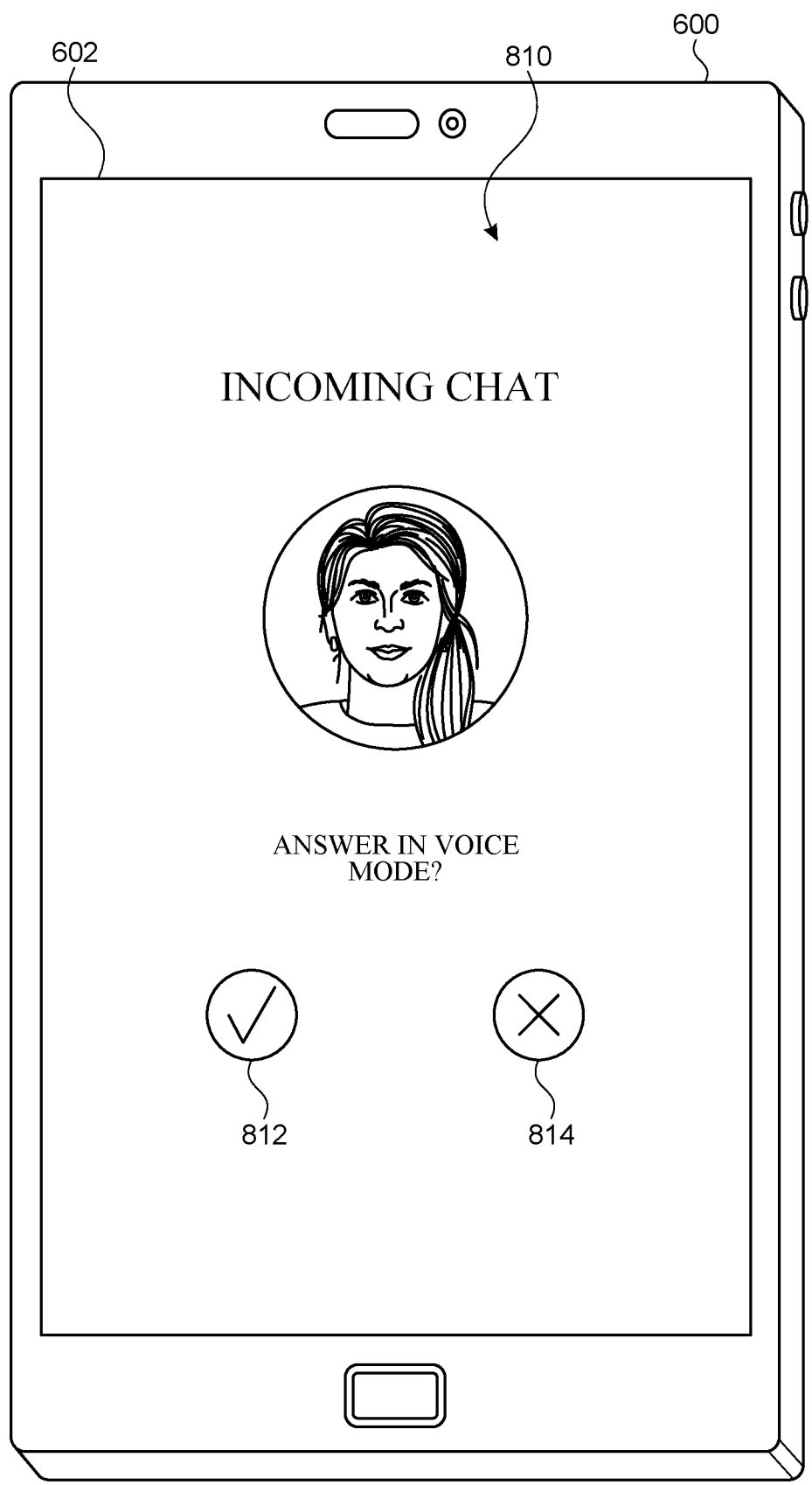
Figure 9:
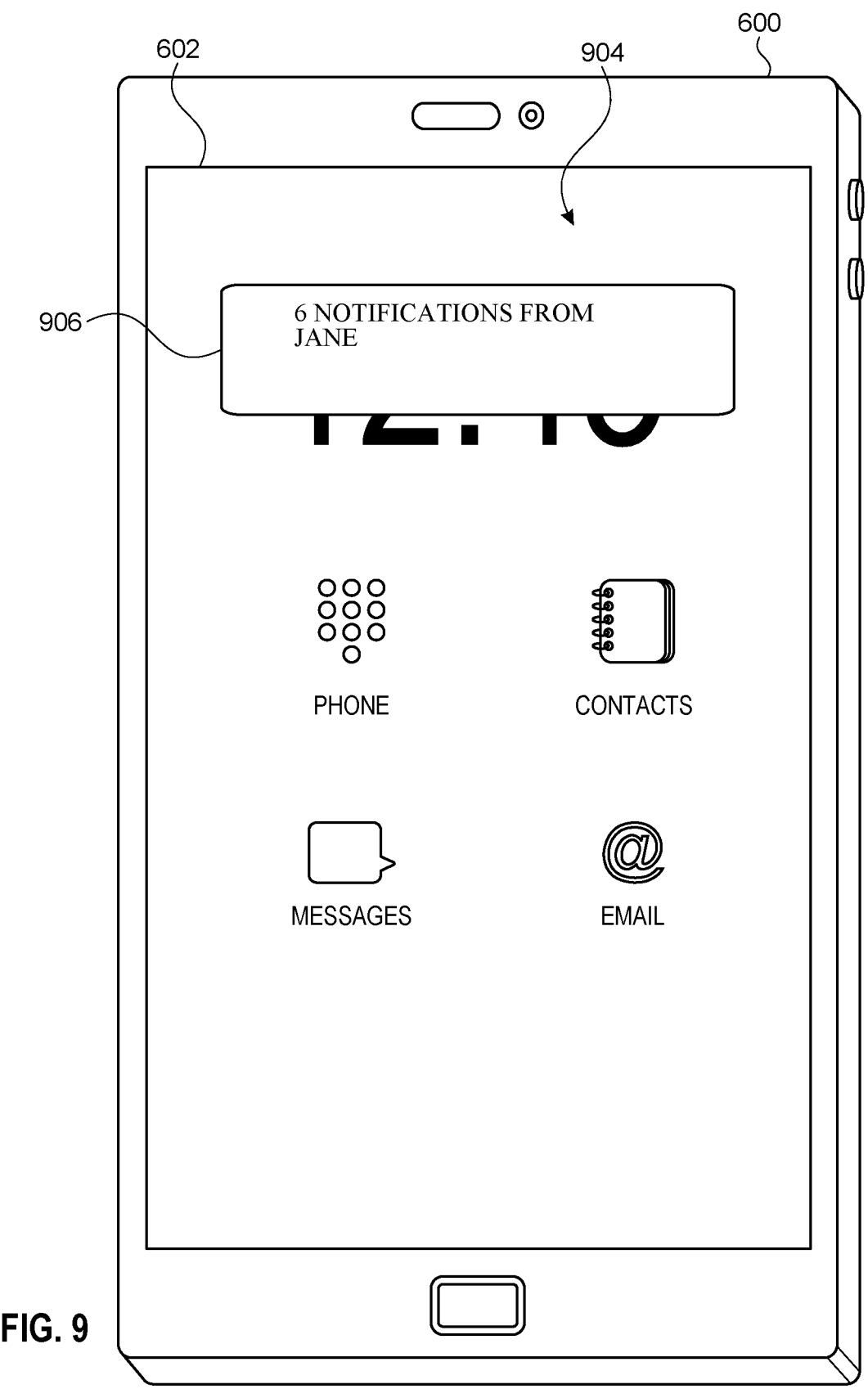
FIG. 9 illustrate exemplary user interfaces for providing notifications with an electronic device in accordance with some embodiments.
Figure 10:
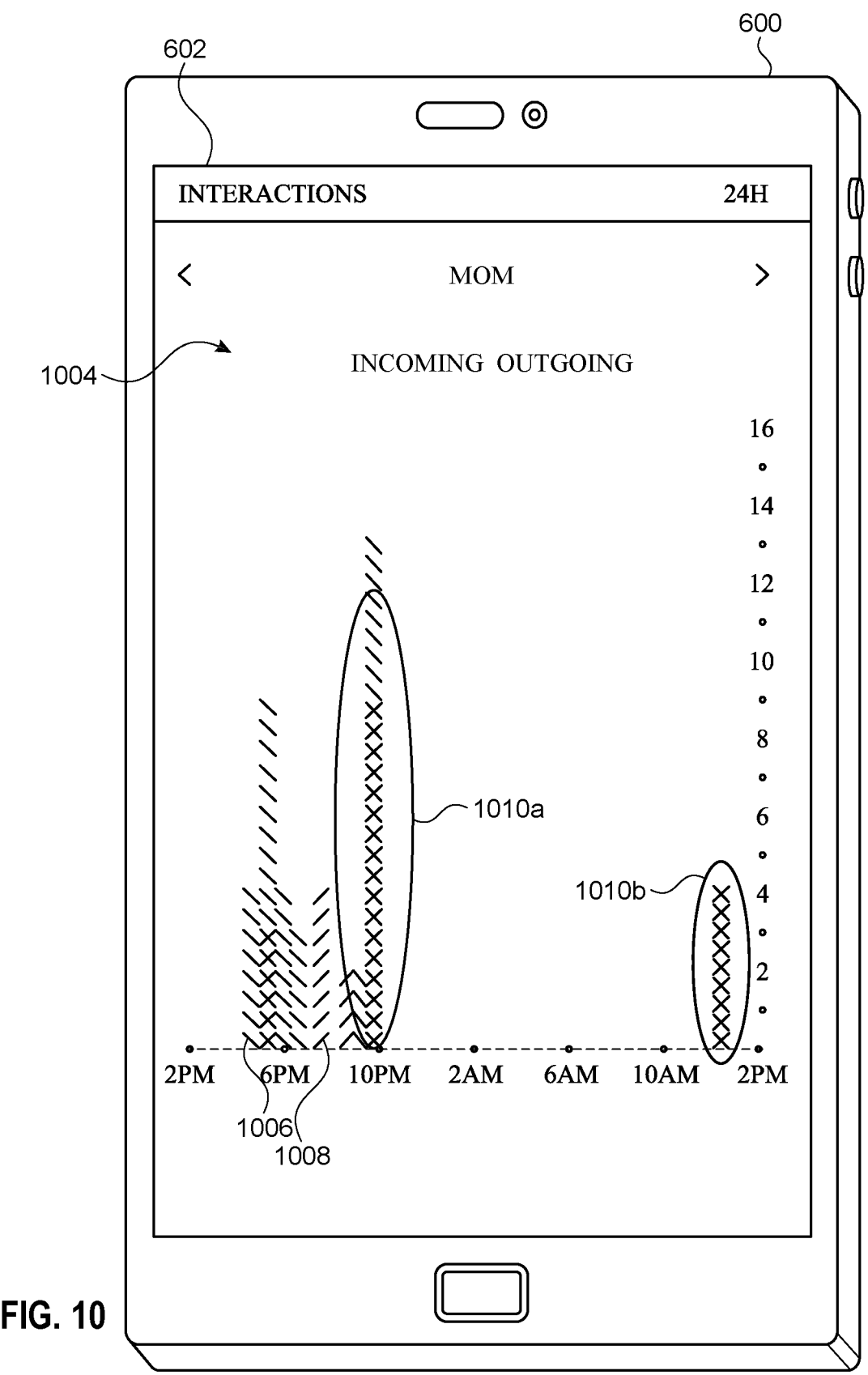
FIG. 10 illustrates an exemplary user interface for providing communication history information in accordance with some embodiments.
Figure 11A:
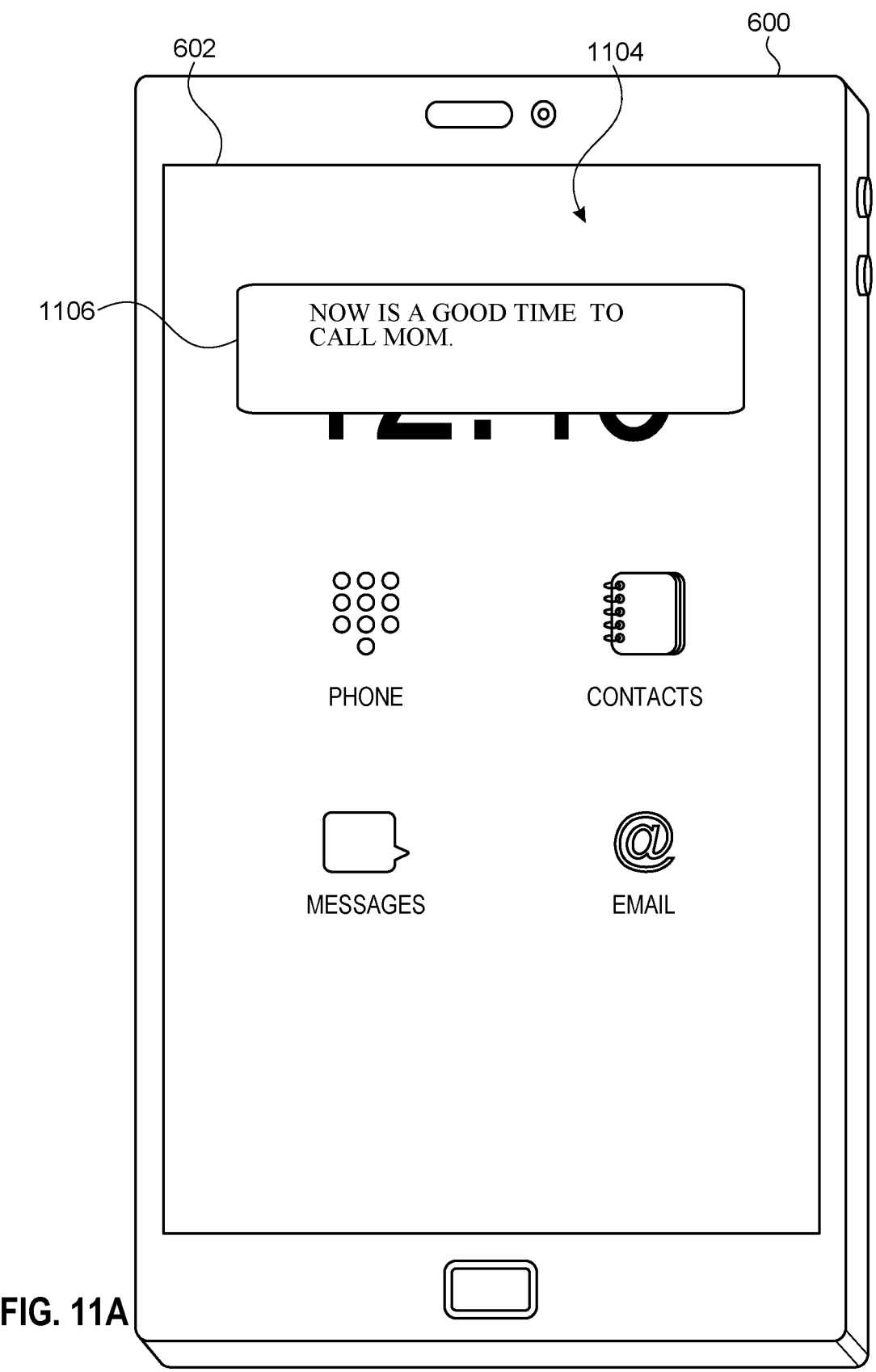
FIGS. 11A-11C illustrate exemplary user interfaces for providing communication recommendations with an electronic device in accordance with some embodiments.
Figure 11B:
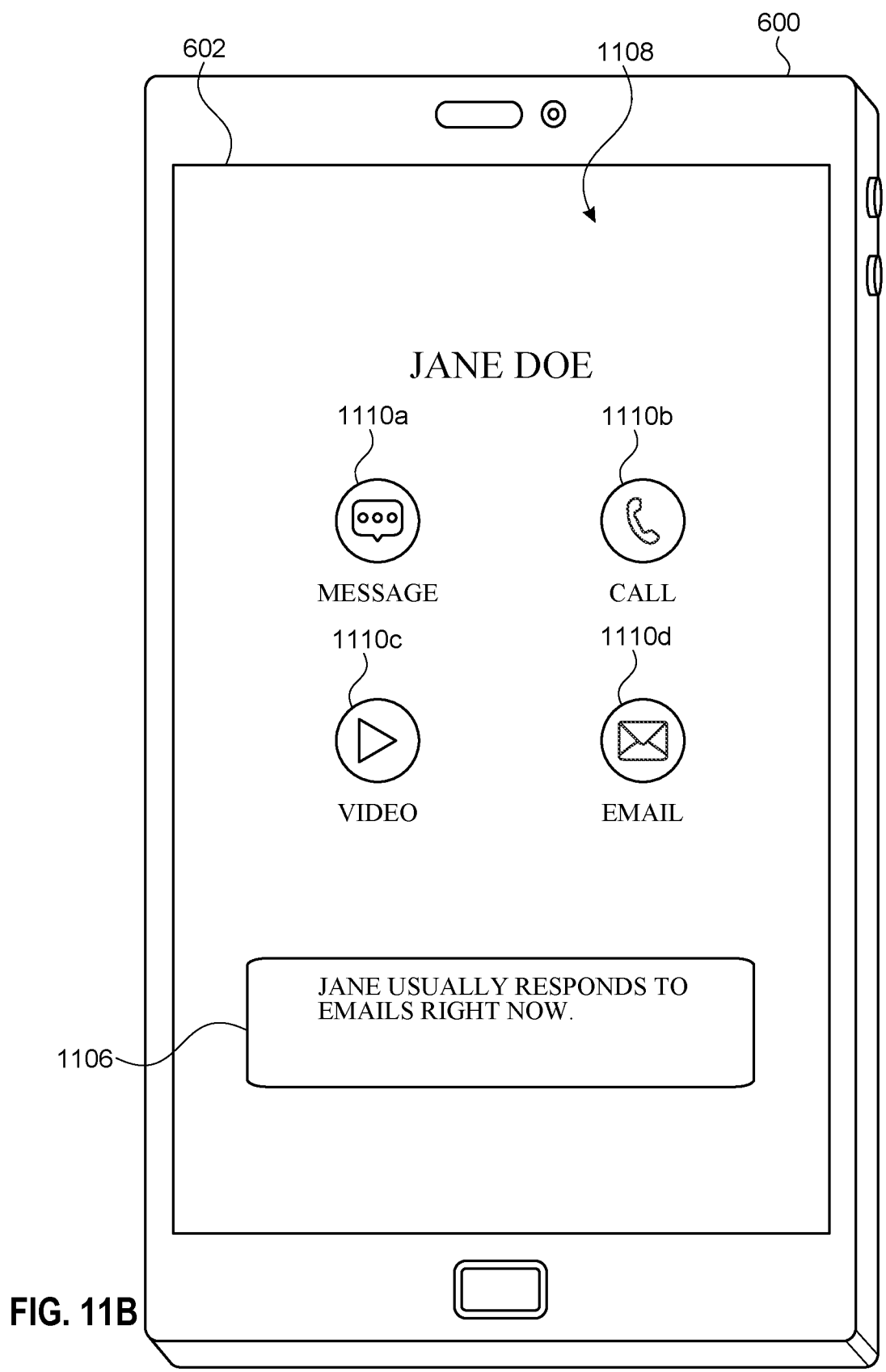
Figure 11C:
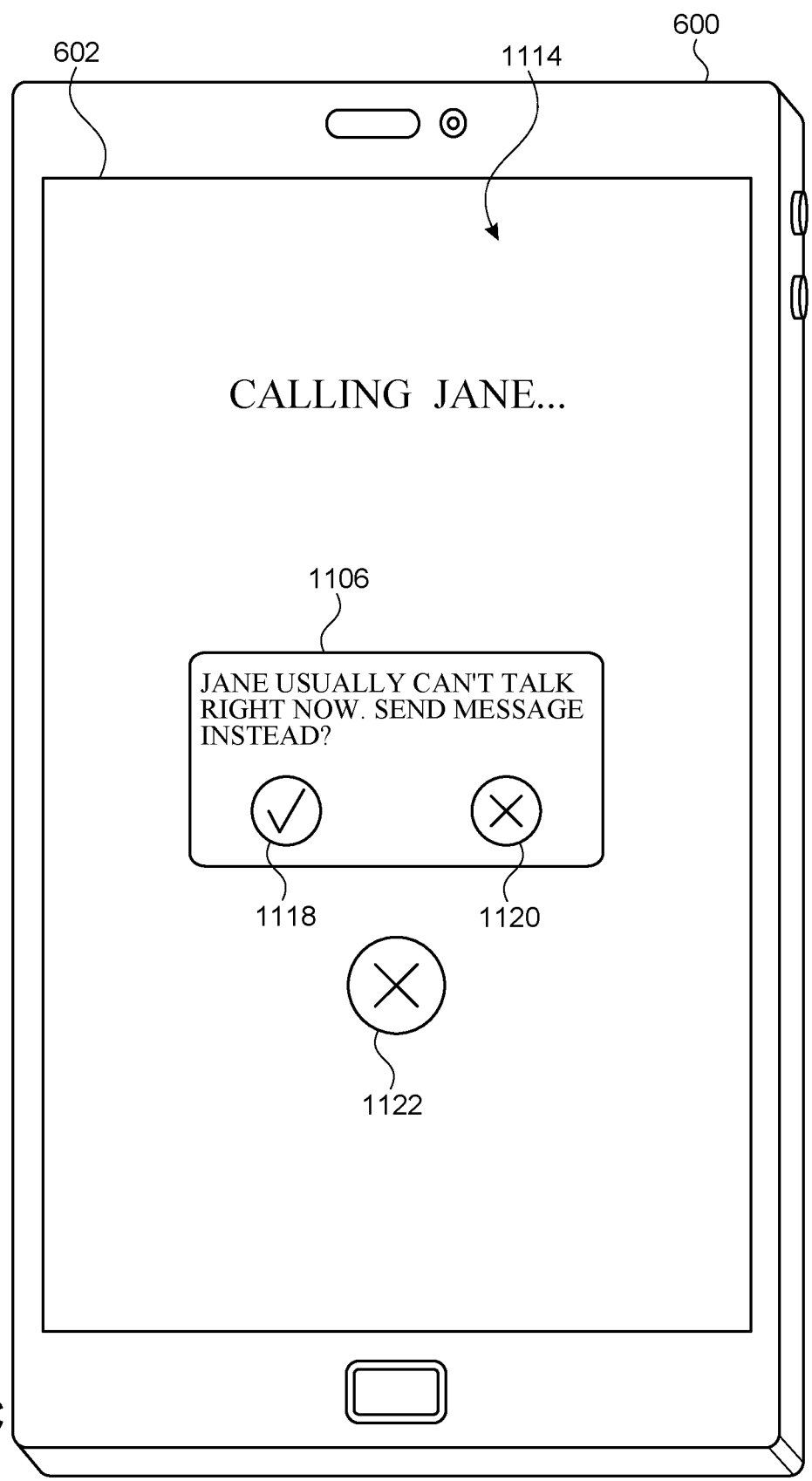
Figure 12:
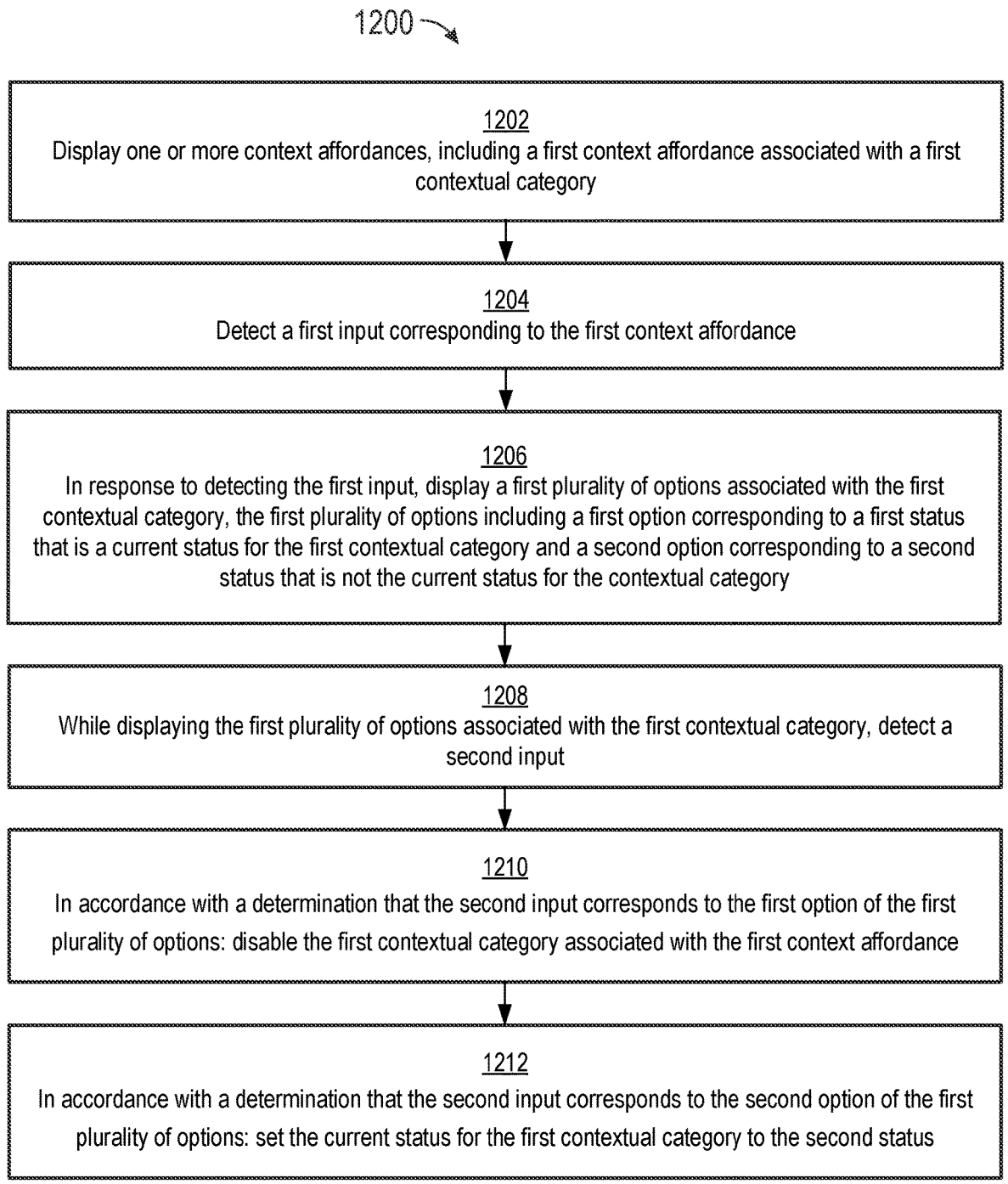
FIG. 12 is a flow diagram illustrating a method for managing context information using an electronic device in accordance with some embodiments.
Figure 13:
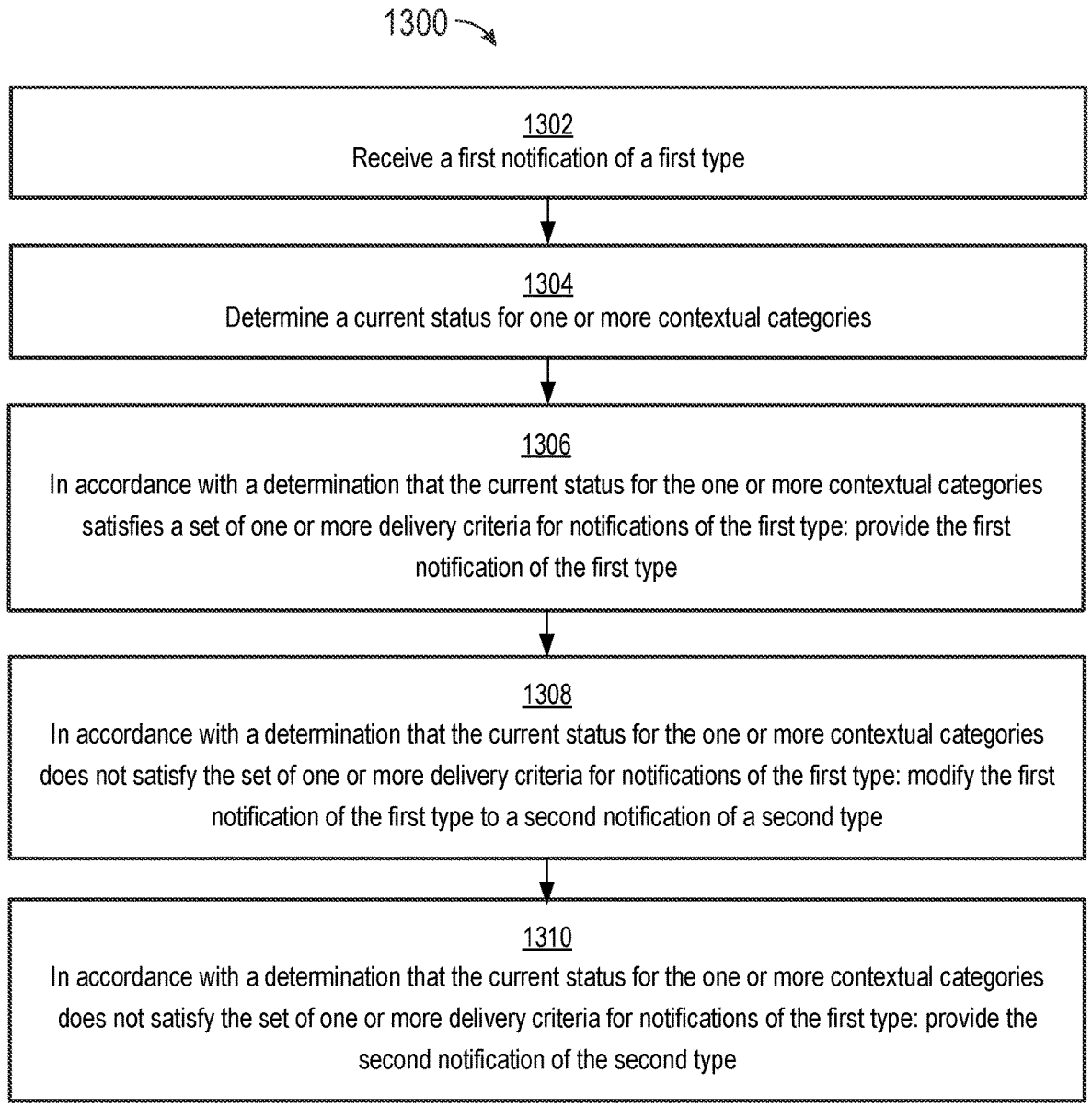
FIG. 13 is a flow diagram illustrating a method for providing notifications using an electronic device in accordance with some embodiments.
Figure 14:
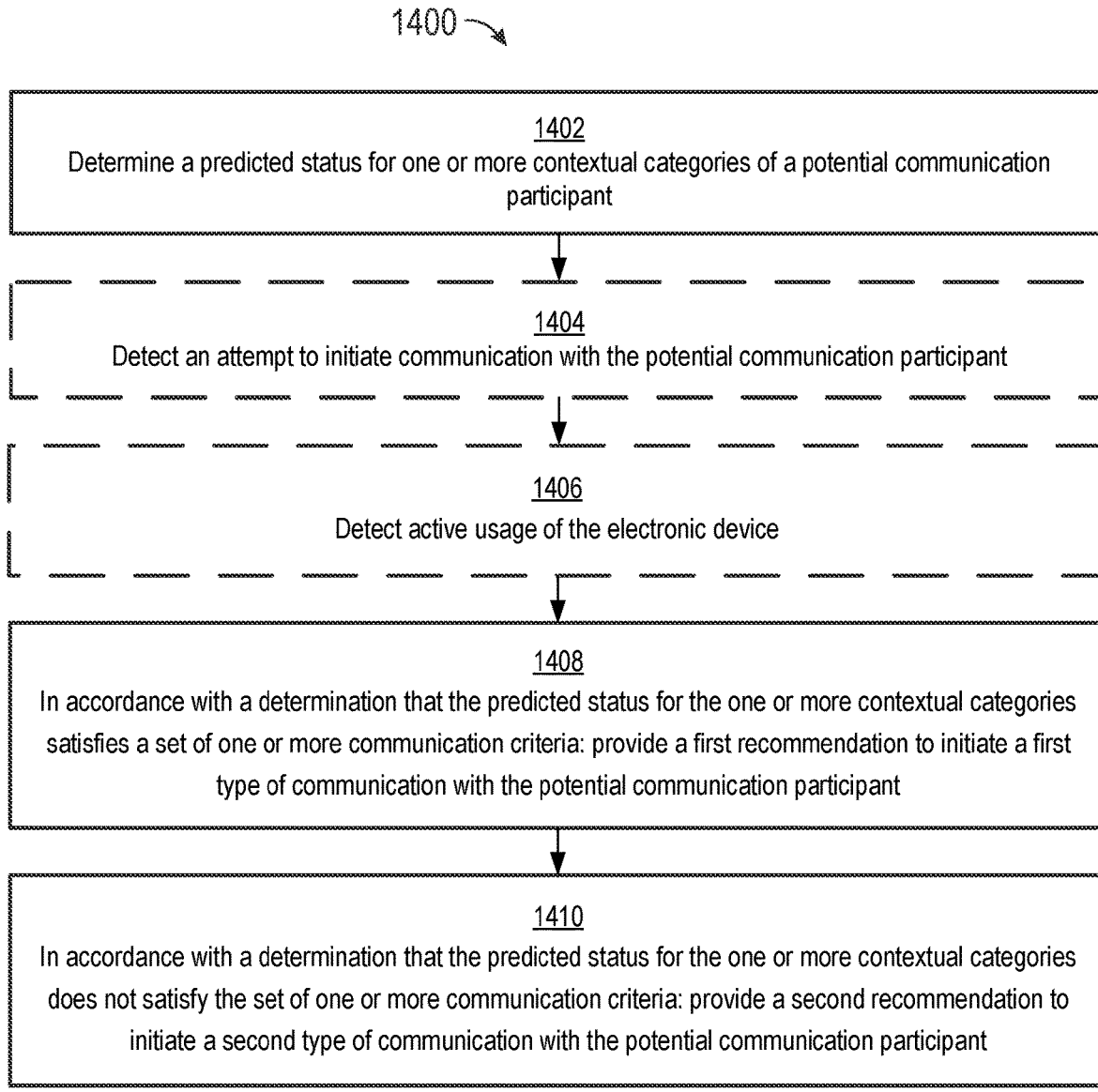
FIG. 14 is a flow diagram illustrating a method for recommending types of communication using an electronic device in accordance with some embodiments.

Below, FIGS. 1A-1B, 2, 3, 4A-4B, and 5A-5B provide a description of exemplary devices that utilize context information. FIGS. 6A-6E illustrate exemplary user interfaces for managing context information. FIGS. 7A-7B illustrate exemplary user interfaces for sharing context information. FIGS. 8A-8B and 9 illustrate exemplary user interfaces with notifications modified based on context information. FIG. 10 illustrates an example of historical communication information. FIGS. 11A-11C illustrate exemplary user interfaces for recommending types of communication. FIG. 12 is a flow diagram illustrating methods of managing context information, in accordance with some embodiments. FIG. 13 is a flow diagram illustrating methods of providing notifications, in accordance with some embodiments. FIG. 14 is a flow diagram illustrating methods of recommending a type of communication, in accordance with some embodiments. The user interfaces in FIGS. 6A-11C, are used to illustrate the processes described below, including the processes in FIGS. 12-14.

Although the following description uses terms "first," "second," etc. to describe various elements, these elements should not be limited by the terms. These terms are only used to distinguish one element from another. For example, a first touch could be termed a second touch, and, similarly, a second touch could be termed a first touch, without departing from the scope of the various described embodiments. The first touch and the second touch are both touches, but they are not the same touch.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

Embodiments of electronic devices, user interfaces for such devices, and associated processes for using such devices are described. In some embodiments, the device is a portable communications device, such as a mobile telephone, that also contains other functions, such as PDA and/or music player functions. Exemplary embodiments of portable multifunction devices include, without limitation, the iPhone®, iPod Touch®, and iPad® devices from Apple Inc. of Cupertino, California. Other portable electronic devices, such as laptops or tablet computers with touch-sensitive surfaces (e.g., touch screen displays and/or touchpads), are, optionally, used. It should also be understood that, in some embodiments, the device is not a portable communications device, but is a desktop computer with a touch-sensitive surface (e.g., a touch screen display and/or a touchpad).

In the discussion that follows, an electronic device that includes a display and a touch-sensitive surface is described. It should be understood, however, that the electronic device optionally includes one or more other physical user-interface devices, such as a physical keyboard, a mouse, and/or a joystick.

The device typically supports a variety of applications, such as one or more of the following: a drawing application, a presentation application, a word processing application, a website creation application, a disk authoring application, a spreadsheet application, a gaming application, a telephone application, a video conferencing application, an e-mail application, an instant messaging application, a workout support application, a photo management application, a digital camera application, a digital video camera application, a web browsing application, a digital music player application, and/or a digital video player application.

The various applications that are executed on the device optionally use at least one common physical user-interface device, such as the touch-sensitive surface. One or more functions of the touch-sensitive surface as well as corresponding information displayed on the device are, optionally, adjusted and/or varied from one application to the next and/or within a respective application. In this way, a common physical architecture (such as the touch-sensitive surface) of the device optionally supports the variety of applications with user interfaces that are intuitive and transparent to the user.

Figure 1A:
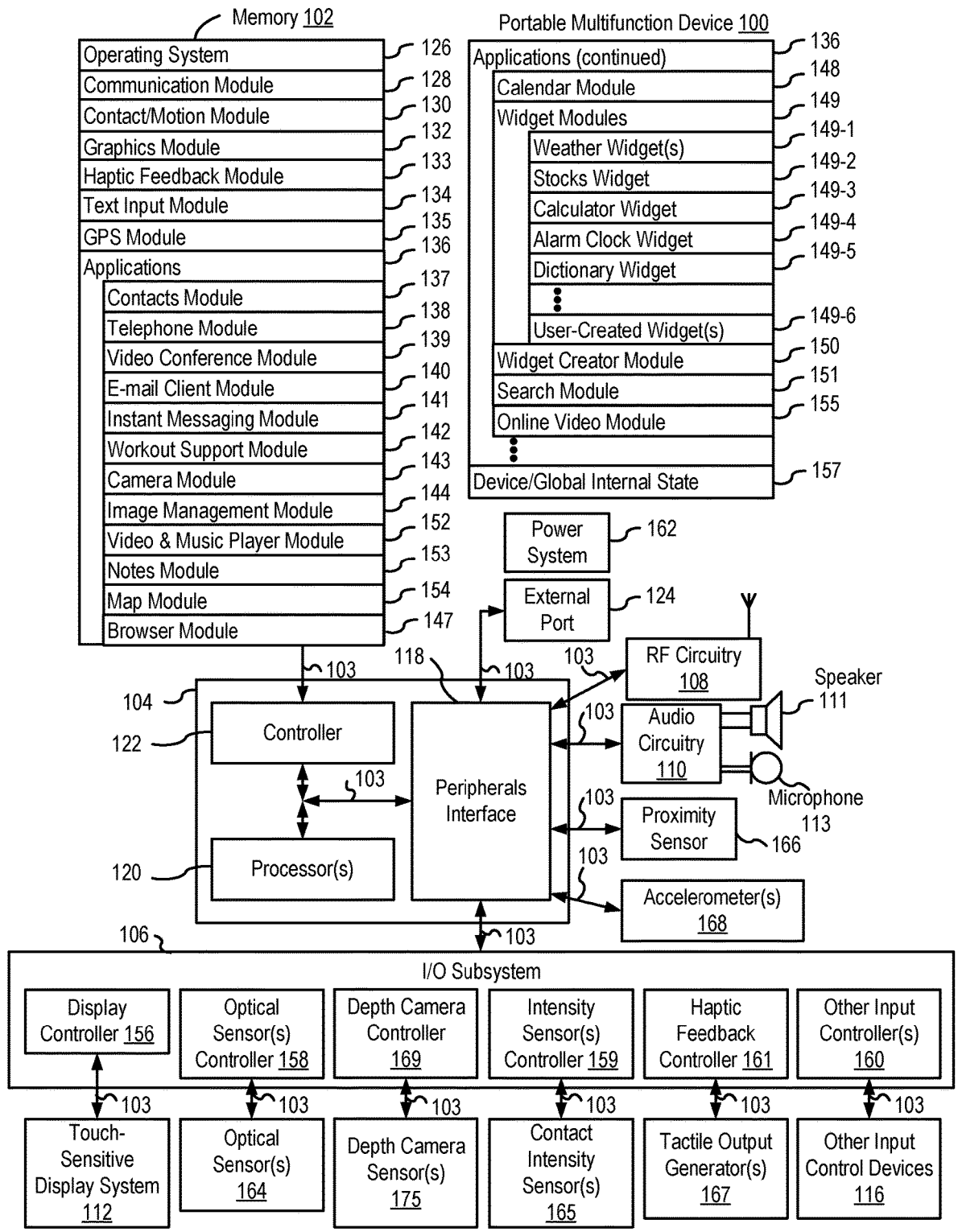
FIG. 1A is a block diagram illustrating a portable multifunction device with a touch-sensitive display in accordance with some embodiments.

Attention is now directed toward embodiments of portable devices with touch-sensitive displays. FIG. 1A is a block diagram illustrating portable multifunction device 100 with touch-sensitive display system 112 in accordance with some embodiments. Touch-sensitive display 112 is sometimes called a "touch screen" for convenience and is sometimes known as or called a "touch-sensitive display system." Device 100 includes memory 102 (which optionally includes one or more computer-readable storage mediums), memory controller 122, one or more processing units (CPUs) 120, peripherals interface 118, RF circuitry 108, audio circuitry 110, speaker 111, microphone 113, input/output (I/O) subsystem 106, other input control devices 116, and external port 124. Device 100 optionally includes one or more optical sensors 164. Device 100 optionally includes one or more contact intensity sensors 165 for detecting intensity of contacts on device 100 (e.g., a touch-sensitive surface such as touch-sensitive display system 112 of device 100). Device 100 optionally includes one or more tactile output generators 167 for generating tactile outputs on device 100 (e.g., generating tactile outputs on a touch-sensitive surface such as touch-sensitive display system 112 of device 100 or touchpad 355 of device 300). These components optionally communicate over one or more communication buses or signal lines 103.

As used in the specification and claims, the term "intensity" of a contact on a touch-sensitive surface refers to the force or pressure (force per unit area) of a contact (e.g., a finger contact) on the touch-sensitive surface, or to a substitute (proxy) for the force or pressure of a contact on the touch-sensitive surface. The intensity of a contact has a range of values that includes at least four distinct values and more typically includes hundreds of distinct values (e.g., at least 256). Intensity of a contact is, optionally, determined (or measured) using various approaches and various sensors or combinations of sensors. For example, one or more force sensors underneath or adjacent to the touch-sensitive surface are, optionally, used to measure force at various points on the touch-sensitive surface. In some implementations, force measurements from multiple force sensors are combined (e.g., a weighted average) to determine an estimated force of a contact. Similarly, a pressure-sensitive tip of a stylus is, optionally, used to determine a pressure of the stylus on the touch-sensitive surface. Alternatively, the size of the contact area detected on the touch-sensitive surface and/or changes thereto, the capacitance of the touch-sensitive surface proximate to the contact and/or changes thereto, and/or the resistance of the touch-sensitive surface proximate to the contact and/or changes thereto are, optionally, used as a substitute for the force or pressure of the contact on the touch-sensitive surface. In some implementations, the substitute measurements for contact force or pressure are used directly to determine whether an intensity threshold has been exceeded (e.g., the intensity threshold is described in units corresponding to the substitute measurements). In some implementations, the substitute measurements for contact force or pressure are converted to an estimated force or pressure, and the estimated force or pressure is used to determine whether an intensity threshold has been exceeded (e.g., the intensity threshold is a pressure threshold measured in units of pressure). Using the intensity of a contact as an attribute of a user input allows for user access to additional device functionality that may otherwise not be accessible by the user on a reduced-size device with limited real estate for displaying affordances (e.g., on a touch-sensitive display) and/or receiving user input (e.g., via a touch-sensitive display, a touch-sensitive surface, or a physical/mechanical control such as a knob or a button).

As used in the specification and claims, the term "tactile output" refers to physical displacement of a device relative to a previous position of the device, physical displacement of a component (e.g., a touch-sensitive surface) of a device relative to another component (e.g., housing) of the device, or displacement of the component relative to a center of mass of the device that will be detected by a user with the user's sense of touch. For example, in situations where the device or the component of the device is in contact with a surface of a user that is sensitive to touch (e.g., a finger, palm, or other part of a user's hand), the tactile output generated by the physical displacement will be interpreted by the user as a tactile sensation corresponding to a perceived change in physical characteristics of the device or the component of the device. For example, movement of a touch-sensitive surface (e.g., a touch-sensitive display or trackpad) is, optionally, interpreted by the user as a "down click" or "up click" of a physical actuator button. In some cases, a user will feel a tactile sensation such as an "down click" or "up click" even when there is no movement of a physical actuator button associated with the touch-sensitive surface that is physically pressed (e.g., displaced) by the user's movements. As another example, movement of the touch-sensitive surface is, optionally, interpreted or sensed by the user as "roughness" of the touch-sensitive surface, even when there is no change in smoothness of the touch-sensitive surface. While such interpretations of touch by a user will be subject to the individualized sensory perceptions of the user, there are many sensory perceptions of touch that are common to a large majority of users. Thus, when a tactile output is described as corresponding to a particular sensory perception of a user (e.g., an "up click," a "down click," "roughness"), unless otherwise stated, the generated tactile output corresponds to physical displacement of the device or a component thereof that will generate the described sensory perception for a typical (or average) user.

It should be appreciated that device 100 is only one example of a portable multifunction device, and that device 100 optionally has more or fewer components than shown, optionally combines two or more components, or optionally has a different configuration or arrangement of the components. The various components shown in FIG. 1A are implemented in hardware, software, or a combination of both hardware and software, including one or more signal processing and/or application-specific integrated circuits.

Memory 102 optionally includes high-speed random access memory and optionally also includes non-volatile memory, such as one or more magnetic disk storage devices, flash memory devices, or other non-volatile solid-state memory devices. Memory controller 122 optionally controls access to memory 102 by other components of device 100.

Peripherals interface 118 can be used to couple input and output peripherals of the device to CPU 120 and memory 102. The one or more processors 120 run or execute various software programs and/or sets of instructions stored in memory 102 to perform various functions for device 100 and to process data. In some embodiments, peripherals interface 118, CPU 120, and memory controller 122 are, optionally, implemented on a single chip, such as chip 104. In some other embodiments, they are, optionally, implemented on separate chips.

RF (radio frequency) circuitry 108 receives and sends RF signals, also called electromagnetic signals. RF circuitry 108 converts electrical signals to/from electromagnetic signals and communicates with communications networks and other communications devices via the electromagnetic signals. RF circuitry 108 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 108 optionally communicates with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The RF circuitry 108 optionally includes well-known circuitry for detecting near field communication (NFC) fields, such as by a short-range communication radio. The wireless communication optionally uses any of a plurality of communications standards, protocols, and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Bluetooth Low Energy (BTLE), Wireless Fidelity (Wi-Fi) (e.g., IEEE 802.11a, IEEE 802.11b, IEEE 802.11g, IEEE 802.11n, and/or IEEE 802.11ac), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

Audio circuitry 110, speaker 111, and microphone 113 provide an audio interface between a user and device 100. Audio circuitry 110 receives audio data from peripherals interface 118, converts the audio data to an electrical signal, and transmits the electrical signal to speaker 111. Speaker 111 converts the electrical signal to human-audible sound waves. Audio circuitry 110 also receives electrical signals converted by microphone 113 from sound waves. Audio circuitry 110 converts the electrical signal to audio data and transmits the audio data to peripherals interface 118 for processing. Audio data is, optionally, retrieved from and/or transmitted to memory 102 and/or RF circuitry 108 by peripherals interface 118. In some embodiments, audio circuitry 110 also includes a headset jack (e.g., 212, FIG. 2). The headset jack provides an interface between audio circuitry 110 and removable audio input/output peripherals, such as output-only headphones or a headset with both output (e.g., a headphone for one or both ears) and input (e.g., a microphone).

I/O subsystem 106 couples input/output peripherals on device 100, such as touch screen 112 and other input control devices 116, to peripherals interface 118. I/O subsystem 106 optionally includes display controller 156, optical sensor controller 158, depth camera controller 169, intensity sensor controller 159, haptic feedback controller 161, and one or more input controllers 160 for other input or control devices. The one or more input controllers 160 receive/send electrical signals from/to other input control devices 116. The other input control devices 116 optionally include physical buttons (e.g., push buttons, rocker buttons, etc.), dials, slider switches, joysticks, click wheels, and so forth. In some alternate embodiments, input controller(s) 160 are, optionally, coupled to any (or none) of the following: a keyboard, an infrared port, a USB port, and a pointer device such as a mouse. The one or more buttons (e.g., 208, FIG. 2) optionally include an up/down button for volume control of speaker 111 and/or microphone 113. The one or more buttons optionally include a push button (e.g., 206, FIG. 2).

A quick press of the push button optionally disengages a lock of touch screen 112 or optionally begins a process that uses gestures on the touch screen to unlock the device, as described in U.S. patent application Ser. No. 11/322,549, "Unlocking a Device by Performing Gestures on an Unlock Image," filed Dec. 23, 2005, U.S. Pat. No. 7,657,849, which is hereby incorporated by reference in its entirety. A longer press of the push button (e.g., 206) optionally turns power to device 100 on or off. The functionality of one or more of the buttons are, optionally, user-customizable. Touch screen 112 is used to implement virtual or soft buttons and one or more soft keyboards.

Touch-sensitive display 112 provides an input interface and an output interface between the device and a user. Display controller 156 receives and/or sends electrical signals from/to touch screen 112. Touch screen 112 displays visual output to the user. The visual output optionally includes graphics, text, icons, video, and any combination thereof (collectively termed "graphics"). In some embodiments, some or all of the visual output optionally corresponds to user-interface objects.

Touch screen 112 has a touch-sensitive surface, sensor, or set of sensors that accepts input from the user based on haptic and/or tactile contact. Touch screen 112 and display controller 156 (along with any associated modules and/or sets of instructions in memory 102) detect contact (and any movement or breaking of the contact) on touch screen 112 and convert the detected contact into interaction with user-interface objects (e.g., one or more soft keys, icons, web pages, or images) that are displayed on touch screen 112. In an exemplary embodiment, a point of contact between touch screen 112 and the user corresponds to a finger of the user.

Touch screen 112 optionally uses LCD (liquid crystal display) technology, LPD (light emitting polymer display) technology, or LED (light emitting diode) technology, although other display technologies are used in other embodiments. Touch screen 112 and display controller 156 optionally detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with touch screen 112. In an exemplary embodiment, projected mutual capacitance sensing technology is used, such as that found in the iPhone® and iPod Touch® from Apple Inc. of Cupertino, California.

A touch-sensitive display in some embodiments of touch screen 112 is, optionally, analogous to the multi-touch sensitive touchpads described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1, each of which is hereby incorporated by reference in its entirety. However, touch screen 112 displays visual output from device 100, whereas touch-sensitive touchpads do not provide visual output.

A touch-sensitive display in some embodiments of touch screen 112 is described in the following applications: (1) U.S. patent application Ser. No. 11/381,313, "Multipoint Touch Surface Controller," filed May 2, 2006; (2) U.S. patent application Ser. No. 10/840,862, "Multipoint Touchscreen," filed May 6, 2004; (3) U.S. patent application Ser. No. 10/903,964, "Gestures For Touch Sensitive Input Devices," filed Jul. 30, 2004; (4) U.S. patent application Ser. No. 11/048,264, "Gestures For Touch Sensitive Input Devices," filed Jan. 31, 2005; (5) U.S. patent application Ser. No. 11/038,590, "Mode-Based Graphical User Interfaces For Touch Sensitive Input Devices," filed Jan. 18, 2005; (6) U.S. patent application Ser. No. 11/228,758, "Virtual Input Device Placement On A Touch Screen User Interface," filed Sep. 16, 2005; (7) U.S. patent application Ser. No. 11/228,700, "Operation Of A Computer With A Touch Screen Interface," filed Sep. 16, 2005; (8) U.S. patent application Ser. No. 11/228,737, "Activating Virtual Keys Of A Touch-Screen Virtual Keyboard," filed Sep. 16, 2005; and (9) U.S. patent application Ser. No. 11/367,749, "Multi-Functional Hand-Held Device," filed Mar. 3, 2006. All of these applications are incorporated by reference herein in their entirety.

Touch screen 112 optionally has a video resolution in excess of 100 dpi. In some embodiments, the touch screen has a video resolution of approximately 160 dpi. The user optionally makes contact with touch screen 112 using any suitable object or appendage, such as a stylus, a finger, and so forth. In some embodiments, the user interface is designed to work primarily with finger-based contacts and gestures, which can be less precise than stylus-based input due to the larger area of contact of a finger on the touch screen. In some embodiments, the device translates the rough finger-based input into a precise pointer/cursor position or command for performing the actions desired by the user.

In some embodiments, in addition to the touch screen, device 100 optionally includes a touchpad for activating or deactivating particular functions. In some embodiments, the touchpad is a touch-sensitive area of the device that, unlike the touch screen, does not display visual output. The touchpad is, optionally, a touch-sensitive surface that is separate from touch screen 112 or an extension of the touch-sensitive surface formed by the touch screen.

Device 100 also includes power system 162 for powering the various components. Power system 162 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

Device 100 optionally also includes one or more optical sensors 164. FIG. 1A shows an optical sensor coupled to optical sensor controller 158 in I/O subsystem 106. Optical sensor 164 optionally includes charge-coupled device (CCD) or complementary metal-oxide semiconductor (CMOS) phototransistors. Optical sensor 164 receives light from the environment, projected through one or more lenses, and converts the light to data representing an image. In conjunction with imaging module 143 (also called a camera module), optical sensor 164 optionally captures still images or video. In some embodiments, an optical sensor is located on the back of device 100, opposite touch screen display 112 on the front of the device so that the touch screen display is enabled for use as a viewfinder for still and/or video image acquisition. In some embodiments, an optical sensor is located on the front of the device so that the user's image is, optionally, obtained for video conferencing while the user views the other video conference participants on the touch screen display. In some embodiments, the position of optical sensor 164 can be changed by the user (e.g., by rotating the lens and the sensor in the device housing) so that a single optical sensor 164 is used along with the touch screen display for both video conferencing and still and/or video image acquisition.

Device 100 optionally also includes one or more depth camera sensors 175. FIG. 1A shows a depth camera sensor coupled to depth camera controller 169 in I/O subsystem 106. Depth camera sensor 175 receives data from the environment to create a three dimensional model of an object (e.g., a face) within a scene from a viewpoint (e.g., a depth camera sensor). In some embodiments, in conjunction with imaging module 143 (also called a camera module), depth camera sensor 175 is optionally used to determine a depth map of different portions of an image captured by the imaging module 143. In some embodiments, a depth camera sensor is located on the front of device 100 so that the user's image with depth information is, optionally, obtained for video conferencing while the user views the other video conference participants on the touch screen display and to capture selfies with depth map data. In some embodiments, the depth camera sensor 175 is located on the back of device, or on the back and the front of the device 100. In some embodiments, the position of depth camera sensor 175 can be changed by the user (e.g., by rotating the lens and the sensor in the device housing) so that a depth camera sensor 175 is used along with the touch screen display for both video conferencing and still and/or video image acquisition.

Device 100 optionally also includes one or more contact intensity sensors 165. FIG. 1A shows a contact intensity sensor coupled to intensity sensor controller 159 in I/O subsystem 106. Contact intensity sensor 165 optionally includes one or more piezoresistive strain gauges, capacitive force sensors, electric force sensors, piezoelectric force sensors, optical force sensors, capacitive touch-sensitive surfaces, or other intensity sensors (e.g., sensors used to measure the force (or pressure) of a contact on a touch-sensitive surface). Contact intensity sensor 165 receives contact intensity information (e.g., pressure information or a proxy for pressure information) from the environment. In some embodiments, at least one contact intensity sensor is collocated with, or proximate to, a touch-sensitive surface (e.g., touch-sensitive display system 112). In some embodiments, at least one contact intensity sensor is located on the back of device 100, opposite touch screen display 112, which is located on the front of device 100.

Device 100 optionally also includes one or more proximity sensors 166. FIG. 1A shows proximity sensor 166 coupled to peripherals interface 118. Alternately, proximity sensor 166 is, optionally, coupled to input controller 160 in I/O subsystem 106. Proximity sensor 166 optionally performs as described in U.S. patent application Ser. No. 11/241,839, "Proximity Detector In Handheld Device"; Ser. No. 11/240,788, "Proximity Detector In Handheld Device"; Ser. No. 11/620,702, "Using Ambient Light Sensor To Augment Proximity Sensor Output"; Ser. No. 11/586,862, "Automated Response To And Sensing Of User Activity In Portable Devices"; and Ser. No. 11/638,251, "Methods And Systems For Automatic Configuration Of Peripherals," which are hereby incorporated by reference in their entirety. In some embodiments, the proximity sensor turns off and disables touch screen 112 when the multifunction device is placed near the user's ear (e.g., when the user is making a phone call).

Device 100 optionally also includes one or more tactile output generators 167. FIG. 1A shows a tactile output generator coupled to haptic feedback controller 161 in I/O subsystem 106. Tactile output generator 167 optionally includes one or more electroacoustic devices such as speakers or other audio components and/or electromechanical devices that convert energy into linear motion such as a motor, solenoid, electroactive polymer, piezoelectric actuator, electrostatic actuator, or other tactile output generating component (e.g., a component that converts electrical signals into tactile outputs on the device). Contact intensity sensor 165 receives tactile feedback generation instructions from haptic feedback module 133 and generates tactile outputs on device 100 that are capable of being sensed by a user of device 100. In some embodiments, at least one tactile output generator is collocated with, or proximate to, a touch-sensitive surface (e.g., touch-sensitive display system 112) and, optionally, generates a tactile output by moving the touch-sensitive surface vertically (e.g., in/out of a surface of device 100) or laterally (e.g., back and forth in the same plane as a surface of device 100). In some embodiments, at least one tactile output generator sensor is located on the back of device 100, opposite touch screen display 112, which is located on the front of device 100.

Device 100 optionally also includes one or more accelerometers 168. FIG. 1A shows accelerometer 168 coupled to peripherals interface 118. Alternately, accelerometer 168 is, optionally, coupled to an input controller 160 in I/O subsystem 106. Accelerometer 168 optionally performs as described in U.S. Patent Publication No. 20050190059, "Acceleration-based Theft Detection System for Portable Electronic Devices," and U.S. Patent Publication No. 20060017692, "Methods And Apparatuses For Operating A Portable Device Based On An Accelerometer," both of which are incorporated by reference herein in their entirety. In some embodiments, information is displayed on the touch screen display in a portrait view or a landscape view based on an analysis of data received from the one or more accelerometers. Device 100 optionally includes, in addition to accelerometer(s) 168, a magnetometer and a GPS (or GLONASS or other global navigation system) receiver for obtaining information concerning the location and orientation (e.g., portrait or landscape) of device 100.

Figure 3:
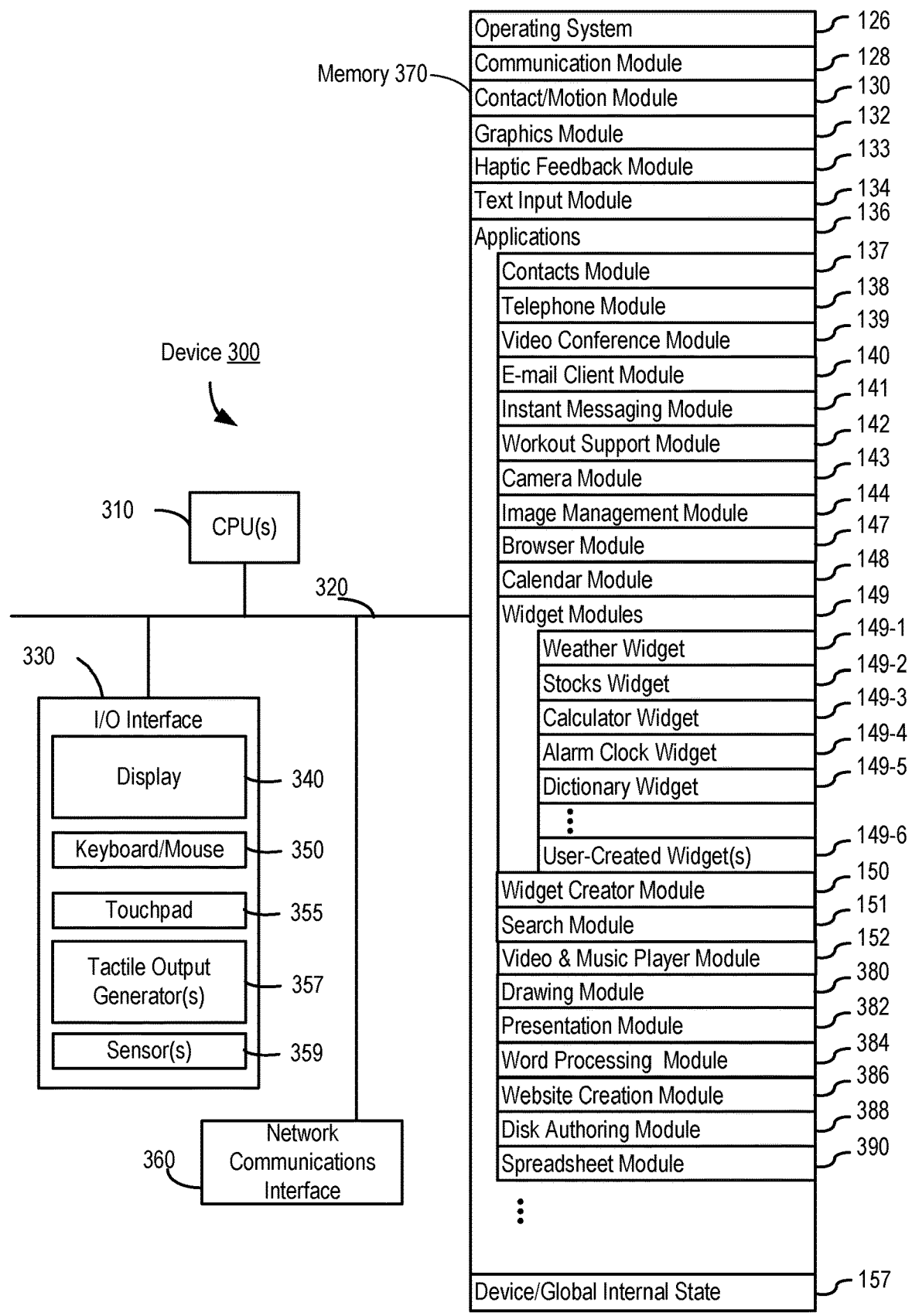
FIG. 3 is a block diagram of an exemplary multifunction device with a display and a touch-sensitive surface in accordance with some embodiments.

In some embodiments, the software components stored in memory 102 include operating system 126, communication module (or set of instructions) 128, contact/motion module (or set of instructions) 130, graphics module (or set of instructions) 132, text input module (or set of instructions) 134, Global Positioning System (GPS) module (or set of instructions) 135, and applications (or sets of instructions) 136. Furthermore, in some embodiments, memory 102 (FIG. 1A) or 370 (FIG. 3) stores device/global internal state 157, as shown in FIGS. 1A and 3. Device/global internal state 157 includes one or more of: active application state, indicating which applications, if any, are currently active; display state, indicating what applications, views or other information occupy various regions of touch screen display 112; sensor state, including information obtained from the device's various sensors and input control devices 116; and location information concerning the device's location and/or attitude.

Operating system 126 (e.g., Darwin, RTXC, LINUX, UNIX, OS X, iOS, WINDOWS, or an embedded operating system such as VxWorks) includes various software components and/or drivers for controlling and managing general system tasks (e.g., memory management, storage device control, power management, etc.) and facilitates communication between various hardware and software components.

Communication module 128 facilitates communication with other devices over one or more external ports 124 and also includes various software components for handling data received by RF circuitry 108 and/or external port 124. External port 124 (e.g., Universal Serial Bus (USB), FIRE-WIRE, etc.) is adapted for coupling directly to other devices or indirectly over a network (e.g., the Internet, wireless LAN, etc.). In some embodiments, the external port is a multi-pin (e.g., 30-pin) connector that is the same as, or similar to and/or compatible with, the 30-pin connector used on iPod® (trademark of Apple Inc.) devices.

Contact/motion module 130 optionally detects contact with touch screen 112 (in conjunction with display controller 156) and other touch-sensitive devices (e.g., a touchpad or physical click wheel). Contact/motion module 130 includes various software components for performing various operations related to detection of contact, such as determining if contact has occurred (e.g., detecting a finger-down event), determining an intensity of the contact (e.g., the force or pressure of the contact or a substitute for the force or pressure of the contact), determining if there is movement of the contact and tracking the movement across the touch-sensitive surface (e.g., detecting one or more finger-dragging events), and determining if the contact has ceased (e.g., detecting a finger-up event or a break in contact). Contact/motion module 130 receives contact data from the touch-sensitive surface. Determining movement of the point of contact, which is represented by a series of contact data, optionally includes determining speed (magnitude), velocity (magnitude and direction), and/or an acceleration (a change in magnitude and/or direction) of the point of contact. These operations are, optionally, applied to single contacts (e.g., one finger contacts) or to multiple simultaneous contacts (e.g., "multitouch"/multiple finger contacts). In some embodiments, contact/motion module 130 and display controller 156 detect contact on a touchpad.

In some embodiments, contact/motion module 130 uses a set of one or more intensity thresholds to determine whether an operation has been performed by a user (e.g., to determine whether a user has "clicked" on an icon). In some embodiments, at least a subset of the intensity thresholds are determined in accordance with software parameters (e.g., the intensity thresholds are not determined by the activation thresholds of particular physical actuators and can be adjusted without changing the physical hardware of device 100). For example, a mouse "click" threshold of a trackpad or touch screen display can be set to any of a large range of predefined threshold values without changing the trackpad or touch screen display hardware. Additionally, in some implementations, a user of the device is provided with software settings for adjusting one or more of the set of intensity thresholds (e.g., by adjusting individual intensity thresholds and/or by adjusting a plurality of intensity thresholds at once with a system-level click "intensity" parameter).

Contact/motion module 130 optionally detects a gesture input by a user. Different gestures on the touch-sensitive surface have different contact patterns (e.g., different motions, timings, and/or intensities of detected contacts). Thus, a gesture is, optionally, detected by detecting a particular contact pattern. For example, detecting a finger tap gesture includes detecting a finger-down event followed by detecting a finger-up (liftoff) event at the same position (or substantially the same position) as the finger-down event (e.g., at the position of an icon). As another example, detecting a finger swipe gesture on the touch-sensitive surface includes detecting a finger-down event followed by detecting one or more finger-dragging events, and subsequently followed by detecting a finger-up (liftoff) event.

Graphics module 132 includes various known software components for rendering and displaying graphics on touch screen 112 or other display, including components for changing the visual impact (e.g., brightness, transparency, saturation, contrast, or other visual property) of graphics that are displayed. As used herein, the term "graphics" includes any object that can be displayed to a user, including, without limitation, text, web pages, icons (such as user-interface objects including soft keys), digital images, videos, animations, and the like.

In some embodiments, graphics module 132 stores data representing graphics to be used. Each graphic is, optionally, assigned a corresponding code. Graphics module 132 receives, from applications etc., one or more codes specifying graphics to be displayed along with, if necessary, coordinate data and other graphic property data, and then generates screen image data to output to display controller 156.

Haptic feedback module 133 includes various software components for generating instructions used by tactile output generator(s) 167 to produce tactile outputs at one or more locations on device 100 in response to user interactions with device 100.

Text input module 134, which is, optionally, a component of graphics module 132, provides soft keyboards for entering text in various applications (e.g., contacts 137, e-mail 140, IM 141, browser 147, and any other application that needs text input).

GPS module 135 determines the location of the device and provides this information for use in various applications (e.g., to telephone 138 for use in location-based dialing; to camera 143 as picture/video metadata; and to applications that provide location-based services such as weather widgets, local yellow page widgets, and map/navigation widgets).

Applications 136 optionally include the following modules (or sets of instructions), or a subset or superset thereof:
- Contacts module 137 (sometimes called an address book or contact list);
- Telephone module 138;
- Video conference module 139;
- E-mail client module 140;
- Instant messaging (IM) module 141;
- Workout support module 142;
- Camera module 143 for still and/or video images;
- Image management module 144;
- Video player module;
- Music player module;
- Browser module 147;
- Calendar module 148;
- Widget modules 149, which optionally include one or more of: weather widget 149-1, stocks widget 149-2, calculator widget 149-3, alarm clock widget 149-4, dictionary widget 149-5, and other widgets obtained by the user, as well as user-created widgets 149-6;
- Widget creator module 150 for making user-created widgets 149-6;
- Search module 151;
- Video and music player module 152, which merges video player module and music player module;
- Notes module 153;
- Map module 154; and/or
- Online video module 155.

Examples of other applications 136 that are, optionally, stored in memory 102 include other word processing applications, other image editing applications, drawing applications, presentation applications, JAVA-enabled applications, encryption, digital rights management, voice recognition, and voice replication.

In conjunction with touch screen 112, display controller 156, contact/motion module 130, graphics module 132, and text input module 134, contacts module 137 are, optionally, used to manage an address book or contact list (e.g., stored in application internal state 192 of contacts module 137 in memory 102 or memory 370), including: adding name(s) to the address book; deleting name(s) from the address book; associating telephone number(s), e-mail address(es), physical address(es) or other information with a name; associating an image with a name; categorizing and sorting names; providing telephone numbers or e-mail addresses to initiate and/or facilitate communications by telephone 138, video conference module 139, e-mail 140, or IM 141; and so forth.

In conjunction with RF circuitry 108, audio circuitry 110, speaker 111, microphone 113, touch screen 112, display controller 156, contact/motion module 130, graphics module 132, and text input module 134, telephone module 138 are optionally, used to enter a sequence of characters corresponding to a telephone number, access one or more telephone numbers in contacts module 137, modify a telephone number that has been entered, dial a respective telephone number, conduct a conversation, and disconnect or hang up when the conversation is completed. As noted above, the wireless communication optionally uses any of a plurality of communications standards, protocols, and technologies.

In conjunction with RF circuitry 108, audio circuitry 110, speaker 111, microphone 113, touch screen 112, display controller 156, optical sensor 164, optical sensor controller 158, contact/motion module 130, graphics module 132, text input module 134, contacts module 137, and telephone module 138, video conference module 139 includes executable instructions to initiate, conduct, and terminate a video conference between a user and one or more other participants in accordance with user instructions.

In conjunction with RF circuitry 108, touch screen 112, display controller 156, contact/motion module 130, graphics module 132, and text input module 134, e-mail client module 140 includes executable instructions to create, send, receive, and manage e-mail in response to user instructions. In conjunction with image management module 144, e-mail client module 140 makes it very easy to create and send e-mails with still or video images taken with camera module 143.

In conjunction with RF circuitry 108, touch screen 112, display controller 156, contact/motion module 130, graphics module 132, and text input module 134, the instant messaging module 141 includes executable instructions to enter a sequence of characters corresponding to an instant message, to modify previously entered characters, to transmit a respective instant message (for example, using a Short Message Service (SMS) or Multimedia Message Service (MMS) protocol for telephony-based instant messages or using XMPP, SIMPLE, or IMPS for Internet-based instant messages), to receive instant messages, and to view received instant messages. In some embodiments, transmitted and/or received instant messages optionally include graphics, photos, audio files, video files and/or other attachments as are supported in an MMS and/or an Enhanced Messaging Service (EMS). As used herein, "instant messaging" refers to both telephony-based messages (e.g., messages sent using SMS or MMS) and Internet-based messages (e.g., messages sent using XMPP, SIMPLE, or IMPS).

In conjunction with RF circuitry 108, touch screen 112, display controller 156, contact/motion module 130, graphics module 132, text input module 134, GPS module 135, map module 154, and music player module, workout support module 142 includes executable instructions to create workouts (e.g., with time, distance, and/or calorie burning goals); communicate with workout sensors (sports devices); receive workout sensor data; calibrate sensors used to monitor a workout; select and play music for a workout; and display, store, and transmit workout data.

In conjunction with touch screen 112, display controller 156, optical sensor(s) 164, optical sensor controller 158, contact/motion module 130, graphics module 132, and image management module 144, camera module 143 includes executable instructions to capture still images or video (including a video stream) and store them into memory 102, modify characteristics of a still image or video, or delete a still image or video from memory 102.

In conjunction with touch screen 112, display controller 156, contact/motion module 130, graphics module 132, text input module 134, and camera module 143, image management module 144 includes executable instructions to arrange, modify (e.g., edit), or otherwise manipulate, label, delete, present (e.g., in a digital slide show or album), and store still and/or video images.

In conjunction with RF circuitry 108, touch screen 112, display controller 156, contact/motion module 130, graphics module 132, and text input module 134, browser module 147 includes executable instructions to browse the Internet in accordance with user instructions, including searching, linking to, receiving, and displaying web pages or portions thereof, as well as attachments and other files linked to web pages.

In conjunction with RF circuitry 108, touch screen 112, display controller 156, contact/motion module 130, graphics module 132, text input module 134, e-mail client module 140, and browser module 147, calendar module 148 includes executable instructions to create, display, modify, and store calendars and data associated with calendars (e.g., calendar entries, to-do lists, etc.) in accordance with user instructions.

In conjunction with RF circuitry 108, touch screen 112, display controller 156, contact/motion module 130, graphics module 132, text input module 134, and browser module 147, widget modules 149 are mini-applications that are, optionally, downloaded and used by a user (e.g., weather widget 149-1, stocks widget 149-2, calculator widget 149-3, alarm clock widget 149-4, and dictionary widget 149-5) or created by the user (e.g., user-created widget 149-6). In some embodiments, a widget includes an HTML (Hypertext Markup Language) file, a CSS (Cascading Style Sheets) file, and a JavaScript file. In some embodiments, a widget includes an XML (Extensible Markup Language) file and a JavaScript file (e.g., Yahoo! Widgets).

In conjunction with RF circuitry 108, touch screen 112, display controller 156, contact/motion module 130, graphics module 132, text input module 134, and browser module 147, the widget creator module 150 are, optionally, used by a user to create widgets (e.g., turning a user-specified portion of a web page into a widget).

In conjunction with touch screen 112, display controller 156, contact/motion module 130, graphics module 132, and text input module 134, search module 151 includes executable instructions to search for text, music, sound, image, video, and/or other files in memory 102 that match one or more search criteria (e.g., one or more user-specified search terms) in accordance with user instructions.

In conjunction with touch screen 112, display controller 156, contact/motion module 130, graphics module 132, audio circuitry 110, speaker 111, RF circuitry 108, and browser module 147, video and music player module 152 includes executable instructions that allow the user to download and play back recorded music and other sound files stored in one or more file formats, such as MP3 or AAC files, and executable instructions to display, present, or otherwise play back videos (e.g., on touch screen 112 or on an external, connected display via external port 124). In some embodiments, device 100 optionally includes the functionality of an MP3 player, such as an iPod (trademark of Apple Inc.).

In conjunction with touch screen 112, display controller 156, contact/motion module 130, graphics module 132, and text input module 134, notes module 153 includes executable instructions to create and manage notes, to-do lists, and the like in accordance with user instructions.

In conjunction with RF circuitry 108, touch screen 112, display controller 156, contact/motion module 130, graphics module 132, text input module 134, GPS module 135, and browser module 147, map module 154 are, optionally, used to receive, display, modify, and store maps and data associated with maps (e.g., driving directions, data on stores and other points of interest at or near a particular location, and other location-based data) in accordance with user instructions.

In conjunction with touch screen 112, display controller 156, contact/motion module 130, graphics module 132, audio circuitry 110, speaker 111, RF circuitry 108, text input module 134, e-mail client module 140, and browser module 147, online video module 155 includes instructions that allow the user to access, browse, receive (e.g., by streaming and/or download), play back (e.g., on the touch screen or on an external, connected display via external port 124), send an e-mail with a link to a particular online video, and otherwise manage online videos in one or more file formats, such as H.264. In some embodiments, instant messaging module 141, rather than e-mail client module 140, is used to send a link to a particular online video. Additional description of the online video application can be found in U.S. Provisional Patent Application No. 60/936,562, "Portable Multifunction Device, Method, and Graphical User Interface for Playing Online Videos," filed Jun. 20, 2007, and U.S. patent application Ser. No. 11/968,067, "Portable Multifunction Device, Method, and Graphical User Interface for Playing Online Videos," filed Dec. 31, 2007, the contents of which are hereby incorporated by reference in their entirety.

Each of the above-identified modules and applications corresponds to a set of executable instructions for performing one or more functions described above and the methods described in this application (e.g., the computer-implemented methods and other information processing methods described herein). These modules (e.g., sets of instructions) need not be implemented as separate software programs, procedures, or modules, and thus various subsets of these modules are, optionally, combined or otherwise rearranged in various embodiments. For example, video player module is, optionally, combined with music player module into a single module (e.g., video and music player module 152, FIG. 1A). In some embodiments, memory 102 optionally stores a subset of the modules and data structures identified above. Furthermore, memory 102 optionally stores additional modules and data structures not described above.

In some embodiments, device 100 is a device where operation of a predefined set of functions on the device is performed exclusively through a touch screen and/or a touchpad. By using a touch screen and/or a touchpad as the primary input control device for operation of device 100, the number of physical input control devices (such as push buttons, dials, and the like) on device 100 is, optionally, reduced.

The predefined set of functions that are performed exclusively through a touch screen and/or a touchpad optionally include navigation between user interfaces. In some embodiments, the touchpad, when touched by the user, navigates device 100 to a main, home, or root menu from any user interface that is displayed on device 100. In such embodiments, a "menu button" is implemented using a touchpad. In some other embodiments, the menu button is a physical push button or other physical input control device instead of a touchpad.

Figure 1B:
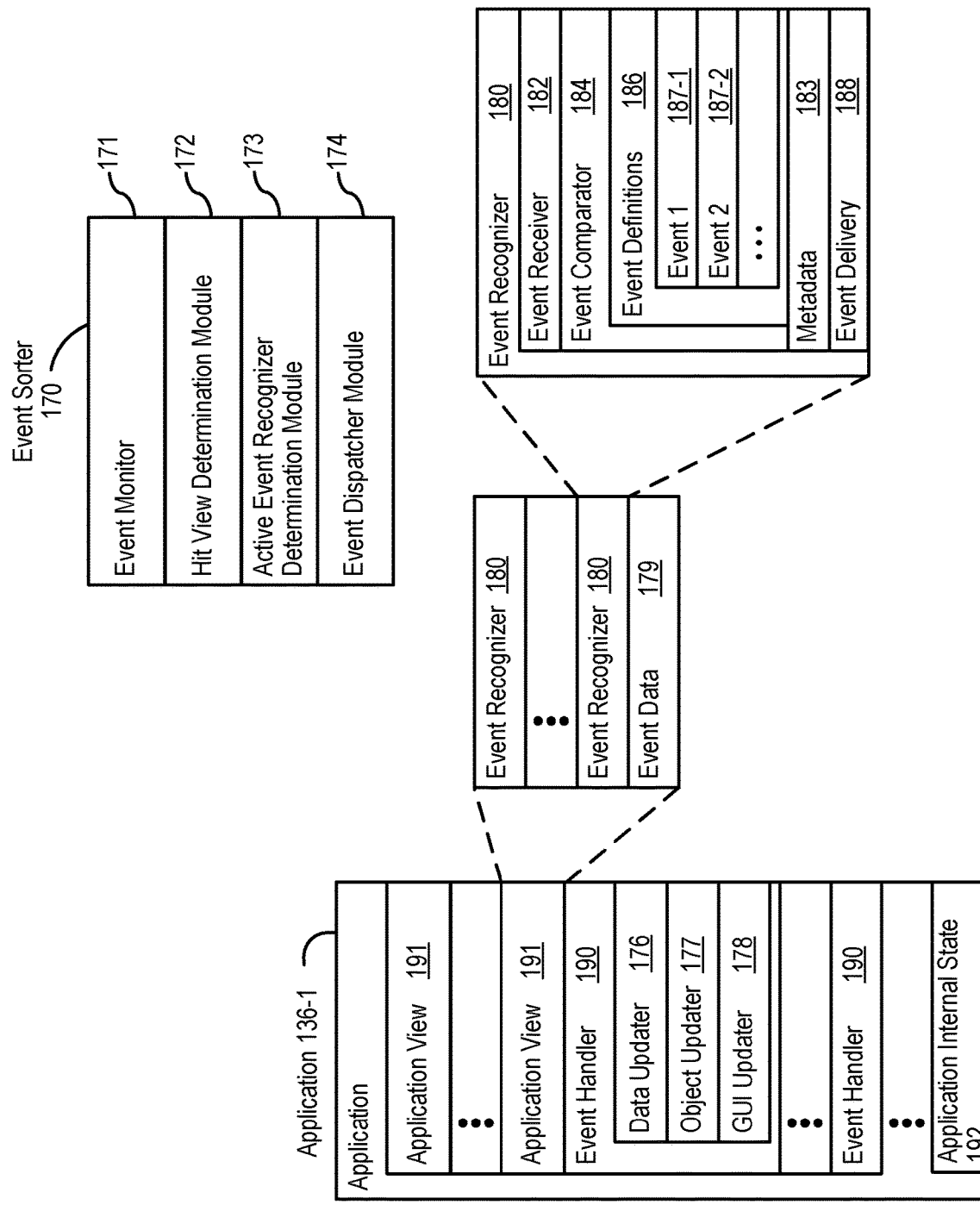
FIG. 1B is a block diagram illustrating exemplary components for event handling in accordance with some embodiments.

FIG. 1B is a block diagram illustrating exemplary components for event handling in accordance with some embodiments. In some embodiments, memory 102 (FIG. 1A) or 370 (FIG. 3) includes event sorter 170 (e.g., in operating system 126) and a respective application 136-1 (e.g., any of the aforementioned applications 137-151, 155, 380-390).

Event sorter 170 receives event information and determines the application 136-1 and application view 191 of application 136-1 to which to deliver the event information. Event sorter 170 includes event monitor 171 and event dispatcher module 174. In some embodiments, application 136-1 includes application internal state 192, which indicates the current application view(s) displayed on touch-sensitive display 112 when the application is active or executing. In some embodiments, device/global internal state 157 is used by event sorter 170 to determine which application(s) is (are) currently active, and application internal state 192 is used by event sorter 170 to determine application views 191 to which to deliver event information.

In some embodiments, application internal state 192 includes additional information, such as one or more of:

resume information to be used when application 136-1 resumes execution, user interface state information that indicates information being displayed or that is ready for display by application 136-1, a state queue for enabling the user to go back to a prior state or view of application 136-1, and a redo/undo queue of previous actions taken by the user.

Event monitor 171 receives event information from peripherals interface 118. Event information includes information about a sub-event (e.g., a user touch on touch-sensitive display 112, as part of a multi-touch gesture). Peripherals interface 118 transmits information it receives from I/O subsystem 106 or a sensor, such as proximity sensor 166, accelerometer(s) 168, and/or microphone 113 (through audio circuitry 110). Information that peripherals interface 118 receives from I/O subsystem 106 includes information from touch-sensitive display 112 or a touch-sensitive surface.

In some embodiments, event monitor 171 sends requests to the peripherals interface 118 at predetermined intervals. In response, peripherals interface 118 transmits event information. In other embodiments, peripherals interface 118 transmits event information only when there is a significant event (e.g., receiving an input above a predetermined noise threshold and/or for more than a predetermined duration).

In some embodiments, event sorter 170 also includes a hit view determination module 172 and/or an active event recognizer determination module 173.

Hit view determination module 172 provides software procedures for determining where a sub-event has taken place within one or more views when touch-sensitive display 112 displays more than one view. Views are made up of controls and other elements that a user can see on the display.

Another aspect of the user interface associated with an application is a set of views, sometimes herein called application views or user interface windows, in which information is displayed and touch-based gestures occur. The application views (of a respective application) in which a touch is detected optionally correspond to programmatic levels within a programmatic or view hierarchy of the application. For example, the lowest level view in which a touch is detected is, optionally, called the hit view, and the set of events that are recognized as proper inputs are, optionally, determined based, at least in part, on the hit view of the initial touch that begins a touch-based gesture.

Hit view determination module 172 receives information related to sub-events of a touch-based gesture. When an application has multiple views organized in a hierarchy, hit view determination module 172 identifies a hit view as the lowest view in the hierarchy which should handle the sub-event. In most circumstances, the hit view is the lowest level view in which an initiating sub-event occurs (e.g., the first sub-event in the sequence of sub-events that form an event or potential event). Once the hit view is identified by the hit view determination module 172, the hit view typically receives all sub-events related to the same touch or input source for which it was identified as the hit view.

Active event recognizer determination module 173 determines which view or views within a view hierarchy should receive a particular sequence of sub-events. In some embodiments, active event recognizer determination module 173 determines that only the hit view should receive a particular sequence of sub-events. In other embodiments, active event recognizer determination module 173 determines that all views that include the physical location of a sub-event are actively involved views, and therefore determines that all actively involved views should receive a particular sequence of sub-events. In other embodiments, even if touch sub-events were entirely confined to the area associated with one particular view, views higher in the hierarchy would still remain as actively involved views.

Event dispatcher module 174 dispatches the event information to an event recognizer (e.g., event recognizer 180). In embodiments including active event recognizer determination module 173, event dispatcher module 174 delivers the event information to an event recognizer determined by active event recognizer determination module 173. In some embodiments, event dispatcher module 174 stores in an event queue the event information, which is retrieved by a respective event receiver 182.

In some embodiments, operating system 126 includes event sorter 170. Alternatively, application 136-1 includes event sorter 170. In yet other embodiments, event sorter 170 is a stand-alone module, or a part of another module stored in memory 102, such as contact/motion module 130.

In some embodiments, application 136-1 includes a plurality of event handlers 190 and one or more application views 191, each of which includes instructions for handling touch events that occur within a respective view of the application's user interface. Each application view 191 of the application 136-1 includes one or more event recognizers 180. Typically, a respective application view 191 includes a plurality of event recognizers 180. In other embodiments, one or more of event recognizers 180 are part of a separate module, such as a user interface kit or a higher level object from which application 136-1 inherits methods and other properties. In some embodiments, a respective event handler 190 includes one or more of: data updater 176, object updater 177, GUI updater 178, and/or event data 179 received from event sorter 170. Event handler 190 optionally utilizes or calls data updater 176, object updater 177, or GUI updater 178 to update the application internal state 192. Alternatively, one or more of the application views 191 include one or more respective event handlers 190. Also, in some embodiments, one or more of data updater 176, object updater 177, and GUI updater 178 are included in a respective application view 191.

A respective event recognizer 180 receives event information (e.g., event data 179) from event sorter 170 and identifies an event from the event information. Event recognizer 180 includes event receiver 182 and event comparator 184. In some embodiments, event recognizer 180 also includes at least a subset of: metadata 183, and event delivery instructions 188 (which optionally include sub-event delivery instructions).

Event receiver 182 receives event information from event sorter 170. The event information includes information about a sub-event, for example, a touch or a touch movement. Depending on the sub-event, the event information also includes additional information, such as location of the sub-event. When the sub-event concerns motion of a touch, the event information optionally also includes speed and direction of the sub-event. In some embodiments, events include rotation of the device from one orientation to another (e.g., from a portrait orientation to a landscape orientation, or vice versa), and the event information includes corresponding information about the current orientation (also called device attitude) of the device.

Event comparator 184 compares the event information to predefined event or sub-event definitions and, based on the comparison, determines an event or sub-event, or determines or updates the state of an event or sub-event. In some embodiments, event comparator 184 includes event definitions 186. Event definitions 186 contain definitions of events (e.g., predefined sequences of sub-events), for example, event 1 (187-1), event 2 (187-2), and others. In some embodiments, sub-events in an event (187) include, for example, touch begin, touch end, touch movement, touch cancellation, and multiple touching. In one example, the definition for event 1 (187-1) is a double tap on a displayed object. The double tap, for example, comprises a first touch (touch begin) on the displayed object for a predetermined phase, a first liftoff (touch end) for a predetermined phase, a second touch (touch begin) on the displayed object for a predetermined phase, and a second liftoff (touch end) for a predetermined phase. In another example, the definition for event 2 (187-2) is a dragging on a displayed object. The dragging, for example, comprises a touch (or contact) on the displayed object for a predetermined phase, a movement of the touch across touch-sensitive display 112, and liftoff of the touch (touch end). In some embodiments, the event also includes information for one or more associated event handlers 190.

In some embodiments, event definition 187 includes a definition of an event for a respective user-interface object. In some embodiments, event comparator 184 performs a hit test to determine which user-interface object is associated with a sub-event. For example, in an application view in which three user-interface objects are displayed on touch-sensitive display 112, when a touch is detected on touch-sensitive display 112, event comparator 184 performs a hit test to determine which of the three user-interface objects is associated with the touch (sub-event). If each displayed object is associated with a respective event handler 190, the event comparator uses the result of the hit test to determine which event handler 190 should be activated. For example, event comparator 184 selects an event handler associated with the sub-event and the object triggering the hit test.

In some embodiments, the definition for a respective event (187) also includes delayed actions that delay delivery of the event information until after it has been determined whether the sequence of sub-events does or does not correspond to the event recognizer's event type.

When a respective event recognizer 180 determines that the series of sub-events do not match any of the events in event definitions 186, the respective event recognizer 180 enters an event impossible, event failed, or event ended state, after which it disregards subsequent sub-events of the touch-based gesture. In this situation, other event recognizers, if any, that remain active for the hit view continue to track and process sub-events of an ongoing touch-based gesture.

In some embodiments, a respective event recognizer 180 includes metadata 183 with configurable properties, flags, and/or lists that indicate how the event delivery system should perform sub-event delivery to actively involved event recognizers. In some embodiments, metadata 183 includes configurable properties, flags, and/or lists that indicate how event recognizers interact, or are enabled to interact, with one another. In some embodiments, metadata 183 includes configurable properties, flags, and/or lists that indicate whether sub-events are delivered to varying levels in the view or programmatic hierarchy.

In some embodiments, a respective event recognizer 180 activates event handler 190 associated with an event when one or more particular sub-events of an event are recognized. In some embodiments, a respective event recognizer 180 delivers event information associated with the event to event handler 190. Activating an event handler 190 is distinct from sending (and deferred sending) sub-events to a respective hit view. In some embodiments, event recognizer 180 throws a flag associated with the recognized event, and event handler 190 associated with the flag catches the flag and performs a predefined process.

In some embodiments, event delivery instructions 188 include sub-event delivery instructions that deliver event information about a sub-event without activating an event handler. Instead, the sub-event delivery instructions deliver event information to event handlers associated with the series of sub-events or to actively involved views. Event handlers associated with the series of sub-events or with actively involved views receive the event information and perform a predetermined process.

In some embodiments, data updater 176 creates and updates data used in application 136-1. For example, data updater 176 updates the telephone number used in contacts module 137, or stores a video file used in video player module. In some embodiments, object updater 177 creates and updates objects used in application 136-1. For example, object updater 177 creates a new user-interface object or updates the position of a user-interface object. GUI updater 178 updates the GUI. For example, GUI updater 178 prepares display information and sends it to graphics module 132 for display on a touch-sensitive display.

In some embodiments, event handler(s) 190 includes or has access to data updater 176, object updater 177, and GUI updater 178. In some embodiments, data updater 176, object updater 177, and GUI updater 178 are included in a single module of a respective application 136-1 or application view 191. In other embodiments, they are included in two or more software modules.

It shall be understood that the foregoing discussion regarding event handling of user touches on touch-sensitive displays also applies to other forms of user inputs to operate multifunction devices 100 with input devices, not all of which are initiated on touch screens. For example, mouse movement and mouse button presses, optionally coordinated with single or multiple keyboard presses or holds; contact movements such as taps, drags, scrolls, etc. on touchpads; pen stylus inputs; movement of the device; oral instructions; detected eye movements; biometric inputs; and/or any combination thereof are optionally utilized as inputs corresponding to sub-events which define an event to be recognized.

Figure 2:
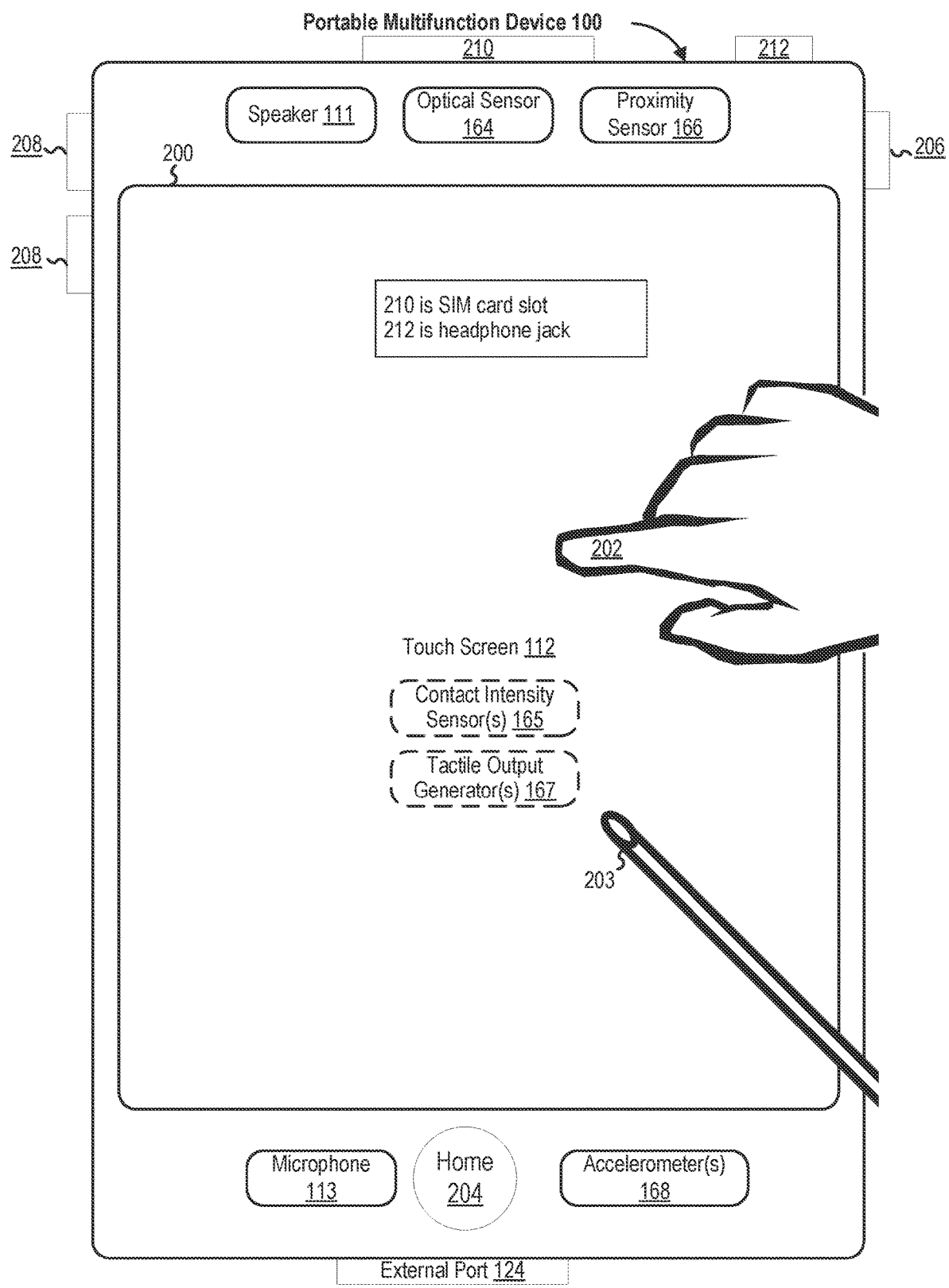
FIG. 2 illustrates a portable multifunction device having a touch screen in accordance with some embodiments.

FIG. 2 illustrates a portable multifunction device 100 having a touch screen 112 in accordance with some embodiments. The touch screen optionally displays one or more graphics within user interface (UI) 200. In this embodiment, as well as others described below, a user is enabled to select one or more of the graphics by making a gesture on the graphics, for example, with one or more fingers 202 (not drawn to scale in the figure) or one or more styluses 203 (not drawn to scale in the figure). In some embodiments, selection of one or more graphics occurs when the user breaks contact with the one or more graphics. In some embodiments, the gesture optionally includes one or more taps, one or more swipes (from left to right, right to left, upward and/or downward), and/or a rolling of a finger (from right to left, left to right, upward and/or downward) that has made contact with device 100. In some implementations or circumstances, inadvertent contact with a graphic does not select the graphic. For example, a swipe gesture that sweeps over an application icon optionally does not select the corresponding application when the gesture corresponding to selection is a tap.

Device 100 optionally also include one or more physical buttons, such as "home" or menu button 204. As described previously, menu button 204 is, optionally, used to navigate to any application 136 in a set of applications that are, optionally, executed on device 100. Alternatively, in some embodiments, the menu button is implemented as a soft key in a GUI displayed on touch screen 112.

In some embodiments, device 100 includes touch screen 112, menu button 204, push button 206 for powering the device on/off and locking the device, volume adjustment button(s) 208, subscriber identity module (SIM) card slot 210, headset jack 212, and docking/charging external port 124. Push button 206 is, optionally, used to turn the power on/off on the device by depressing the button and holding the button in the depressed state for a predefined time interval; to lock the device by depressing the button and releasing the button before the predefined time interval has elapsed; and/or to unlock the device or initiate an unlock process. In an alternative embodiment, device 100 also accepts verbal input for activation or deactivation of some functions through microphone 113. Device 100 also, optionally, includes one or more contact intensity sensors 165 for detecting intensity of contacts on touch screen 112 and/or one or more tactile output generators 167 for generating tactile outputs for a user of device 100.

FIG. 3 is a block diagram of an exemplary multifunction device with a display and a touch-sensitive surface in accordance with some embodiments. Device 300 need not be portable. In some embodiments, device 300 is a laptop computer, a desktop computer, a tablet computer, a multimedia player device, a navigation device, an educational device (such as a child's learning toy), a gaming system, or a control device (e.g., a home or industrial controller). Device 300 typically includes one or more processing units (CPUs) 310, one or more network or other communications interfaces 360, memory 370, and one or more communication buses 320 for interconnecting these components. Communication buses 320 optionally include circuitry (sometimes called a chipset) that interconnects and controls communications between system components. Device 300 includes input/output (I/O) interface 330 comprising display 340, which is typically a touch screen display. I/O interface 330 also optionally includes a keyboard and/or mouse (or other pointing device) 350 and touchpad 355, tactile output generator 357 for generating tactile outputs on device 300 (e.g., similar to tactile output generator(s) 167 described above with reference to FIG. 1A), sensors 359 (e.g., optical, acceleration, proximity, touch-sensitive, and/or contact intensity sensors similar to contact intensity sensor(s) 165 described above with reference to FIG. 1A). Memory 370 includes high-speed random access memory, such as DRAM, SRAM, DDR RAM, or other random access solid state memory devices; and optionally includes non-volatile memory, such as one or more magnetic disk storage devices, optical disk storage devices, flash memory devices, or other non-volatile solid state storage devices. Memory 370 optionally includes one or more storage devices remotely located from CPU(s) 310. In some embodiments, memory 370 stores programs, modules, and data structures analogous to the programs, modules, and data structures stored in memory 102 of portable multifunction device 100 (FIG. 1A), or a subset thereof. Furthermore, memory 370 optionally stores additional programs, modules, and data structures not present in memory 102 of portable multifunction device 100. For example, memory 370 of device 300 optionally stores drawing module 380, presentation module 382, word processing module 384, website creation module 386, disk authoring module 388, and/or spreadsheet module 390, while memory 102 of portable multifunction device 100 (FIG. 1A) optionally does not store these modules.

Each of the above-identified elements in FIG. 3 is, optionally, stored in one or more of the previously mentioned memory devices. Each of the above-identified modules corresponds to a set of instructions for performing a function described above. The above-identified modules or programs (e.g., sets of instructions) need not be implemented as separate software programs, procedures, or modules, and thus various subsets of these modules are, optionally, combined or otherwise rearranged in various embodiments. In some embodiments, memory 370 optionally stores a subset of the modules and data structures identified above. Furthermore, memory 370 optionally stores additional modules and data structures not described above.

Attention is now directed towards embodiments of user interfaces that are, optionally, implemented on, for example, portable multifunction device 100.

Figure 4A:
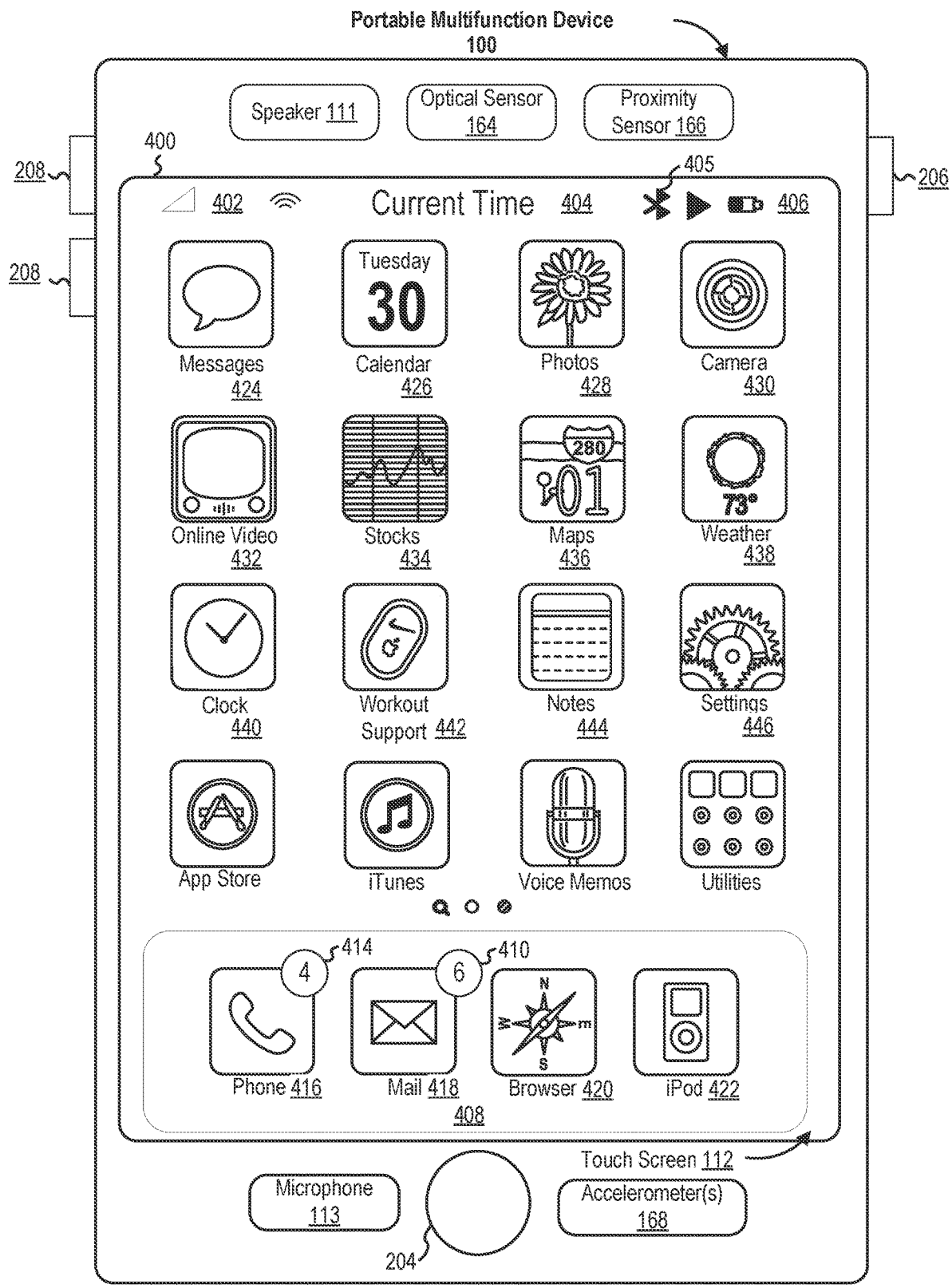
FIG. 4A illustrates an exemplary user interface for a menu of applications on a portable multifunction device in accordance with some embodiments.

FIG. 4A illustrates an exemplary user interface for a menu of applications on portable multifunction device 100 in accordance with some embodiments. Similar user interfaces are, optionally, implemented on device 300. In some embodiments, user interface 400 includes the following elements, or a subset or superset thereof:

Signal strength indicator(s) 402 for wireless communication(s), such as cellular and Wi-Fi signals;
Time 404;
Bluetooth indicator 405;
Battery status indicator 406;
Tray 408 with icons for frequently used applications, such as:
  Icon 416 for telephone module 138, labeled "Phone," which optionally includes an indicator 414 of the number of missed calls or voicemail messages;
  Icon 418 for e-mail client module 140, labeled "Mail," which optionally includes an indicator 410 of the number of unread e-mails;
  Icon 420 for browser module 147, labeled "Browser;" and
  Icon 422 for video and music player module 152, also referred to as iPod (trademark of Apple Inc.) module 152, labeled "iPod;" and
Icons for other applications, such as:
  Icon 424 for IM module 141, labeled "Messages;"
  Icon 426 for calendar module 148, labeled "Calendar;"
  Icon 428 for image management module 144, labeled "Photos;"
  Icon 430 for camera module 143, labeled "Camera;"
  Icon 432 for online video module 155, labeled "Online Video;"
  Icon 434 for stocks widget 149-2, labeled "Stocks;"
  Icon 436 for map module 154, labeled "Maps;"
  Icon 438 for weather widget 149-1, labeled "Weather;"
  Icon 440 for alarm clock widget 149-4, labeled "Clock;"
  Icon 442 for workout support module 142, labeled "Workout Support;"
  Icon 444 for notes module 153, labeled "Notes;" and
  Icon 446 for a settings application or module, labeled "Settings," which provides access to settings for device 100 and its various applications 136.

It should be noted that the icon labels illustrated in FIG. 4A are merely exemplary. For example, icon 422 for video and music player module 152 is labeled "Music" or "Music Player." Other labels are, optionally, used for various application icons. In some embodiments, a label for a respective application icon includes a name of an application corresponding to the respective application icon. In some embodiments, a label for a particular application icon is distinct from a name of an application corresponding to the particular application icon.

Figure 4B:
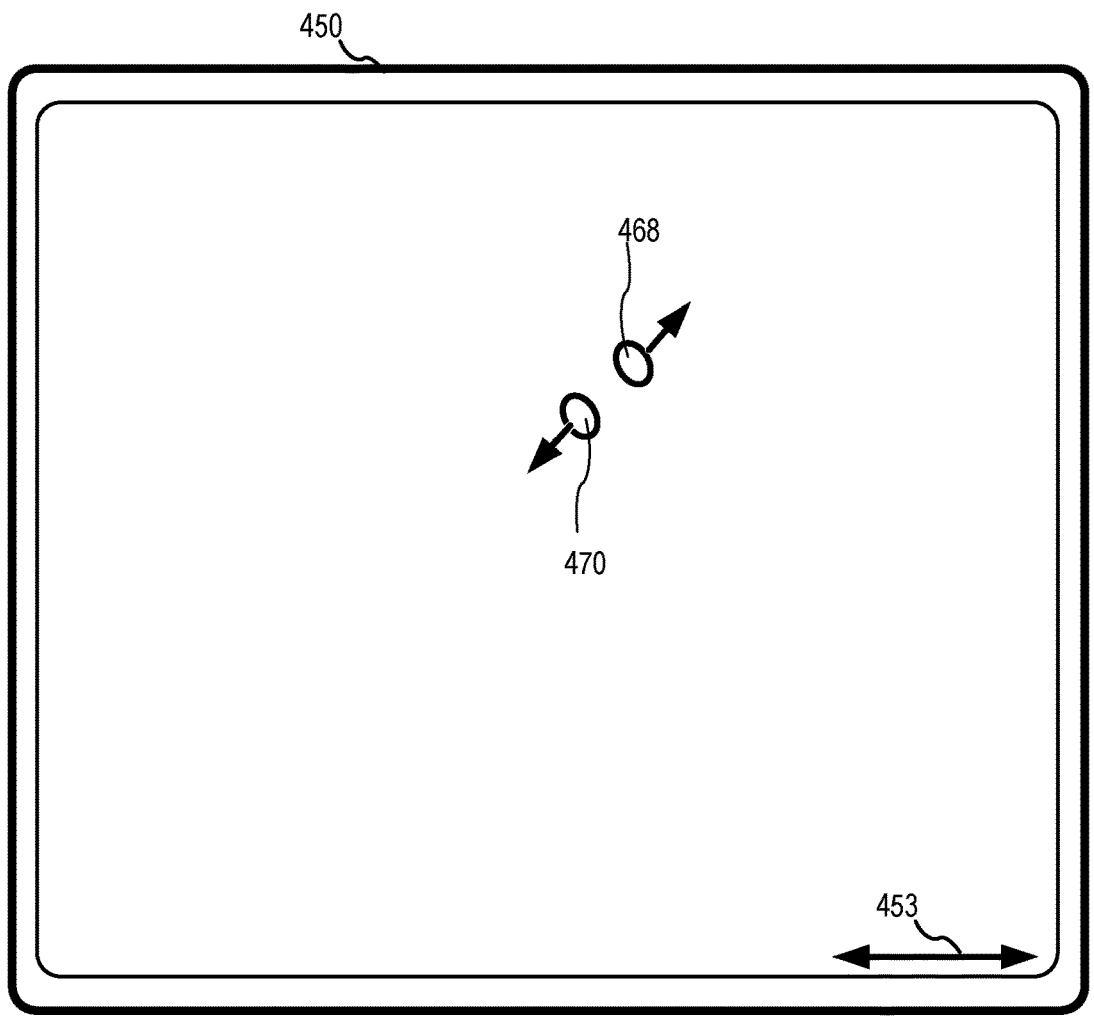
FIG. 4B illustrates an exemplary user interface for a multifunction device with a touch-sensitive surface that is separate from the display in accordance with some embodiments.
Figure 4B:
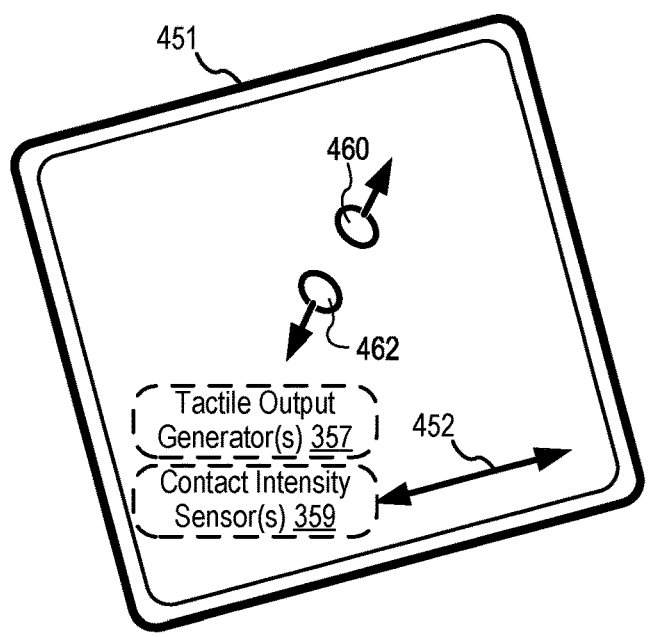

FIG. 4B illustrates an exemplary user interface on a device (e.g., device 300, FIG. 3) with a touch-sensitive surface 451 (e.g., a tablet or touchpad 355, FIG. 3) that is separate from the display 450 (e.g., touch screen display 112). Device 300 also, optionally, includes one or more contact intensity sensors (e.g., one or more of sensors 359) for detecting intensity of contacts on touch-sensitive surface 451 and/or one or more tactile output generators 357 for generating tactile outputs for a user of device 300.

Although some of the examples that follow will be given with reference to inputs on touch screen display 112 (where the touch-sensitive surface and the display are combined), in some embodiments, the device detects inputs on a touch-sensitive surface that is separate from the display, as shown in FIG. 4B. In some embodiments, the touch-sensitive surface (e.g., 451 in FIG. 4B) has a primary axis (e.g., 452 in FIG. 4B) that corresponds to a primary axis (e.g., 453 in FIG. 4B) on the display (e.g., 450). In accordance with these embodiments, the device detects contacts (e.g., 460 and 462 in FIG. 4B) with the touch-sensitive surface 451 at locations that correspond to respective locations on the display (e.g., in FIG. 4B, 460 corresponds to 468 and 462 corresponds to 470). In this way, user inputs (e.g., contacts 460 and 462, and movements thereof) detected by the device on the touch-sensitive surface (e.g., 451 in FIG. 4B) are used by the device to manipulate the user interface on the display (e.g., 450 in FIG. 4B) of the multifunction device when the touch-sensitive surface is separate from the display. It should be understood that similar methods are, optionally, used for other user interfaces described herein.

Additionally, while the following examples are given primarily with reference to finger inputs (e.g., finger contacts, finger tap gestures, finger swipe gestures), it should be understood that, in some embodiments, one or more of the finger inputs are replaced with input from another input device (e.g., a mouse-based input or stylus input). For example, a swipe gesture is, optionally, replaced with a mouse click (e.g., instead of a contact) followed by movement of the cursor along the path of the swipe (e.g., instead of movement of the contact). As another example, a tap gesture is, optionally, replaced with a mouse click while the cursor is located over the location of the tap gesture (e.g., instead of detection of the contact followed by ceasing to detect the contact). Similarly, when multiple user inputs are simultaneously detected, it should be understood that multiple computer mice are, optionally, used simultaneously, or a mouse and finger contacts are, optionally, used simultaneously.

Figure 5A:
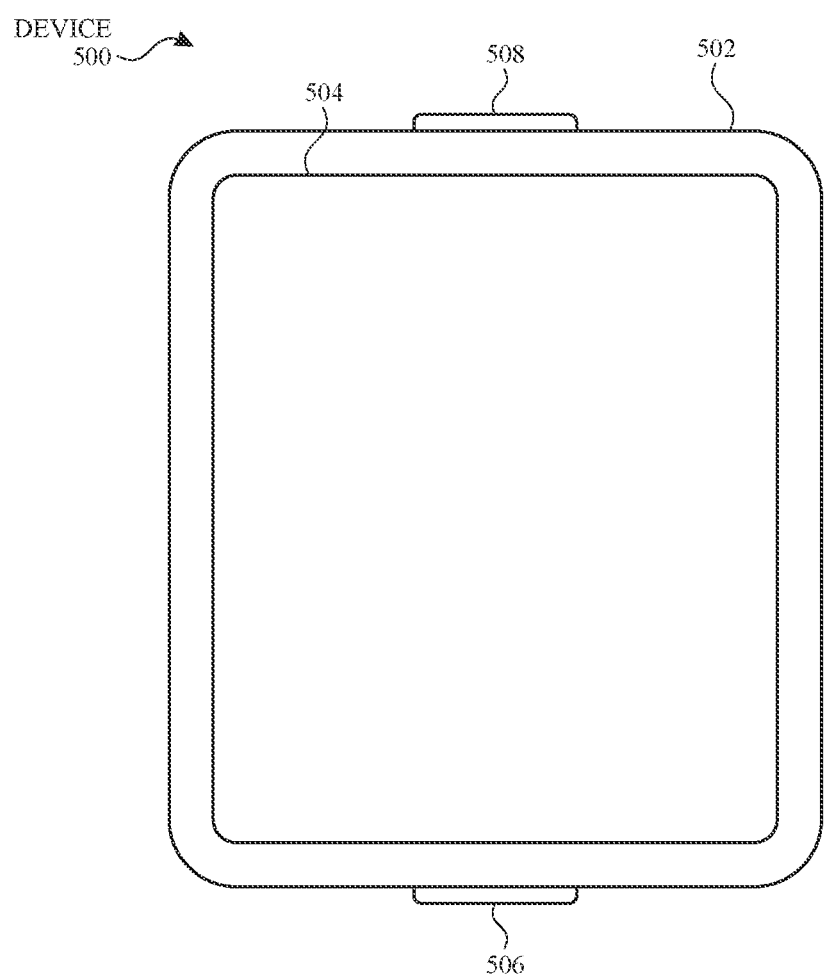
FIG. 5A illustrates a personal electronic device in accordance with some embodiments.

FIG. 5A illustrates exemplary personal electronic device 500. Device 500 includes body 502. In some embodiments, device 500 can include some or all of the features described with respect to devices 100 and 300 (e.g., FIGS. 1A-4B). In some embodiments, device 500 has touch-sensitive display screen 504, hereafter touch screen 504. Alternatively, or in addition to touch screen 504, device 500 has a display and a touch-sensitive surface. As with devices 100 and 300, in some embodiments, touch screen 504 (or the touch-sensitive surface) optionally includes one or more intensity sensors for detecting intensity of contacts (e.g., touches) being applied. The one or more intensity sensors of touch screen 504 (or the touch-sensitive surface) can provide output data that represents the intensity of touches. The user interface of device 500 can respond to touches based on their intensity, meaning that touches of different intensities can invoke different user interface operations on device 500.

Exemplary techniques for detecting and processing touch intensity are found, for example, in related applications: International Patent Application Serial No. PCT/US2013/040061, titled "Device, Method, and Graphical User Interface for Displaying User Interface Objects Corresponding to an Application," filed May 8, 2013, published as WIPO Publication No. WO/2013/169849, and International Patent Application Serial No. PCT/US2013/069483, titled "Device, Method, and Graphical User Interface for Transitioning Between Touch Input to Display Output Relationships," filed Nov. 11, 2013, published as WIPO Publication No. WO/2014/105276, each of which is hereby incorporated by reference in their entirety.

In some embodiments, device 500 has one or more input mechanisms 506 and 508. Input mechanisms 506 and 508, if included, can be physical. Examples of physical input mechanisms include push buttons and rotatable mechanisms. In some embodiments, device 500 has one or more attachment mechanisms. Such attachment mechanisms, if included, can permit attachment of device 500 with, for example, hats, eyewear, earrings, necklaces, shirts, jackets, bracelets, watch straps, chains, trousers, belts, shoes, purses, backpacks, and so forth. These attachment mechanisms permit device 500 to be worn by a user.

Figure 5B:
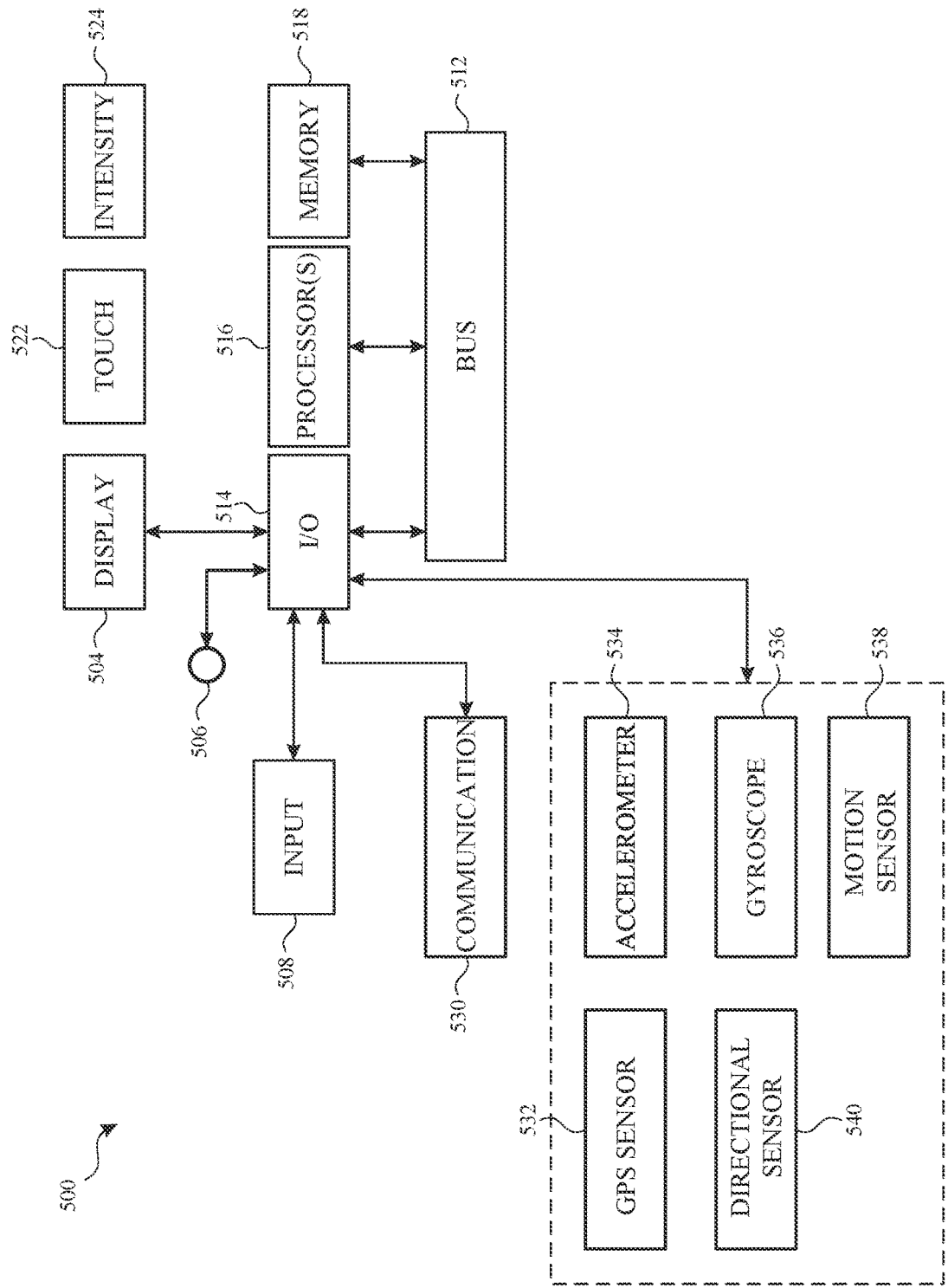
FIG. 5B is a block diagram illustrating a personal electronic device in accordance with some embodiments.

FIG. 5B depicts exemplary personal electronic device 500. In some embodiments, device 500 can include some or all of the components described with respect to FIGS. 1A, 1B, and 3. Device 500 has bus 512 that operatively couples I/O section 514 with one or more computer processors 516 and memory 518. I/O section 514 can be connected to display 504, which can have touch-sensitive component 522 and, optionally, intensity sensor 524 (e.g., contact intensity sensor). In addition, I/O section 514 can be connected with communication unit 530 for receiving application and operating system data, using Wi-Fi, Bluetooth, near field communication (NFC), cellular, and/or other wireless communication techniques. Device 500 can include input mechanisms 506 and/or 508. Input mechanism 506 is, optionally, a rotatable input device or a depressible and rotatable input device, for example. Input mechanism 508 is, optionally, a button, in some examples.

Input mechanism 508 is, optionally, a microphone, in some examples. Personal electronic device 500 optionally includes various sensors, such as GPS sensor 532, accelerometer 534, directional sensor 540 (e.g., compass), gyroscope 536, motion sensor 538, and/or a combination thereof, all of which can be operatively connected to I/O section 514.

Memory 518 of personal electronic device 500 can include one or more non-transitory computer-readable storage mediums, for storing computer-executable instructions, which, when executed by one or more computer processors 516, for example, can cause the computer processors to perform the techniques described below, including processes 1200-1400 (FIGS. 12-14). A computer-readable storage medium can be any medium that can tangibly contain or store computer-executable instructions for use by or in connection with the instruction execution system, apparatus, or device. In some examples, the storage medium is a transitory computer-readable storage medium. In some examples, the storage medium is a non-transitory computer-readable storage medium. The non-transitory computer-readable storage medium can include, but is not limited to, magnetic, optical, and/or semiconductor storages. Examples of such storage include magnetic disks, optical discs based on CD, DVD, or Blu-ray technologies, as well as persistent solid-state memory such as flash, solid-state drives, and the like. Personal electronic device 500 is not limited to the components and configuration of FIG. 5B, but can include other or additional components in multiple configurations.

As used here, the term "affordance" refers to a user-interactive graphical user interface object that is, optionally, displayed on the display screen of devices 100, 300, and/or 500 (FIGS. 1A, 3, and 5A-5B). For example, an image (e.g., icon), a button, and text (e.g., hyperlink) each optionally constitute an affordance.

As used herein, the term "focus selector" refers to an input element that indicates a current part of a user interface with which a user is interacting. In some implementations that include a cursor or other location marker, the cursor acts as a "focus selector" so that when an input (e.g., a press input) is detected on a touch-sensitive surface (e.g., touchpad 355 in FIG. 3 or touch-sensitive surface 451 in FIG. 4B) while the cursor is over a particular user interface element (e.g., a button, window, slider, or other user interface element), the particular user interface element is adjusted in accordance with the detected input. In some implementations that include a touch screen display (e.g., touch-sensitive display system 112 in FIG. 1A or touch screen 112 in FIG. 4A) that enables direct interaction with user interface elements on the touch screen display, a detected contact on the touch screen acts as a "focus selector" so that when an input (e.g., a press input by the contact) is detected on the touch screen display at a location of a particular user interface element (e.g., a button, window, slider, or other user interface element), the particular user interface element is adjusted in accordance with the detected input. In some implementations, focus is moved from one region of a user interface to another region of the user interface without corresponding movement of a cursor or movement of a contact on a touch screen display (e.g., by using a tab key or arrow keys to move focus from one button to another button); in these implementations, the focus selector moves in accordance with movement of focus between different regions of the user interface. Without regard to the specific form taken by the focus selector, the focus selector is generally the user interface element (or contact on a touch screen display) that is controlled by the user so as to communicate the user's intended interaction with the user interface (e.g., by indicating, to the device, the element of the user interface with which the user is intending to interact). For example, the location of a focus selector (e.g., a cursor, a contact, or a selection box) over a respective button while a press input is detected on the touch-sensitive surface (e.g., a touchpad or touch screen) will indicate that the user is intending to activate the respective button (as opposed to other user interface elements shown on a display of the device).

As used in the specification and claims, the term "characteristic intensity" of a contact refers to a characteristic of the contact based on one or more intensities of the contact. In some embodiments, the characteristic intensity is based on multiple intensity samples. The characteristic intensity is, optionally, based on a predefined number of intensity samples, or a set of intensity samples collected during a predetermined time period (e.g., 0.05, 0.1, 0.2, 0.5, 1, 2, 5, 10 seconds) relative to a predefined event (e.g., after detecting the contact, prior to detecting liftoff of the contact, before or after detecting a start of movement of the contact, prior to detecting an end of the contact, before or after detecting an increase in intensity of the contact, and/or before or after detecting a decrease in intensity of the contact). A characteristic intensity of a contact is, optionally, based on one or more of: a maximum value of the intensities of the contact, a mean value of the intensities of the contact, an average value of the intensities of the contact, a top 10 percentile value of the intensities of the contact, a value at the half maximum of the intensities of the contact, a value at the 90 percent maximum of the intensities of the contact, or the like. In some embodiments, the duration of the contact is used in determining the characteristic intensity (e.g., when the characteristic intensity is an average of the intensity of the contact over time). In some embodiments, the characteristic intensity is compared to a set of one or more intensity thresholds to determine whether an operation has been performed by a user. For example, the set of one or more intensity thresholds optionally includes a first intensity threshold and a second intensity threshold. In this example, a contact with a characteristic intensity that does not exceed the first threshold results in a first operation, a contact with a characteristic intensity that exceeds the first intensity threshold and does not exceed the second intensity threshold results in a second operation, and a contact with a characteristic intensity that exceeds the second threshold results in a third operation. In some embodiments, a comparison between the characteristic intensity and one or more thresholds is used to determine whether or not to perform one or more operations (e.g., whether to perform a respective operation or forgo performing the respective operation), rather than being used to determine whether to perform a first operation or a second operation.

In some embodiments, a portion of a gesture is identified for purposes of determining a characteristic intensity. For example, a touch-sensitive surface optionally receives a continuous swipe contact transitioning from a start location and reaching an end location, at which point the intensity of the contact increases. In this example, the characteristic intensity of the contact at the end location is, optionally, based on only a portion of the continuous swipe contact, and not the entire swipe contact (e.g., only the portion of the swipe contact at the end location). In some embodiments, a smoothing algorithm is, optionally, applied to the intensities of the swipe contact prior to determining the characteristic intensity of the contact. For example, the smoothing algorithm optionally includes one or more of: an unweighted sliding-average smoothing algorithm, a triangular smoothing algorithm, a median filter smoothing algorithm, and/or an exponential smoothing algorithm. In some circumstances, these smoothing algorithms eliminate narrow spikes or dips in the intensities of the swipe contact for purposes of determining a characteristic intensity.

The intensity of a contact on the touch-sensitive surface is, optionally, characterized relative to one or more intensity thresholds, such as a contact-detection intensity threshold, a light press intensity threshold, a deep press intensity threshold, and/or one or more other intensity thresholds. In some embodiments, the light press intensity threshold corresponds to an intensity at which the device will perform operations typically associated with clicking a button of a physical mouse or a trackpad. In some embodiments, the deep press intensity threshold corresponds to an intensity at which the device will perform operations that are different from operations typically associated with clicking a button of a physical mouse or a trackpad. In some embodiments, when a contact is detected with a characteristic intensity below the light press intensity threshold (e.g., and above a nominal contact-detection intensity threshold below which the contact is no longer detected), the device will move a focus selector in accordance with movement of the contact on the touch-sensitive surface without performing an operation associated with the light press intensity threshold or the deep press intensity threshold. Generally, unless otherwise stated, these intensity thresholds are consistent between different sets of user interface figures.

An increase of characteristic intensity of the contact from an intensity below the light press intensity threshold to an intensity between the light press intensity threshold and the deep press intensity threshold is sometimes referred to as a "light press" input. An increase of characteristic intensity of the contact from an intensity below the deep press intensity threshold to an intensity above the deep press intensity threshold is sometimes referred to as a "deep press" input. An increase of characteristic intensity of the contact from an intensity below the contact-detection intensity threshold to an intensity between the contact-detection intensity threshold and the light press intensity threshold is sometimes referred to as detecting the contact on the touch-surface. A decrease of characteristic intensity of the contact from an intensity above the contact-detection intensity threshold to an intensity below the contact-detection intensity threshold is sometimes referred to as detecting liftoff of the contact from the touch-surface. In some embodiments, the contact-detection intensity threshold is zero. In some embodiments, the contact-detection intensity threshold is greater than zero.

In some embodiments described herein, one or more operations are performed in response to detecting a gesture that includes a respective press input or in response to detecting the respective press input performed with a respective contact (or a plurality of contacts), where the respective press input is detected based at least in part on detecting an increase in intensity of the contact (or plurality of contacts) above a press-input intensity threshold. In some embodiments, the respective operation is performed in response to detecting the increase in intensity of the respective contact above the press-input intensity threshold (e.g., a "down stroke" of the respective press input). In some embodiments, the press input includes an increase in intensity of the respective contact above the press-input intensity threshold and a subsequent decrease in intensity of the contact below the press-input intensity threshold, and the respective operation is performed in response to detecting the subsequent decrease in intensity of the respective contact below the press-input threshold (e.g., an "up stroke" of the respective press input).

In some embodiments, the device employs intensity hysteresis to avoid accidental inputs sometimes termed "jitter," where the device defines or selects a hysteresis intensity threshold with a predefined relationship to the press-input intensity threshold (e.g., the hysteresis intensity threshold is X intensity units lower than the press-input intensity threshold or the hysteresis intensity threshold is 75%, 90%, or some reasonable proportion of the press-input intensity threshold). Thus, in some embodiments, the press input includes an increase in intensity of the respective contact above the press-input intensity threshold and a subsequent decrease in intensity of the contact below the hysteresis intensity threshold that corresponds to the press-input intensity threshold, and the respective operation is performed in response to detecting the subsequent decrease in intensity of the respective contact below the hysteresis intensity threshold (e.g., an "up stroke" of the respective press input). Similarly, in some embodiments, the press input is detected only when the device detects an increase in intensity of the contact from an intensity at or below the hysteresis intensity threshold to an intensity at or above the press-input intensity threshold and, optionally, a subsequent decrease in intensity of the contact to an intensity at or below the hysteresis intensity, and the respective operation is performed in response to detecting the press input (e.g., the increase in intensity of the contact or the decrease in intensity of the contact, depending on the circumstances).

For ease of explanation, the descriptions of operations performed in response to a press input associated with a press-input intensity threshold or in response to a gesture including the press input are, optionally, triggered in response to detecting either: an increase in intensity of a contact above the press-input intensity threshold, an increase in intensity of a contact from an intensity below the hysteresis intensity threshold to an intensity above the press-input intensity threshold, a decrease in intensity of the contact below the press-input intensity threshold, and/or a decrease in intensity of the contact below the hysteresis intensity threshold corresponding to the press-input intensity threshold. Additionally, in examples where an operation is described as being performed in response to detecting a decrease in intensity of a contact below the press-input intensity threshold, the operation is, optionally, performed in response to detecting a decrease in intensity of the contact below a hysteresis intensity threshold corresponding to, and lower than, the press-input intensity threshold.

Attention is now directed towards embodiments of user interfaces ("UP") and associated processes that are implemented on an electronic device, such as portable multifunction device 100, device 300, or device 500.

FIGS. 6A-6E illustrate exemplary user interfaces for managing context information for an electronic device, in accordance with some embodiments. The user interfaces in these figures are used to illustrate the processes described below, including the processes in FIG. 12.

Figure 6A:
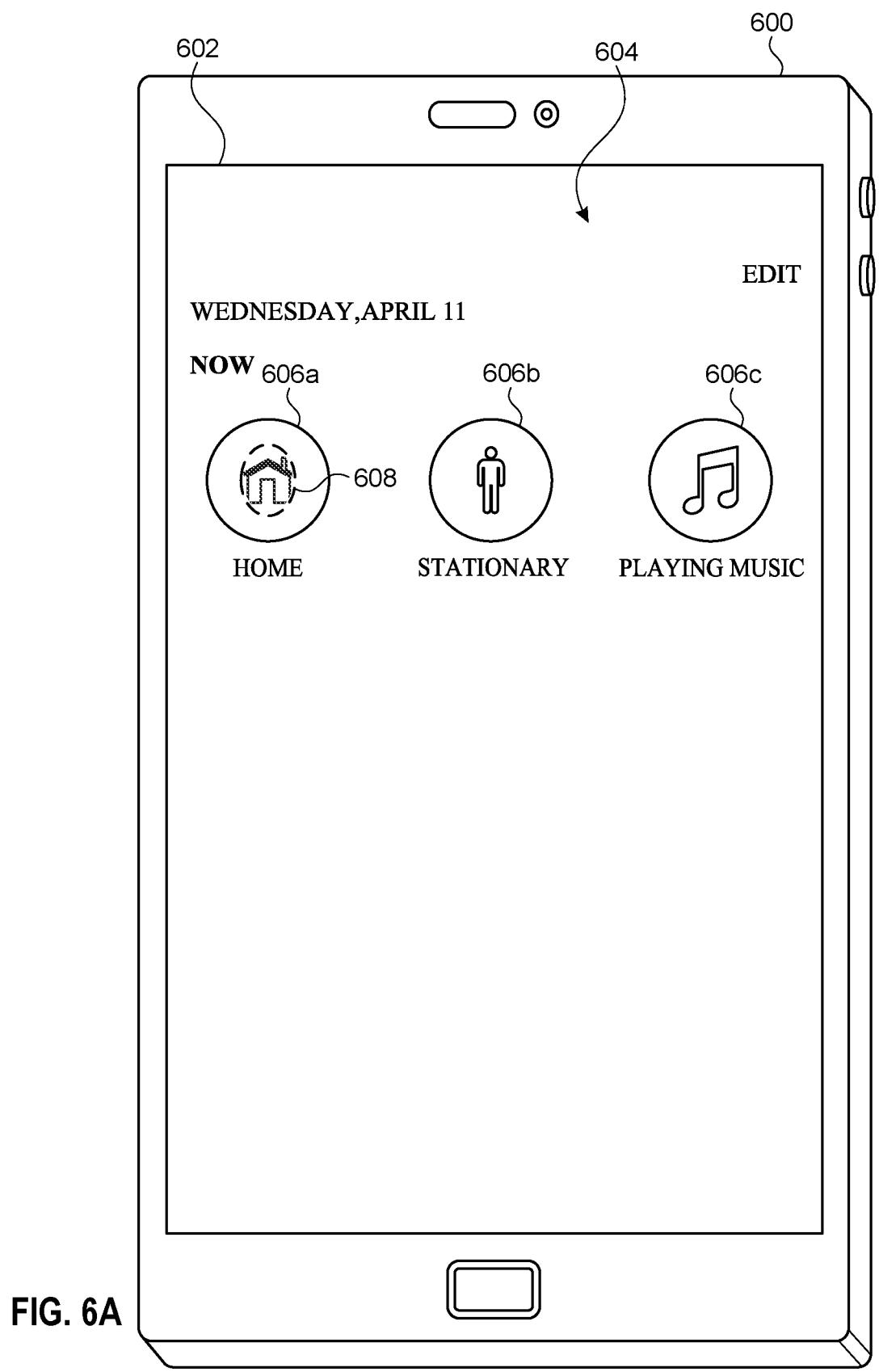
FIGS. 6A-6E illustrate exemplary user interfaces for managing context information for an electronic device in accordance with some embodiments.

FIG. 6A illustrates electronic device 600 with touch-sensitive display 602 (or with a display and a touch-sensitive surface). In some embodiments, electronic device 600 includes one or more features of device 100, 300, or 500. Electronic device 600 displays, on display 602, user interface 604 (e.g., a context management user interface). User interface 604 includes context affordances 606a-606c. Context affordances 606a-606c indicate current statuses for different contextual categories. For example, as shown in FIG. 6A, context affordance 606a ("HOME") indicates the current status for a location contextual category (e.g., the location status of electronic device 600 or a user of electronic device 600). Context affordance 606b ("STATIONARY") indicates the current status for a movement contextual category (e.g., the movement status of electronic device 600 or user of electronic device 600). Context affordance 606c ("PLAYING MUSIC") indicates the current status for an activity contextual category (e.g., the activity status of electronic device 600 or a user of electronic device 600). While shown with three context affordances 606a-606c in FIG. 6A, it should be understood that the number of context affordances displayed in user interface 604 varies based on the number of contextual categories with statuses set for them. In addition, in some embodiments, a contextual category is set with multiple current statuses (e.g., the location contextual category is set to "home" and "outside", implying a user is in the yard of their home). In the example of FIG. 6A, affordances are not displayed in the user interface for contexts that are not current or active (e.g., there is no "commuting" affordance because the device has not determined that the user is currently commuting).

In some embodiments, a current status for a contextual category is set based at least in part on information from a light sensor, a sound sensor, a camera, a location sensor (e.g., GPS), a pressure sensor, a movement sensor (e.g., accelerometer), a clock, or a radio receiver (e.g., for Wi-Fi signals) of electronic device 600. For example, when a pressure sensor of electronic device 600 detects that the ambient air pressure is changing at a rate above a threshold rate, electronic device 600 determines that a user is likely ascending or descending in an elevator, and sets the current status for the location contextual category to "in elevator". Alternatively or in addition, the determination that the user is likely in an elevator can be used by electronic device 600 to determine the other statuses for one or more contextual categories (e.g., riding an elevator implies the user is going to a meeting on a different floor, and sets the current status for a meeting contextual category to "in meeting"). As another example, when a light sensor of electronic device 600 detects that the ambient light primarily corresponds to artificial lighting (e.g., light emitted by fluorescent, LED, or incandescent light sources), electronic device 600 determines that a user is likely indoors, and sets the current status for the location contextual category to "indoors". When the light sensor of electronic device 600 detects that the ambient light primarily corresponds to natural lighting (e.g., sunlight), electronic device 600 determines that a user is likely outdoors, and sets the current status for the location contextual category to "outdoors".

In some embodiments, a current status for a contextual category is set based at least in part on schedule information (e.g., calendar), incoming communication information (e.g., call, text, email), outgoing communication information (e.g., call, text, email), or historical information (e.g., historical pattern of responding to communications means status is not busy). For example, when the schedule information includes the time and date for a flight, electronic device 600 determines that a user is likely to be at the airport near the scheduled time, and sets the current status for the location contextual category to "airport".

Figure 6B:
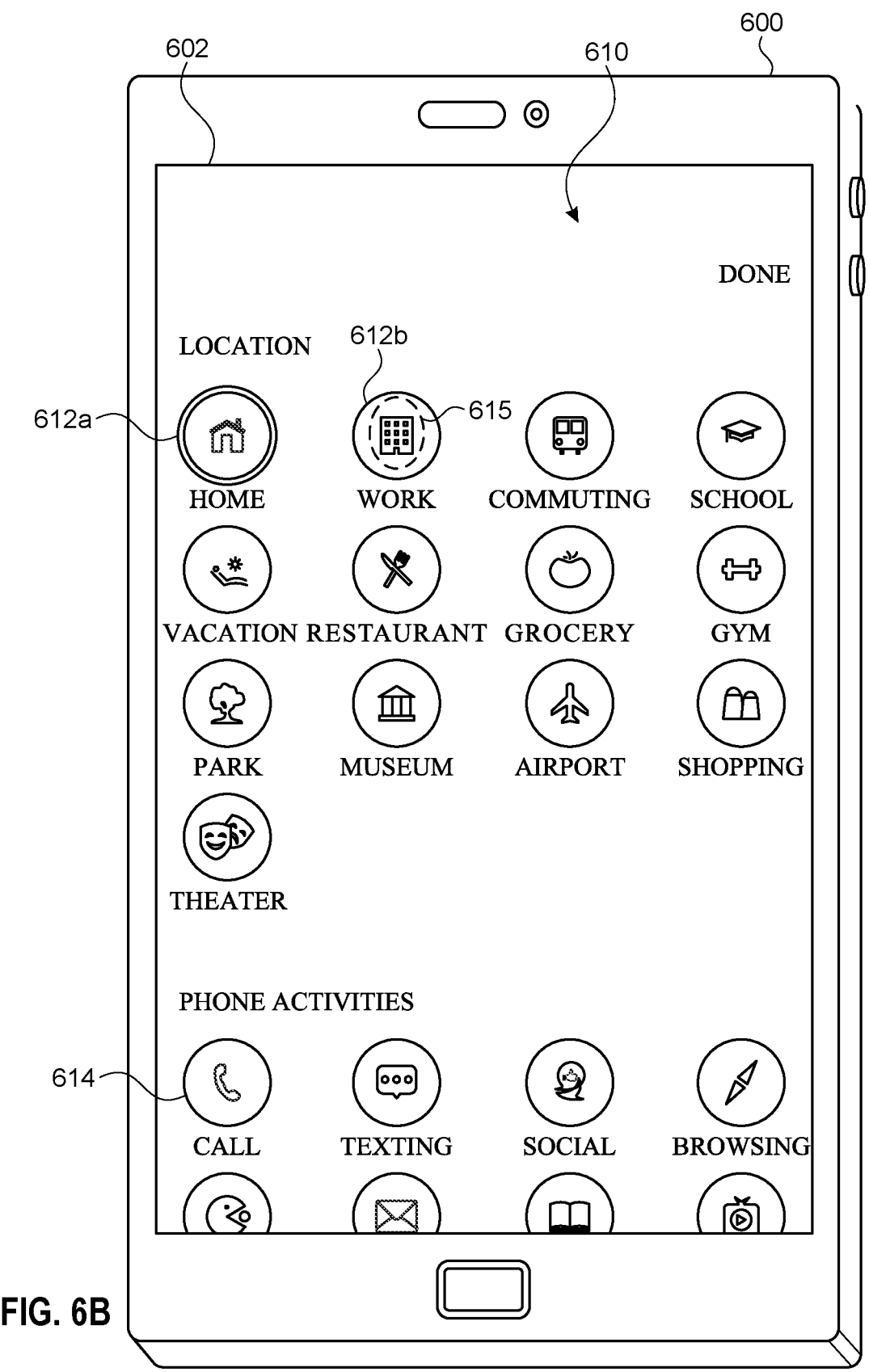

In some embodiments, the current status for one or more contextual categories can be set or changed by a user of electronic device 600. When an input 608 is detected corresponding to a context affordance (e.g., context affordance 606a), a user interface for changing the status of one or more context affordances is displayed. FIG. 6B illustrates user interface 610 for changing the status for one or more context affordances. As shown in FIG. 6B, a variety of options (e.g., 612a, 612b, 614) are displayed for different contextual categories (e.g., location, phone activities). The options represent different statuses that can be set for each contextual category. For example, the location contextual category can be set to home, work, commuting, school, vacation, restaurant, grocery, gym, park, museum, airport, shopping, theater, or to other relevant locations. The location contextual category can also be set to have no status, if the location is not known or the location contextual category is disabled. For example, user interface 610 can be used to override or revise the current context.

Figure 6C:
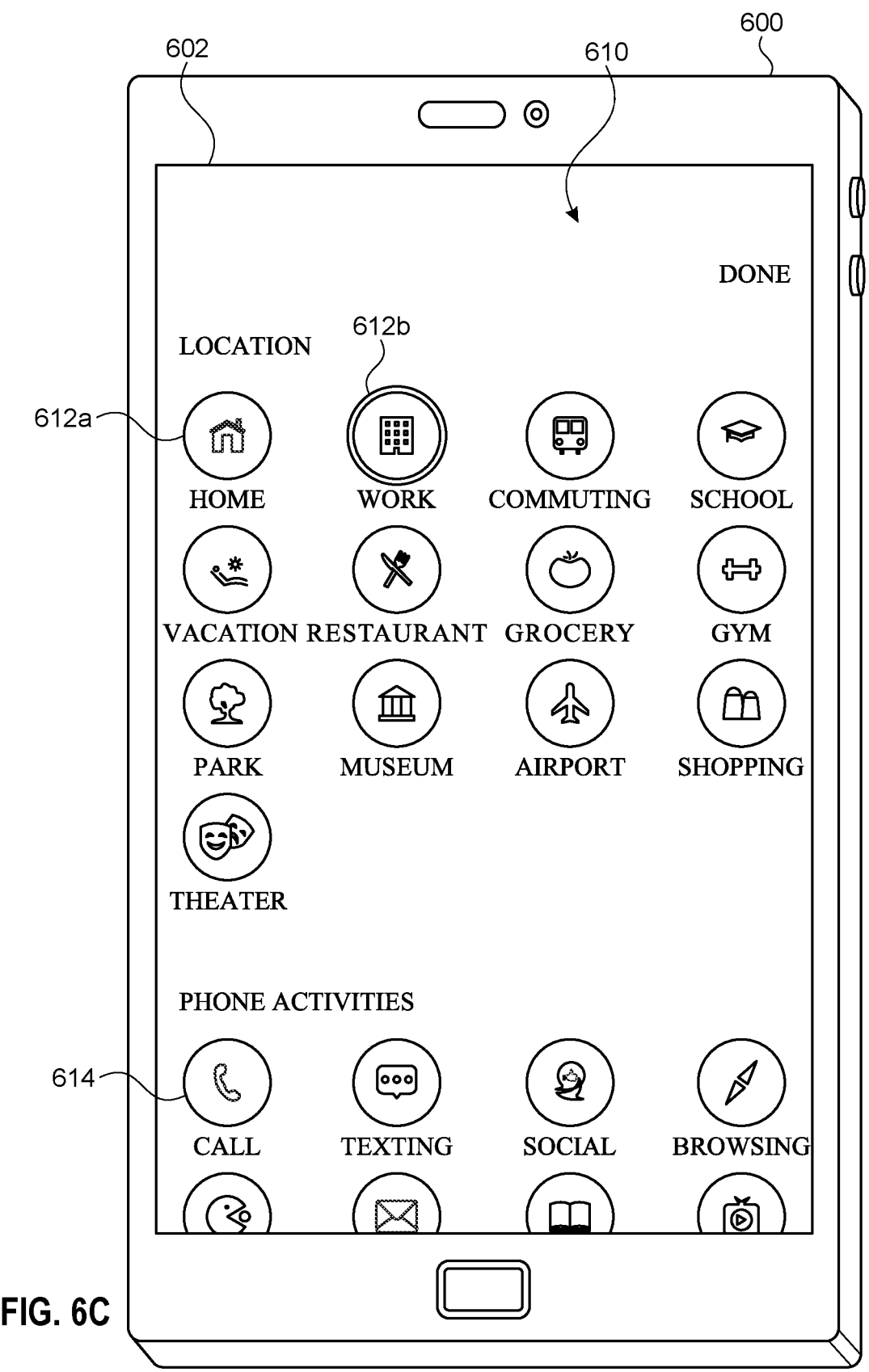

As shown in FIG. 6B, the current status for the location contextual category is set to home, as indicated by highlighting of option 612a. When an input 615 is detected corresponding to option 612b (e.g., "work"), the current status for the location contextual category is changed from option 612a to option 612b (e.g., from "home" to "work"). In response to the change in the current status for the location contextual category from option 612a to option 612b, option 612b is highlighted, as shown in FIG. 6C. Thus, active contexts for a category are visually differentiated from non-active contexts for the category. In some embodiments, selecting an option in user interface 610 results in two or more statuses being set for a contextual category. For example, when option 612b is selected, the status corresponding to option 612a remains active concurrently with the work status (e.g., in the case of someone who works from home). In some embodiments, an option (e.g., 612a or 612b) is disabled when an input corresponding to the option is detected (e.g., tapping on a highlighted option disables the status corresponding to that option).

Figure 6D:
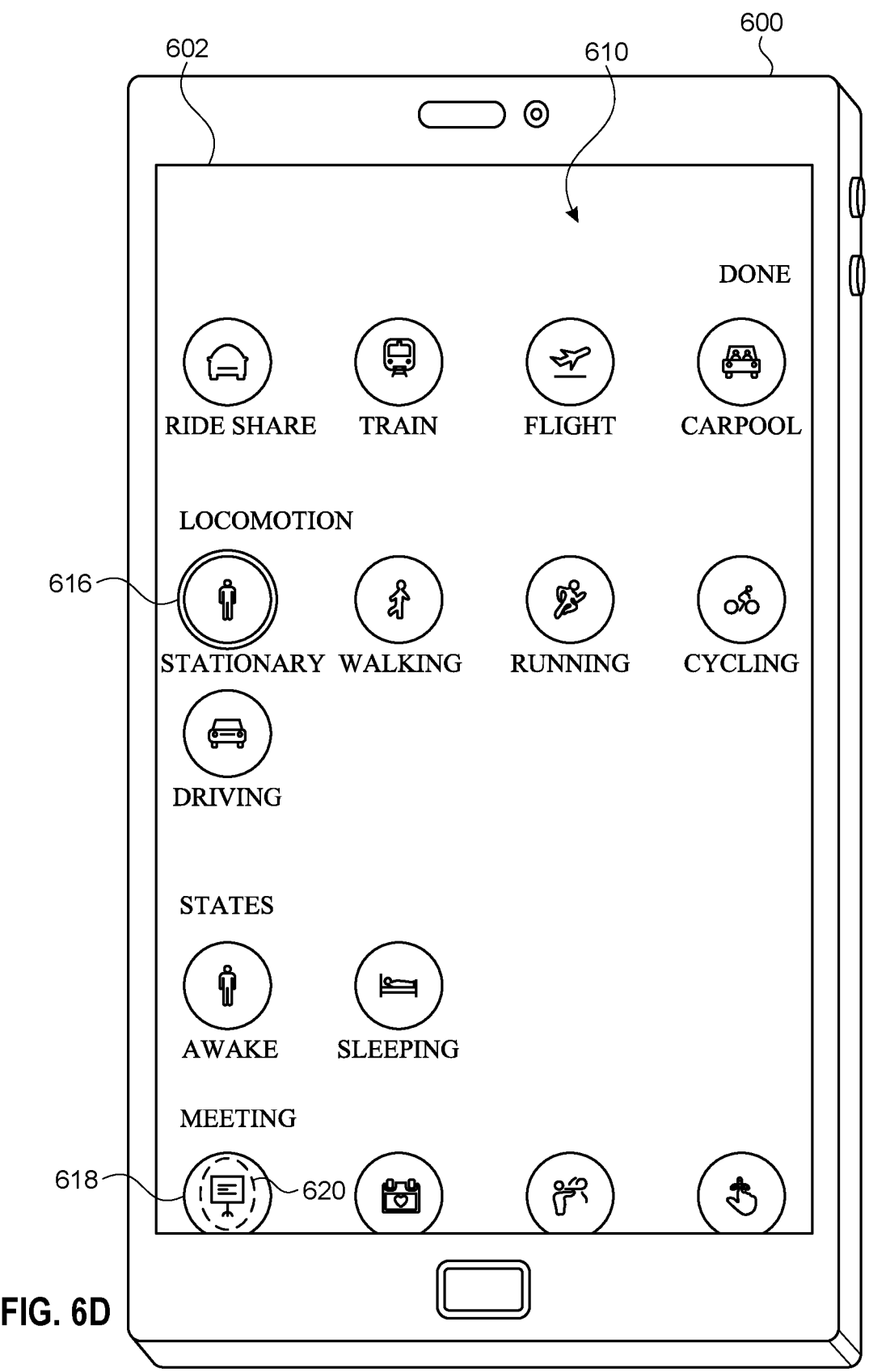

FIG. 6D illustrates an example of status options for additional contextual categories (e.g., locomotion, states, meeting). In some embodiments, user interface 610 shown in FIG. 6D is displayed in response to detecting a scrolling or swiping input on the interface shown in FIG. 6C. As shown in FIG. 6D, the locomotion contextual category is set to "stationary", as indicated by the highlighting of option 616. In the example shown in FIG. 6D, no status is set for the meeting contextual category. In response to input 620 corresponding to meeting option 618, the meeting contextual category is set to "in meeting".

Figure 6E:
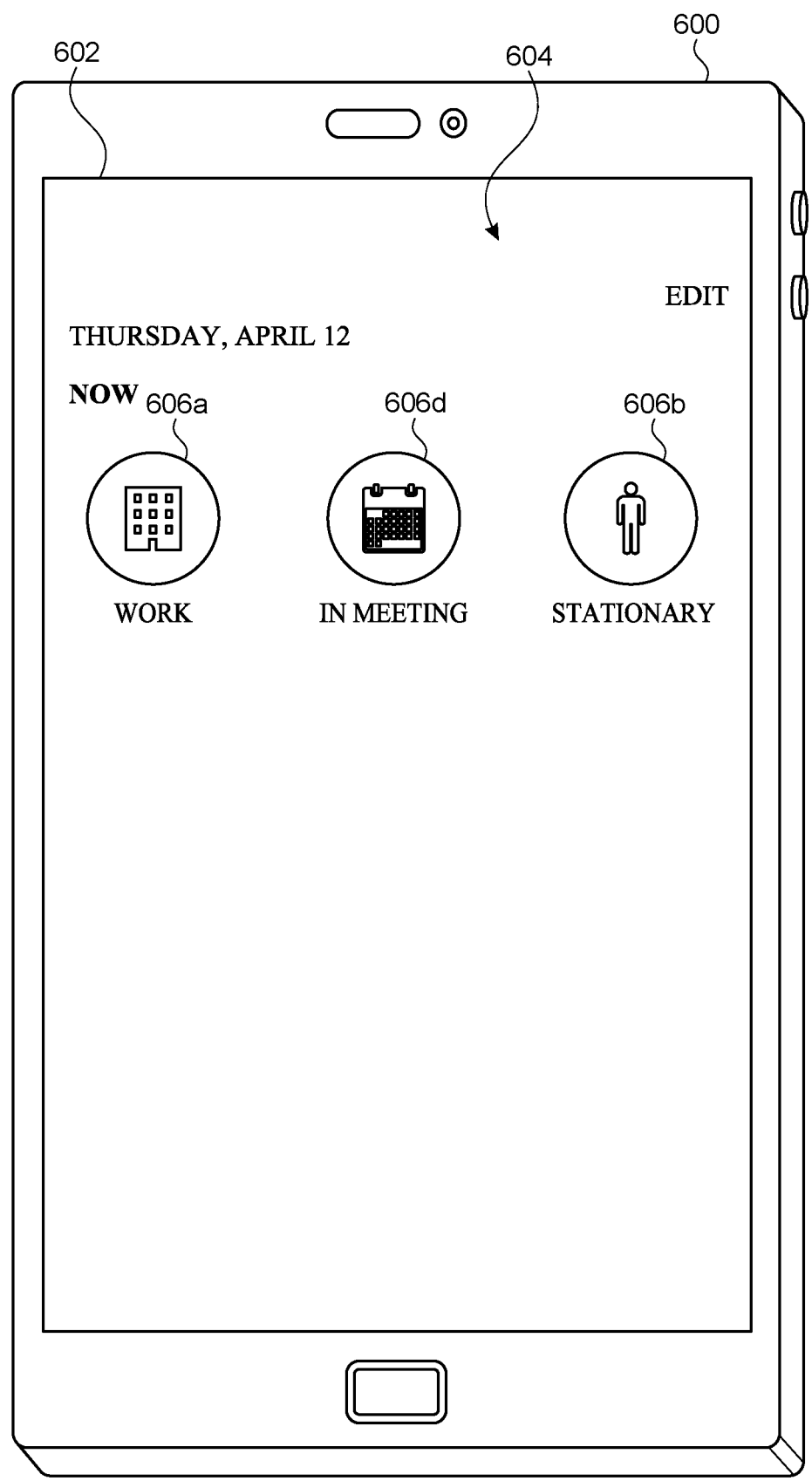

FIG. 6E illustrates an example of user interface 604 after changing the status option for contextual category 606a (e.g., the status for the location contextual category is changed to "work") and setting a new status option for contextual category 606d (e.g., a new status of "in meeting" is set for the meeting contextual category). The current status for contextual category 606b was not changed, continues to be displayed in user interface 604.

FIGS. 7A-7B illustrate exemplary user interfaces for sharing context information with a remote electronic device, in accordance with some embodiments. As shown in FIG. 7A, electronic device 600 displays, on display 602, user interface 704 (e.g., a messaging interface). User interface 704 includes contacts 706a-706d. User interface 704 further includes context information 708a associated with contact 706a, context information 708b associated with contact 706b, and context information 708d associated with contact 706d. Context information sharing is not enabled for contact 706c (e.g., "Alex"). Instead of displaying context information associated with contact 706c (since sharing is not enabled for "Alex"), share option 710 is displayed in association with contact 706c.

Context information 708a indicates one or more current statuses (e.g., "in meeting, work") for contact 706a in contextual categories that are enabled for sharing (e.g., location, meeting). Similarly, context information 708b indicates one or more current statuses (e.g., "work") for contact 706b and context information 708d indicates one or more current statuses (e.g., "home") for contact 706d. In some embodiments, other context information is displayed based on what context information is enabled for sharing.

When an input 712 is detected corresponding to share option 710 for contact 706c, then sharing is enabled for contact 706c, as shown in FIG. 7B. When sharing is enabled, context information 708c is transmitted to device 600 from a device associated with contact 706c. In some embodiments, when sharing is enabled, context information associated with device 600 is also transmitted to one or more devices associated with contacts 706a-706d (e.g., the user and contact devices exchange context information). In some embodiments, context information associated with device 600 is based on current statuses for one or more contextual categories, as described in reference to FIGS. 6A-6E.

FIGS. 8A, 8B, and 9 illustrate exemplary user interfaces for providing notifications with an electronic device based at least in part on context information, in accordance with some embodiments. The user interfaces in these figures are used to illustrate the processes described below, including the processes in FIG. 13.

As shown in FIG. 8A, electronic device 600 displays, on display 602, notification 804 (e.g., incoming chat notification). Notification 804 is displayed in response to device 600 receiving a request to join a communication session, such as a text chat, an audio call, or a virtual reality (VR) chat. However, based on the current status for one or more contextual categories, as further described in reference to FIGS. 6A-6E, device 600 determines that the communication session is unable to be joined in the requested communication mode (e.g., using text, using voice, by joining a VR chat environment). In some embodiments, the device determines that the communication session is unable be joined due to an incompatibility of device 600 to participate in the communication session (e.g., for a VR chat request, device 600 is not capable of displaying a VR chat environment). In some embodiments, the device determines that the communication session is unable to be joined due to the current status for one or more contextual categories indicating that a user of device 600 is unable to participate in the requested communication mode (e.g., when a current status associated with a locomotion category is set to "driving", the user cannot participate in a text chat or a VR chat).

In accordance with the determination that the communication session is unable to be joined in the requested communication mode, instead of displaying a notification to join communication session in the requested communication mode, device 600 modifies the notification to indicate that the communication session can be joined in a different communication mode, such as a video mode. In some embodiments, video mode notification 804 is used in response to a determination that device 600 is capable of participating in a video mode. In some embodiments, video mode notification 804 is used in response to a determination that a user of device 600 is capable of participating in a video mode based on the current status of one or more contextual categories (e.g., when the user of device 600 is at home and stationary).

When an input is detected corresponding to accept affordance 806, the communication session is entered using the video mode (e.g., for a VR chat, device 600 displays other participants of the VR chat on display 602, and provides an image of a user of device 600 to the other participants). When an input is detected corresponding to decline affordance 808, the communication session is declined and notification 804 ceases to be displayed.

FIG. 8B illustrates another example of a notification 810 displayed in response to device 600 receiving a request to join a communication session, such as a text chat, a video call, or a VR chat. In contrast to FIG. 8A, in the example of FIG. 8B, a notification to join the communication session is modified to indicate that the communication session can be joined in a voice-only mode. Based on the current status for one or more contextual categories, as further described in reference to FIGS. 6A-6E, device 600 determines that the communication session is unable to be joined in the requested communication mode (e.g., using text, using video, by joining a VR chat environment). In some embodiments, the communication session is unable be joined due to an incompatibility of device 600 to participate in the communication session (e.g., for a VR chat request, device 600 is not capable of displaying a VR chat environment). In some embodiments, the communication session is unable be joined due to the current status for one or more contextual categories indicating that a user of device 600 is unable to participate in the communication session (e.g., when a current status associated with a locomotion category is set to "driving", the user cannot participate in a text chat or a VR chat).

In accordance with the determination that the communication session is unable to be joined in the requested communication mode, device 600 modifies a notification to join the communication session to indicate that the communication session can be joined in a voice-only mode. In some embodiments, voice-only mode notification 810 is used in response to a determination that device 600 is capable of participating in a voice-only mode of the communication session. In some embodiments, voice-only mode notification 810 is used in response to a determination that a user of device 600 is capable of participating in a voice-only mode of the communication session based on the current status of one or more contextual categories (e.g., when a user of device 600 is outside and walking).

When an input is detected corresponding to accept affordance 812, the communication session is entered using the voice-only mode (e.g., for a VR chat environment, a mode where a user of device 600 is capable of hearing and talking to other participants of the VR chat). When an input is detected corresponding to decline affordance 814, the communication session is declined and notification 810 ceases to be displayed.

FIG. 9 illustrates electronic device 600 displaying, on display 602, user interface 904 (e.g., a home screen interface). In some embodiments, when electronic device 600 receives one or more notifications of a certain type, device 600 modifies the notifications into batch notification 906, as shown in FIG. 9. In some embodiments, batch notification 906 indicates the number of notifications of a certain type that have been received.

In some embodiments, the type of notifications that are modified are from a single contact, and electronic device 600 groups multiple notifications received from the single contact into batch notification 906. In some embodiments, the notifications that are modified are the same type of notification (e.g., missed call notifications), and device 600 groups the multiple notifications of the same type into the single batch notification 906.

In some embodiments, received notifications are modified based on the priority of the received notification. For example, when multiple low priority notifications are received, electronic device 600 groups the low priority notifications into batch notification 906. Alternatively, when a high priority notification is received, the high priority notification is displayed without being modified. In some embodiments, the priority of a received notification is determined based at least in part on current statuses for one or more contextual categories. For example, a received notification may be determined to be a high priority notification when a current status for a location contextual category is "grocery" and content of the received notification includes a reminder to buy potatoes.

In some embodiments, electronic device 600 utilizes batch notification 906 based on the current status of one or more contextual categories. For example, if a current status for a location contextual category is "gym" and a current status for a locomotion contextual category is "stationary", then electronic device 600 determines a user is unlikely to be available to view received notifications (e.g., the user left the electronic device 600 in a gym locker). Electronic device 600 then delays providing notifications as they are received, and instead provides batch notification 906 when the current status changes to a status where the user is likely able to view the display of device 600 (e.g., when the current status for the locomotion contextual category changes to "walking", implying the user is now carrying the electronic device 600). By combining multiple notifications into single batch notification 906, a user is notified more efficiently of received messages at a time when the user is more likely to respond, based on the current status of one or more contextual categories.

FIG. 10 illustrates an exemplary user interface for providing communication history information, in accordance with some embodiments. As shown in FIG. 10, electronic device 600 displays, on display 602, communication history 1004. Communication history 1004 indicates times and days of sent communications 1006 and received communications 1008 for a contact (e.g., "Mom"). By analyzing historical information about communications, synchronous communication times (e.g., 1010*a*, 1010*b*) are determined. Synchronous communication times (e.g., 1010*a*, 1010*b*) correspond to days and times when a sent communication 1006 is responded to with a received communication 1008, at approximately the same time (e.g., within a predefined period of time), or vice versa (e.g., both participants are communicating at the same time). Based on the synchronous communication times (e.g., 1010*a*, 1010*b*), recommendations for when to attempt communication with the contact can be provided. An example of a synchronous communication is a voice call or video call. An example of an asynchronous communication is a text message that is transmitted, but for which no response is received within the predefined period of time (e.g., within 5 minutes).

FIGS. 11A-11C illustrate exemplary user interfaces for providing communication recommendations with an electronic device based at least in part on context information, in accordance with some embodiments. The user interfaces in these figures are used to illustrate the processes described below, including the processes in FIG. 14.

As shown in FIG. 11A, electronic device 600 displays, on display 602, user interface 1104 (e.g., home screen interface). Based at least in part on communication history with a contact, as described in reference to FIG. 10, a recommendation notification 1106 is provided. Recommendation notification 1106 indicates that a contact is likely available to communicate based on the communication history. In some embodiments, recommendation notification 1106 is provided when current statuses for one or more contextual categories indicate that a user of device 600 is likely available to communicate with the contact (e.g., a current status for a location contextual category is set to "home"). In some embodiments, recommendation notification 1106 is provided when current statuses for one or more contextual categories indicate that a user of device 600 is likely available to communicate with the contact (e.g., a current status for a location contextual category is set to "home") and the device has received contextual information regarding the contact and determined that the contact is likely available to communicate (e.g., synchronously).

In some embodiments, recommendation notification 1106 is provided when contact interface 1108 is displayed by electronic device 600, as shown in FIG. 11B. Contact interface 1108 includes options 1110*a*-1110*d* for communicating with a contact associated with the contact interface 1108. Based at least on the communication history with the contact, recommendation notification 1106 indicates a preferred option for communicating with the contact. In some embodiments, the preferred option for communicating with the contact is based on current statuses for one or more contextual categories set in electronic device 600 or set in a device of the contact (e.g., the contact's device has a current status for a location contextual category set to "work").

In some embodiments, as shown in FIG. 11C, recommendation notification 1106 is provided when an attempt to communicate with a contact is initiated. As shown in FIG. 11C, electronic device 600 displays outgoing call interface 1114. Outgoing call interface 1114 is displayed when a communication is attempted (e.g., the user activates a feature to initiate a call to Jane). Based at least on the communication history with the contact, the call is optionally not initiated and, instead, recommendation notification 1106 is displayed, which indicates the contact is unlikely to respond (e.g., answer) the call. Device 600 also offers (e.g., by displaying an option for) a different recommended communication mode (e.g., send a text message instead of continuing to attempt the outgoing call). In some embodiments, the recommended communication mode is based on current statuses for one of more contextual categories set in electronic device 600 or set in a device of the contact (e.g., the contact's device has a current status for a location contextual category set to "work"). In some embodiments, when the user activates the feature to initiate a call to the contact, device 600 determines, based at least on the communication history with the contact, that the contact is likely to respond. In accordance with determining that contact is likely to respond, device 600 initiates the call to the contact (without display recommendation notification 1106 and without offering a different recommended communication mode).

When an input is detected corresponding to accept affordance 1118, the outgoing call is cancelled, and an interface for communicating in the recommended mode is displayed. When an input is detected corresponding to decline affordance 1120, the recommendation notification ceases to be displayed and the outgoing call interface 1114 is maintained. When an input is detected corresponding to end call affordance 1122, both the recommendation notification 1106 and outgoing call interface 1114 cease to be displayed (and the outgoing call is canceled without displaying the interface for communicating in the recommended mode (e.g., text message)). In some embodiments, displaying the interface for communicating in the recommended mode includes displaying an application (e.g., a text message application) that was not being displayed when recommendation notification 1106 was displayed.

FIG. 12 is a flow diagram illustrating a method for managing context information using an electronic device in accordance with some embodiments. Method 1200 is performed at a device (e.g., 100, 300, 500, 600) with a display. Some operations in method 1200 are, optionally, combined, the orders of some operations are, optionally, changed, and some operations are, optionally, omitted.

As described below, method 1200 provides an intuitive way for managing context information. The method reduces the cognitive burden on a user for setting a current context, thereby creating a more efficient human-machine interface. For battery-operated computing devices, enabling a user to manage context information faster and more efficiently conserves power and increases the time between battery charges.

At block 1202, one or more context affordances (e.g., 606*a*-606*c*) are displayed, including a first context affordance (e.g., 606*a*) associated with a first contextual category (e.g., a location category). In some embodiments, the first contextual category is location (e.g., home, work, gym), locomotion (e.g., stationary, walking, in car (driving or passenger)), transportation (e.g., public transit (train or bus), carpool, ride share, flying), state (e.g., awake, sleeping), meeting (e.g., presenting, in-person, video conference, telephone conference), or phone activity (e.g., on a call, writing a message, playing music, browsing, playing a game).

At block 1204, a first input (e.g., 608) corresponding to the first context affordance (e.g., 606*a*) is detected.

At block 1206, in response to detecting the first input, a first plurality of options (e.g., 612*a*, 612*b*) associated with the first contextual category (e.g., a location category) are displayed. The first plurality of options include a first option (e.g., a home location option 612*a*) corresponding to a first status (e.g., a status indicating a user is at home) that is a current status for the first contextual category (e.g., option 612*a* is highlighted). The first plurality of options further include a second option (e.g., a work location option 612*b*) corresponding to a second status (e.g., a status indicating the user is at work) that is not the current status for the contextual category (e.g., option 612*b* is not highlighted).

In some embodiments, the first status for the first contextual category is based at least in part on information from one or more of a light sensor, a sound sensor, a camera, a location sensor (e.g., GPS), a pressure sensor, a movement sensor (e.g., accelerometer), a clock, and a radio receiver (e.g., for Wi-Fi signals). In some embodiments, the first status for the first contextual category is based at least in part on one or more of schedule information (e.g., calendar), incoming communication information (e.g., call, text, email), outgoing communication information (e.g., call, text, email), and historical information (e.g., historical pattern of responding to communications means status is not busy).

In some embodiments, in response to detecting the first input (e.g., 608), a second plurality of options (e.g., 614, 616, 618) associated with a second contextual category (e.g., a phone activity category, a locomotion category, a meeting category, a transportation category, a state category) are displayed (e.g., the second plurality of options are displayed concurrently with the first plurality of options). In some embodiments, while displaying the second plurality of options associated with the second contextual category, a third input (e.g., 620) corresponding to a third option (e.g., 618) in the second plurality of options is detected. The third option corresponds to a third status (e.g., a status indicating the user is in a meeting) for the second contextual category (e.g., the meeting category). In response to detecting the third input (e.g., 620), the second contextual category (e.g., the meeting category) is set to the third status (e.g., the current status for the second contextual category indicates the user is in a meeting).

At block 1208, while displaying the first plurality of options (e.g., 612*a*, 612*b*) associated with the first contextual category, a second input (e.g., 615) is detected.

At block 1210, in accordance with a determination that the second input (e.g., 615) corresponds to the first option (e.g., 612*a*) of the first plurality of options, the first contextual category (e.g., the location category) associated with the first context affordance (e.g., 606*a*) is disabled (e.g., location is no longer used as part of context information or current status). In some embodiments, in accordance with the determination that the second input (e.g., 615) corresponds to the first option (e.g., 606*a*) of the first plurality of options, setting a status for the first contextual category (e.g., the location category) is forgone.

At block 1212, in accordance with a determination that the second input (e.g., 615) corresponds to the second option (e.g., 612*b*) of the first plurality of options, the current status for the first contextual category (e.g., the location category) is set to the second status (e.g., the current status is set to indicate the user is at work). In some embodiments, in accordance with the determination that the second input corresponds to the second option of the first plurality of options, the first status (e.g., the status indicating the user is at home) is removed from the current status for the first contextual category (e.g., the current status for the location category does not indicate the user is at home). In some embodiments, in accordance with the determination that the second input (e.g., 615) corresponds to the second option (e.g., 612*b*) of the first plurality of options, the first status is maintained as part of the current status for the first contextual category (e.g., the current status includes first status and second status) (e.g., the current status indicates the user is concurrently at home and at work (e.g., working from home)).

In some embodiments, the first status is provided (e.g., transmitted, such as through a wireless transmitter) (e.g., prior to detecting the second input) to a second electronic device different from the first electronic device. In some embodiments, in accordance with a determination that the second input corresponds to the second option of the plurality of options, the second status is provided to the second electronic device.

In some embodiments, a first notification associated with the first status is displayed. After the current status for the first contextual category is set to the second status, a second notification associated with the second status is displayed. In some embodiments, after disabling the first contextual category associated with the first context affordance, the display of the first notification is disabled.

Note that details of the processes described above with respect to method 1200 (e.g., FIG. 12) are also applicable in an analogous manner to the methods described below. For example, methods 1300 and 1400 optionally include one or more of the characteristics of the various methods described above with reference to method 1200. For example, the status information used in methods 1300 and 1400 can be managed using method 1200. For brevity, these details are not repeated below.

FIG. 13 is a flow diagram illustrating a method for providing notifications using an electronic device in accordance with some embodiments. Method 1300 is performed at a device (e.g., 100, 300, 500, 600). Some operations in method 1300 are, optionally, combined, the orders of some operations are, optionally, changed, and some operations are, optionally, omitted.

As described below, method 1300 provides an intuitive way for providing notifications. The method reduces the cognitive burden on a user for determining how and when a notification is viewed, thereby creating a more efficient human-machine interface. For battery-operated computing devices, enabling a user to receive notifications more efficiently conserves power and increases the time between battery charges.

At block 1302, a first notification of a first type (e.g., text, incoming call, incoming augmented reality (AR) or virtual reality (VR) request) is received. In some embodiments, notifications of the first type are high priority notifications. In some embodiments, the first notification includes a request to participate in an augmented reality or virtual reality environment.

At block 1304, a current status (e.g., of the electronic device or user of the electronic device) for one or more contextual categories (e.g., in a meeting, driving, walking across the street) is determined.

At block 1306, in accordance with a determination that the current status for the one or more contextual categories satisfies a set of one or more delivery criteria for notifications of the first type (e.g., status is not busy, device is capable of responding to the notification, notification is high priority), the first notification of the first type is provided (e.g., displayed). In some embodiments, in accordance with the determination that the current status for the one or more contextual categories satisfies the set of one or more delivery criteria for notifications of the first type, provision of a second notification of a second type is forgone (e.g., notifications 804, 810, or 906 are not displayed). In some embodiments, the set of one or more delivery criteria for notifications of the first type are based at least in part on historical context information (of the electronic device) (e.g., 1004).

At block 1308, in accordance with a determination that the current status for the one or more contextual categories does not satisfy the set of one or more delivery criteria for notifications of the first type (e.g., status is busy (DND), device is not capable of responding to the notification, notification is not high priority), the first notification of the first type is modified to a second notification of a second type (e.g., change text to voice, change VR request to a video call, place notification into a batch of notifications, delay delivery of notification) (e.g., 804, 810, or 906).

In some embodiments, the second notification of the second type is a request (e.g. 804) to participate in a video communication without participating in the augmented reality or virtual reality environment. In some embodiments, the second notification of the second type is a request (e.g., 810) to participate in an audio communication without participating in the augmented reality or virtual reality environment (and without participating in a video communication). In some embodiments, the second notification of the second type is a batch (e.g., 906) of two or more notifications of the first type. In some embodiments, the batch of two or more notifications include two or more notifications received from an external electronic device (e.g., a contact's device).

At block 1310, the second notification of the second type is provided (e.g., notifications 804, 810, or 906 are displayed). In some embodiments, in accordance with the determination that the current status for the one or more contextual categories does not satisfy the set of one or more delivery criteria for notifications of the first type, provision of the first notification of the first type is forgone (e.g., original text, incoming call, or incoming AR/VR request are not displayed).

In some embodiments, the second notification of the second type is a delayed version of the first notification of the first type. Prior to providing the second notification of the second type, the current status for one or more contextual categories is determined to have changed to a second status satisfying a set of one or more delivery criteria for notifications of the second type (e.g., movement is detected, implying device is no longer in a locker at the gym).

In some embodiments, the second notification of the second type is a hidden version of the first notification of the first type (e.g., for spam, advertisements, AR content not of interest). Prior to providing the second notification of the second type, a request is received to provide the second notification of the second type (e.g., a user preference is set to display advertisements). In some embodiments, the second notification of the second type is provided in response to receiving a (explicit) user request to provide the second notification.

Note that details of the processes described above with respect to method 1300 (e.g., FIG. 13) are also applicable in an analogous manner to the methods described above/below. For example, methods 1200 and 1400 optionally include one or more of the characteristics of the various methods described above with reference to method 1300. For example, the status information used in methods 1300 and 1400 can be managed using method 1200. For brevity, these details are not repeated below.

FIG. 14 is a flow diagram illustrating a method for recommending types of communication using an electronic device in accordance with some embodiments. Method 1400 is performed at a device (e.g., 100, 300, 500, 600). Some operations in method 1400 are, optionally, combined, the orders of some operations are, optionally, changed, and some operations are, optionally, omitted.

As described below, method 1400 provides an intuitive way for recommending a type of communication. The method reduces the cognitive burden on a user for determining the type of communication to use, thereby creating a faster and more efficient human-machine interface. For battery-operated computing devices, enabling a user to initiate communications more efficiently conserves power and increases the time between battery charges.

At block 1402, a predicted status for one or more contextual categories (e.g., available, in a meeting, driving, at home) of a potential communication participant is determined. In some embodiments, the predicted status for the one or more contextual categories of the potential communication participant is based at least in part on historical context information associated with the potential communication participant (e.g., context during previous communications with the potential communication participant, date and times of previous communications with the potential communication participant). In some embodiments, the predicted status for the one or more contextual categories of the potential communication participant is based at least in part on status information received from a device associated with the potential communication participant (e.g., the potential communication participant provides their current status, such as in meeting, at work, at home, driving, etc.).

In some embodiments, at block 1404, an attempt to initiate communication with the potential communication participant is detected. In some embodiments, detecting the attempt includes receiving a request to initiate a video conference call with the potential communication participant.

In some embodiments, at block 1406, active usage of the electronic device is detected (e.g., a user is engaged with the electronic device). In some embodiments, detecting active usage of the electronic device includes detecting a user picking up the electronic device, detecting a user is viewing information on the display of the electronic device, or detecting a user is accessing information from the electronic device.

At block 1408, in accordance with a determination that the predicted status for the one or more contextual categories satisfies a set of one or more communication criteria (e.g., potential participant is not busy, potential participant's device is capable of responding to the communication), a first recommendation (e.g., 1106) to initiate a first type of communication (e.g., telephone call, video call) with the potential communication participant is provided (e.g., displayed).

At block 1410, in accordance with a determination that the predicted status for the one or more contextual categories does not satisfy the set of one or more communication criteria (e.g., potential participant is busy, potential participant's device is not capable of responding to the communication), a second recommendation (e.g., 1106) to initiate a second type of communication (e.g., text, email, call at a different time) with the potential communication participant is provided (e.g., displayed).

In some embodiments, the first recommendation or the second recommendation is provided in response to detecting an attempt to initiate communication with the potential communication participant. In some embodiments, the first type of communication is an active communication (e.g., audio call, video call) and the second type of communication is a passive communication (e.g., text, email). In some embodiments, the first type of communication is a communication at the current time the first recommendation is provided (e.g., communication with the participant starts immediately) and the second type of communication is a communication at a future time after the second recommendation is provided (e.g., request communication at a future time when the participant is likely to be available). In some embodiments, the future time is based at least in part on historical context information (e.g., 1004) associated with the potential communication participant (e.g., historical time and days when the participant is available and responds to messages).

In some embodiments, in accordance with the determination that the predicted status for the one or more contextual categories does not satisfy the set of one or more communication criteria, provision of the first recommendation (e.g., 1106) to initiate the first type of communication (e.g., telephone call, video call) with the potential communication participant is forgone. In some embodiments, in accordance with the determination that the predicted status for the one or more contextual categories satisfies the set of one or more communication criteria, provision of the second recommendation (e.g., 1106) to initiate the second type of communication (e.g., text, email, call at a different time) with the potential communication participant is forgone.

Note that details of the processes described above with respect to method 1400 (e.g., FIG. 14) are also applicable in an analogous manner to the methods described above. For example, methods 1200 and 1300 optionally include one or more of the characteristics of the various methods described above with reference to method 1400. For example, the status information used in method 1400 can be managed using method 1200. For brevity, these details are not repeated below.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the claims.

As described above, one aspect of the present technology is the gathering and use of data available from various sources to set statuses for contextual categories. The present disclosure contemplates that in some instances, this gathered data may include personal information data that uniquely identifies or can be used to contact or locate a specific person. Such personal information data can include context information, demographic data, location-based data, telephone numbers, email addresses, twitter IDs, home addresses, or any other identifying or personal information.

The present disclosure recognizes that the use of such personal information data, in the present technology, can be used to the benefit of users. For example, the personal information data can be used to provide notifications when a user is capable of engaging with the notifications. Further, other uses for personal information data that benefit the user are also contemplated by the present disclosure.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, the present technology can be configured to allow users to select to "opt in" or "opt out" of participation in the collection of personal information data during registration for services or anytime thereafter. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, statuses for one or more contextual categories can determined by inferring statuses based on non-personal information data or a bare minimum amount of personal information, such as the content being requested by the device associated with a user, other non-personal information available to the device, or publicly available information.

What is claimed is:

1. A first electronic device, comprising:
   a display;
   one or more processors; and
   memory storing one or more programs configured to be executed by the one or more processors, the one or more programs including instructions for:
      displaying one or more context affordances, including a first context affordance associated with a first contextual category;
      detecting a first input corresponding to the first context affordance;
      in response to detecting the first input, displaying a first plurality of options associated with the first contextual category, the first plurality of options including a first option corresponding to a first status that is a current status for the first contextual category and a second option corresponding to a second status that is not the current status for the first contextual category;
      while displaying the first plurality of options associated with the first contextual category, detecting a second input;
      in accordance with a determination that the second input corresponds to the first option of the first plurality of options:
         disabling the first contextual category associated with the first context affordance; and
      in accordance with a determination that the second input corresponds to the second option of the first plurality of options:
         setting the current status for the first contextual category to the second status.

2. The first electronic device of claim 1, wherein the one or more programs further include instructions for:
   in accordance with the determination that the second input corresponds to the first option of the first plurality of options:
      forgoing setting a status for the first contextual category.

3. The first electronic device of claim 1, wherein the one or more programs further include instructions for:
   in accordance with the determination that the second input corresponds to the second option of the first plurality of options:
      removing the first status from the current status for the first contextual category.

4. The first electronic device of claim 1, comprising wherein the one or more programs further include instructions for:
   in accordance with the determination that the second input corresponds to the second option of the first plurality of options:
      maintaining the first status as part of the current status for the first contextual category.

5. The first electronic device of claim 1, wherein the one or more programs further include instructions for:
   in response to detecting the first input, displaying a second plurality of options associated with a second contextual category.

6. The first electronic device of claim 5, wherein the one or more programs further include instructions for:
   while displaying the second plurality of options associated with the second contextual category:
      detecting a third input corresponding to a third option in the second plurality of options, the third option corresponding to a third status for the second contextual category; and
      in response to detecting the third input, setting the second contextual category to the third status.

7. The first electronic device of claim 1, wherein the one or more programs further include instructions for:
   providing the first status to a second electronic device different from the first electronic device; and
   in accordance with a determination that the second input corresponds to the second option of the first plurality of options:
      providing the second status to the second electronic device.

8. The first electronic device of claim 1, further wherein the one or more programs further include instructions for:
   displaying a first notification associated with the first status; and
   after setting the current status for the first contextual category to the second status, displaying a second notification associated with the second status.

9. The first electronic device of claim 1, wherein the first contextual category is location, movement, or activity.

10. The first electronic device of claim 1, wherein the first status for the first contextual category is based at least in part on information from one or more of a light sensor, a sound sensor, a camera, a location sensor, a pressure sensor, a movement sensor, a clock, and a radio receiver.

11. The first electronic device of claim 1, wherein the first status for the first contextual category is based at least in part on one or more of schedule information, incoming communication information, outgoing communication information, and historical information.

12. A non-transitory computer-readable storage medium storing one or more programs configured to be executed by one or more processors of a first electronic device with a display, the one or more programs including instructions for:
   displaying one or more context affordances, including a first context affordance associated with a first contextual category;
   detecting a first input corresponding to the first context affordance;

in response to detecting the first input, displaying a first plurality of options associated with the first contextual category, the first plurality of options including a first option corresponding to a first status that is a current status for the first contextual category and a second option corresponding to a second status that is not the current status for the first contextual category;

while displaying the first plurality of options associated with the first contextual category, detecting a second input;

in accordance with a determination that the second input corresponds to the first option of the first plurality of options:

disabling the first contextual category associated with the first context affordance; and in accordance with a determination that the second input corresponds to the second option of the first plurality of options:

setting the current status for the first contextual category to the second status.

13. The non-transitory computer-readable storage medium of claim 12, wherein the one or more programs further include instructions for:

in accordance with the determination that the second input corresponds to the first option of the first plurality of options:

forgoing setting a status for the first contextual category.

14. The non-transitory computer-readable storage medium of claim 12, wherein the one or more programs further include instructions for:

in accordance with the determination that the second input corresponds to the second option of the first plurality of options:

removing the first status from the current status for the first contextual category.

15. The non-transitory computer-readable storage medium of claim 12, wherein the one or more programs further include instructions for:

in accordance with the determination that the second input corresponds to the second option of the first plurality of options:

maintaining the first status as part of the current status for the first contextual category.

16. The non-transitory computer-readable storage medium of claim 12, wherein the one or more programs further include instructions for:

in response to detecting the first input, displaying a second plurality of options associated with a second contextual category.

17. The non-transitory computer-readable storage medium of claim 16, wherein the one_or more programs further include instructions for:

while displaying the second plurality of options associated with the second contextual category:

detecting a third input corresponding to a third option in the second plurality of options, the third option corresponding to a third status for the second contextual category; and in response to detecting the third input, setting the second contextual category to the third status.

18. The non-transitory computer-readable storage medium of claim 12, wherein the one or more programs further include instructions for:

providing the first status to a second electronic device different from the first electronic device; and in accordance with a determination that the second input corresponds to the second option of the first plurality of options:

providing the second status to the second electronic device.

19. The non-transitory computer-readable storage medium of claim 12, wherein the one or more programs further include instructions for:

displaying a first notification associated with the first status; and after setting the current status for the first contextual category to the second status, displaying a second notification associated with the second status.

20. The non-transitory computer-readable storage medium of claim 12, wherein the first contextual category is location, movement, or activity.

21. The non-transitory computer-readable storage medium of claim 12, wherein the first status for the first contextual category is based at least in part on information from one or more of a light sensor, a sound sensor, a camera, a location sensor, a pressure sensor, a movement sensor, a clock, and a radio receiver.

22. The non-transitory computer-readable storage medium of claim 12, wherein the first status for the first contextual category is based at least in part on one or more of schedule information, incoming communication information, outgoing communication information, and historical information.

23. A method, comprising:

at a first electronic device with a display:

displaying one or more context affordances, including a first context affordance associated with a first contextual category;

detecting a first input corresponding to the first context affordance;

in response to detecting the first input, displaying a first plurality of options associated with the first contextual category, the first plurality of options including a first option corresponding to a first status that is a current status for the first contextual category and a second option corresponding to a second status that is not the current status for the first contextual category;

while displaying the first plurality of options associated with the first contextual category, detecting a second input;

in accordance with a determination that the second input corresponds to the first option of the first plurality of options:

disabling the first contextual category associated with the first context affordance; and in accordance with a determination that the second input corresponds to the second option of the first plurality of options:

setting the current status for the first contextual category to the second status.

24. The method of claim 23, further comprising:

in accordance with the determination that the second input corresponds to the first option of the first plurality of options:

forgoing setting a status for the first contextual category.

25. The method of claim 23, further comprising:

in accordance with the determination that the second input corresponds to the second option of the first plurality of options:

removing the first status from the current status for the first contextual category.

26. The method of claim 23, further comprising:
in accordance with the determination that the second input corresponds to the second option of the first plurality of options:
   maintaining the first status as part of the current status for the first contextual category.

27. The method of claim 23, further comprising:
in response to detecting the first input, displaying a second plurality of options associated with a second contextual category.

28. The method of claim 27, further comprising:
while displaying the second plurality of options associated with the second contextual category:
   detecting a third input corresponding to a third option in the second plurality of options, the third option corresponding to a third status for the second contextual category; and
   in response to detecting the third input, setting the second contextual category to the third status.

29. The method of claim 23, further comprising:
providing the first status to a second electronic device different from the first electronic device; and
in accordance with a determination that the second input corresponds to the second option of the first plurality of options:
   providing the second status to the second electronic device.

30. The method of claim 23, further comprising:
displaying a first notification associated with the first status; and
after setting the current status for the first contextual category to the second status, displaying a second notification associated with the second status.

31. The method of claim 23, wherein the first contextual category is location, movement, or activity.

32. The method of claim 23, wherein the first status for the first contextual category is based at least in part on information from one or more of a light sensor, a sound sensor, a camera, a location sensor, a pressure sensor, a movement sensor, a clock, and a radio receiver.

33. The method of claim 23, wherein the first status for the first contextual category is based at least in part on one or more of schedule information, incoming communication information, outgoing communication information, and historical information.

\* \* \* \* \*

UNITED STATES PATENT AND TRADEMARK OFFICE
CERTIFICATE OF CORRECTION

| | | |
|---|---|---|
| PATENT NO. | : 11,973,894 B2 | Page 1 of 1 |
| APPLICATION NO. | : 17/607830 | |
| DATED | : April 30, 2024 | |
| INVENTOR(S) | : Golnaz Abdollahian et al. | |

It is certified that error appears in the above-identified patent and that said Letters Patent is hereby corrected as shown below:

In the Claims

Claim 4, Column 46, Lines 8-9:
Delete "comprising wherein" and insert --wherein--.

Claim 8, Column 46, Line 40:
Delete "further wherein" and insert --wherein--.

Claim 51, Column 47, Line 1:
Delete "one_or" and insert --one or--.

Signed and Sealed this
Twelfth Day of November, 2024

Katherine Kelly Vidal
*Director of the United States Patent and Trademark Office*